United States Patent
Balbierz et al.

(10) Patent No.: US 9,055,942 B2
(45) Date of Patent: *Jun. 16, 2015

(54) ENDOSCOPIC PLICATION DEVICES AND METHODS

(75) Inventors: Daniel J. Balbierz, Redwood City, CA (US); Dave Cole, San Mateo, CA (US); Samuel T. Crews, Woodside, CA (US); Brett Swope, Gaithersburg, MD (US); Andrew Smith, San Francisco, CA (US); John Lunsford, San Carlos, CA (US); Fiona Sander, Los Altos Hills, CA (US)

(73) Assignee: Boston Scienctific Scimed, Inc., Maple Grove, MN (US)

( * ) Notice: Subject to any disclaimer, the term of this patent is extended or adjusted under 35 U.S.C. 154(b) by 1940 days.

This patent is subject to a terminal disclaimer.

(21) Appl. No.: 11/542,457

(22) Filed: Oct. 3, 2006

(65) Prior Publication Data

US 2007/0219571 A1    Sep. 20, 2007

Related U.S. Application Data

(60) Provisional application No. 60/723,160, filed on Oct. 3, 2005, provisional application No. 60/754,417, filed on Dec. 28, 2005, provisional application No. 60/825,534, filed on Sep. 13, 2006.

(51) Int. Cl.
*A61B 17/08* (2006.01)
*A61B 17/068* (2006.01)
(Continued)

(52) U.S. Cl.
CPC ........... *A61B 17/068* (2013.01); *A61B 17/0218* (2013.01); *A61B 17/072* (2013.01);
(Continued)

(58) Field of Classification Search
CPC .... A61B 17/00; A61B 17/068; A61B 17/072; A61B 2017/00535; A61B 2017/00561; A61B 2017/00566; A61B 2017/072214; A61B 2017/00827

USPC ................ 606/139, 205, 144–148; 227/175.1
See application file for complete search history.

(56) References Cited

U.S. PATENT DOCUMENTS

| 1,408,865 A | 3/1922 | Cowell |
| 3,663,965 A | 5/1972 | Lee et al. |

(Continued)

FOREIGN PATENT DOCUMENTS

| CH | 680263 A5 | 7/1992 |
| EP | 0775471 | 5/1997 |

(Continued)

OTHER PUBLICATIONS

Stecco, K. et al., "Trans-Oral Plication Formation and Gastric Implant Placement in a Canine Model", Stecco Group, San Jose and Barosnese, Inc., Redwood City, California (2004).

(Continued)

*Primary Examiner* — Gregory Anderson
*Assistant Examiner* — Christina Lauer
(74) *Attorney, Agent, or Firm* — Bookoff McAndrews, PLLC

(57) ABSTRACT

Endoscopic plicators are passed transorally into the stomach and used to plicate stomach tissue by engaging tissue from inside of the stomach and drawing it inwardly. The tissue is drawn inwardly into a vacuum chamber, causing sections of serosal tissue on the exterior of the stomach to be positioned facing one another. The plicators allow the opposed sections of tissue to be moved into contact with one another, and preferably deliver sutures, staples or other means for maintaining contact between the tissue sections at least until serosal bonds form between them. Each of these steps may be performed wholly from the inside of the stomach and thus can eliminate the need for any surgical or laparscopic intervention. After one or more plications is formed, medical devices may be coupled to the plication(s) for retention within the stomach.

17 Claims, 36 Drawing Sheets

(51) Int. Cl.
*A61B 17/072* (2006.01)
*A61B 17/115* (2006.01)
*A61B 17/128* (2006.01)
A61B 17/02 (2006.01)
A61B 17/00 (2006.01)
A61B 17/30 (2006.01)

(52) U.S. Cl.
CPC ......... A61B17/07292 (2013.01); *A61B 17/115* (2013.01); *A61B 17/1285* (2013.01); A61B 2017/00535 (2013.01); A61B 2017/00827 (2013.01); A61B 2017/07214 (2013.01); A61B 2017/1157 (2013.01); A61B 2017/306 (2013.01)

(56) References Cited

U.S. PATENT DOCUMENTS

| | | |
|---|---|---|
| 4,134,405 A | 1/1979 | Smit |
| 4,207,890 A | 6/1980 | Mamajek et al. |
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |
| 4,485,805 A | 12/1984 | Foster, Jr. |
| 4,488,523 A * | 12/1984 | Shichman .................. 227/179.1 |
| 4,501,264 A | 2/1985 | Rockey |
| 4,607,618 A | 8/1986 | Angelchik |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galtier |
| 4,846,836 A | 7/1989 | Reich |
| 4,848,367 A | 7/1989 | Avant et al. |
| 4,899,747 A | 2/1990 | Garren et al. |
| 4,925,446 A | 5/1990 | Garay et al. |
| 4,946,440 A | 8/1990 | Hall |
| 4,969,896 A | 11/1990 | Shors |
| 4,997,084 A | 3/1991 | Opie et al. |
| 5,006,106 A | 4/1991 | Angelchik |
| 5,037,021 A | 8/1991 | Mills et al. ..................... 227/175 |
| 5,061,275 A | 10/1991 | Wallsten et al. |
| 5,084,061 A | 1/1992 | Gau et al. |
| 5,088,979 A | 2/1992 | Filipi et al. ...................... 604/26 |
| 5,163,952 A | 11/1992 | Froix |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,263,629 A | 11/1993 | Trumbull et al. |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shain |
| 5,355,897 A | 10/1994 | Pietrafitta et al. |
| 5,401,241 A | 3/1995 | Delany |
| 5,403,326 A | 4/1995 | Harrison et al. .............. 606/139 |
| 5,405,377 A | 4/1995 | Cragg |
| 5,431,673 A | 7/1995 | Summers et al. |
| 5,486,187 A | 1/1996 | Schneck |
| 5,514,176 A | 5/1996 | Bosley, Jr. |
| 5,535,935 A | 7/1996 | Vidal et al. |
| 5,542,949 A | 8/1996 | Yoon |
| 5,562,239 A | 10/1996 | Boiarski et al. |
| 5,571,116 A | 11/1996 | Bolanos et al. .............. 606/139 |
| 5,577,654 A | 11/1996 | Bishop |
| 5,593,434 A | 1/1997 | Williams |
| 5,597,107 A | 1/1997 | Knodel et al. |
| 5,609,624 A | 3/1997 | Kalis |
| 5,628,786 A | 5/1997 | Banas et al. |
| 5,630,539 A | 5/1997 | Plyley et al. |
| 5,647,526 A | 7/1997 | Green et al. |
| 5,653,743 A | 8/1997 | Martin |
| 5,662,713 A | 9/1997 | Andersen et al. |
| 5,673,841 A | 10/1997 | Schulze et al. |
| 5,674,241 A | 10/1997 | Bley et al. |
| 5,706,998 A | 1/1998 | Plyley et al. |
| 5,709,657 A | 1/1998 | Zimmon |
| 5,720,776 A | 2/1998 | Chuter et al. |
| 5,749,918 A | 5/1998 | Hogendijk et al. |
| 5,762,255 A | 6/1998 | Chrisman et al. |
| 5,771,903 A | 6/1998 | Jakobsson |
| 5,785,684 A | 7/1998 | Zimmon |
| 5,820,584 A | 10/1998 | Crabb |
| 5,839,639 A | 11/1998 | Sauer et al. ................. 227/175.1 |
| 5,848,964 A | 12/1998 | Samuels |
| 5,855,311 A | 1/1999 | Hamblin et al. |
| 5,855,601 A | 1/1999 | Bessler et al. |
| 5,856,445 A | 1/1999 | Korsmeyer |
| 5,861,036 A | 1/1999 | Godin |
| 5,868,141 A | 2/1999 | Ellias |
| 5,887,594 A | 3/1999 | LoCicero et al. ............. 128/898 |
| 5,897,562 A | 4/1999 | Bolanos et al. ............... 606/139 |
| 5,910,144 A | 6/1999 | Hayashi et al. |
| 5,922,019 A | 7/1999 | Hankh et al. |
| 5,947,983 A | 9/1999 | Solar et al. .................... 606/144 |
| 5,993,473 A | 11/1999 | Chan et al. |
| 5,993,483 A | 11/1999 | Gianotti |
| 6,016,848 A | 1/2000 | Egres, Jr. |
| 6,051,015 A | 4/2000 | Maahs |
| 6,086,600 A | 7/2000 | Kortenback .................. 606/139 |
| 6,098,629 A | 8/2000 | Johnson et al. |
| 6,102,922 A | 8/2000 | Jakobsson et al. |
| 6,113,609 A | 9/2000 | Adams |
| 6,120,534 A | 9/2000 | Ruiz |
| 6,146,416 A | 11/2000 | Andersen et al. |
| 6,159,146 A | 12/2000 | El Gazayerli ................. 600/106 |
| 6,159,238 A | 12/2000 | Killion et al. |
| 6,197,022 B1 | 3/2001 | Baker ............................. 606/33 |
| 6,206,930 B1 | 3/2001 | Burg et al. |
| 6,245,088 B1 | 6/2001 | Lowery |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,287,334 B1 | 9/2001 | Moll et al. |
| 6,302,917 B1 | 10/2001 | Dua et al. |
| 6,358,197 B1 * | 3/2002 | Silverman et al. ............... 600/29 |
| 6,416,522 B1 | 7/2002 | Strecker |
| 6,425,916 B1 | 7/2002 | Garrison et al. |
| 6,454,785 B2 | 9/2002 | De Hoyos Garza |
| 6,460,543 B1 | 10/2002 | Forsell |
| 6,461,366 B1 | 10/2002 | Seguin |
| 6,494,888 B1 | 12/2002 | Laufer et al. .................. 606/153 |
| 6,494,895 B2 | 12/2002 | Addis |
| 6,503,264 B1 | 1/2003 | Birk |
| 6,506,196 B1 | 1/2003 | Laufer et al. .................. 606/142 |
| 6,527,784 B2 | 3/2003 | Adams et al. |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor et al. |
| 6,572,627 B2 | 6/2003 | Gabbay |
| 6,572,629 B2 | 6/2003 | Kalloo |
| 6,575,896 B2 | 6/2003 | Silverman |
| 6,592,596 B1 | 7/2003 | Geitz ............................. 606/139 |
| 6,596,023 B1 | 7/2003 | Nunez et al. |
| 6,607,555 B2 | 8/2003 | Patterson et al. |
| 6,627,206 B2 | 9/2003 | Lloyd |
| 6,632,227 B2 | 10/2003 | Adams |
| 6,663,639 B1 | 12/2003 | Laufer ........................... 606/139 |
| 6,675,809 B2 | 1/2004 | Stack et al. |
| 6,740,098 B2 | 5/2004 | Abrams et al. |
| 6,740,121 B2 | 5/2004 | Geitz |
| 6,746,460 B2 | 6/2004 | Gannoe et al. |
| 6,755,869 B2 | 6/2004 | Geitz |
| 6,764,518 B2 | 7/2004 | Godin |

(56) References Cited

U.S. PATENT DOCUMENTS

| | | | |
|---|---|---|---|
| 6,773,440 B2 | 8/2004 | Gannoe et al. | 606/142 |
| 6,773,441 B1 | 8/2004 | Laufer et al. | 606/153 |
| 6,790,214 B2 | 9/2004 | Kraemer et al. | |
| 6,790,237 B2 | 9/2004 | Stinson | |
| 6,821,285 B2 | 11/2004 | Laufer et al. | 606/153 |
| 6,835,200 B2 | 12/2004 | Laufer et al. | 606/153 |
| 6,845,776 B2 | 1/2005 | Stack et al. | |
| 6,916,332 B2 | 7/2005 | Adams | |
| 6,932,838 B2 | 8/2005 | Schwartz et al. | |
| 6,960,233 B1 | 11/2005 | Berg et al. | |
| 6,966,875 B1 | 11/2005 | Longobardi | |
| 6,981,978 B2 | 1/2006 | Gannoe | 606/153 |
| 6,981,980 B2 | 1/2006 | Sampson et al. | |
| 6,994,715 B2 | 2/2006 | Gannoe et al. | 606/153 |
| 7,011,094 B2 | 3/2006 | Rapackie et al. | |
| 7,020,531 B1 | 3/2006 | Colliou et al. | 607/133 |
| 7,025,791 B2 | 4/2006 | Levine et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,056,305 B2 | 6/2006 | Garza | |
| 7,066,945 B2 | 6/2006 | Hashiba et al. | |
| 7,083,629 B2 | 8/2006 | Weller et al. | |
| 7,090,699 B2 | 8/2006 | Geitz | |
| 7,097,650 B2 | 8/2006 | Weller et al. | 606/153 |
| 7,097,665 B2 | 8/2006 | Stack et al. | |
| 7,111,627 B2 | 9/2006 | Stack et al. | |
| 7,112,186 B2 | 9/2006 | Shah | |
| 7,141,055 B2* | 11/2006 | Abrams et al. | 606/115 |
| 7,175,638 B2 | 2/2007 | Gannoe et al. | 606/153 |
| 8,469,977 B2* | 6/2013 | Balbierz et al. | 606/153 |
| 2001/0011543 A1 | 8/2001 | Forsell | |
| 2001/0020189 A1 | 9/2001 | Taylor | |
| 2001/0020190 A1 | 9/2001 | Taylor | |
| 2001/0021796 A1 | 9/2001 | Silverman et al. | |
| 2001/0044595 A1 | 11/2001 | Reydel et al. | |
| 2001/0049492 A1* | 12/2001 | Frazier et al. | 604/104 |
| 2002/0022851 A1 | 2/2002 | Kalloo et al. | |
| 2002/0055757 A1 | 5/2002 | Torre et al. | |
| 2002/0072761 A1 | 6/2002 | Abrams et al. | 606/190 |
| 2002/0082621 A1* | 6/2002 | Schurr et al. | 606/151 |
| 2002/0099439 A1 | 7/2002 | Schwartz et al. | |
| 2002/0183767 A1 | 12/2002 | Adams et al. | |
| 2002/0183768 A1 | 12/2002 | Deem et al. | |
| 2003/0009236 A1 | 1/2003 | Godin | |
| 2003/0040764 A1* | 2/2003 | Adams | 606/170 |
| 2003/0040804 A1 | 2/2003 | Stack et al. | |
| 2003/0040808 A1 | 2/2003 | Stack et al. | |
| 2003/0065359 A1 | 4/2003 | Weller et al. | 606/213 |
| 2003/0093117 A1 | 5/2003 | Saadat | |
| 2003/0109892 A1 | 6/2003 | Deem et al. | 606/151 |
| 2003/0120289 A1 | 6/2003 | McGuckin, Jr. et al. | 606/151 |
| 2003/0132267 A1* | 7/2003 | Adams et al. | 227/176.1 |
| 2003/0158569 A1 | 8/2003 | Wazne | |
| 2003/0183671 A1* | 10/2003 | Mooradian et al. | 227/175.1 |
| 2003/0191476 A1 | 10/2003 | Smit | |
| 2003/0199989 A1 | 10/2003 | Stack et al. | |
| 2003/0199990 A1 | 10/2003 | Stack et al. | |
| 2003/0199991 A1 | 10/2003 | Stack et al. | |
| 2003/0208209 A1* | 11/2003 | Gambale et al. | 606/144 |
| 2003/0220660 A1 | 11/2003 | Kortenbach et al. | |
| 2004/0006351 A1 | 1/2004 | Gannoe et al. | 606/139 |
| 2004/0024386 A1 | 2/2004 | Deem et al. | |
| 2004/0030347 A1 | 2/2004 | Gannoe et al. | |
| 2004/0044353 A1 | 3/2004 | Gannoe | |
| 2004/0044354 A1 | 3/2004 | Gannoe et al. | |
| 2004/0044357 A1 | 3/2004 | Gannoe et al. | |
| 2004/0044364 A1 | 3/2004 | DeVries et al. | |
| 2004/0082963 A1 | 4/2004 | Gannoe et al. | 606/153 |
| 2004/0088023 A1 | 5/2004 | Imran et al. | |
| 2004/0092892 A1 | 5/2004 | Kagan et al. | 604/264 |
| 2004/0092960 A1* | 5/2004 | Abrams et al. | 606/139 |
| 2004/0092974 A1 | 5/2004 | Gannoe et al. | 606/153 |
| 2004/0093091 A1 | 5/2004 | Gannoe et al. | |
| 2004/0098043 A1 | 5/2004 | Trout | |
| 2004/0107004 A1 | 6/2004 | Levine et al. | |
| 2004/0117031 A1 | 6/2004 | Stack et al. | |
| 2004/0138682 A1* | 7/2004 | Onuki et al. | 606/144 |
| 2004/0138761 A1 | 7/2004 | Stack et al. | |
| 2004/0143342 A1 | 7/2004 | Stack et al. | |
| 2004/0148034 A1 | 7/2004 | Kagan et al. | |
| 2004/0153167 A1 | 8/2004 | Stack et al. | |
| 2004/0158331 A1 | 8/2004 | Stack et al. | |
| 2004/0162568 A1 | 8/2004 | Saadat et al. | |
| 2004/0172141 A1 | 9/2004 | Stack et al. | |
| 2004/0172142 A1 | 9/2004 | Stack et al. | |
| 2004/0186502 A1 | 9/2004 | Sampson et al. | |
| 2004/0210243 A1 | 10/2004 | Gannoe et al. | 606/151 |
| 2004/0215216 A1 | 10/2004 | Gannoe et al. | |
| 2004/0220682 A1 | 11/2004 | Levine et al. | |
| 2004/0225183 A1 | 11/2004 | Michlitsch et al. | 600/106 |
| 2004/0225305 A1 | 11/2004 | Ewers et al. | 606/153 |
| 2004/0236419 A1 | 11/2004 | Milo | |
| 2004/0243152 A1 | 12/2004 | Taylor et al. | |
| 2004/0243223 A1 | 12/2004 | Kraemer et al. | |
| 2004/0267378 A1 | 12/2004 | Gazi et al. | |
| 2005/0004430 A1 | 1/2005 | Lee et al. | |
| 2005/0004681 A1 | 1/2005 | Stack et al. | |
| 2005/0033326 A1 | 2/2005 | Briganti et al. | |
| 2005/0033345 A1 | 2/2005 | DeLegge | |
| 2005/0049718 A1 | 3/2005 | Dann et al. | |
| 2005/0075654 A1 | 4/2005 | Kelleher | |
| 2005/0080444 A1 | 4/2005 | Kraemer et al. | |
| 2005/0085787 A1 | 4/2005 | Laufer et al. | 604/500 |
| 2005/0096673 A1 | 5/2005 | Stack et al. | 606/151 |
| 2005/0096750 A1 | 5/2005 | Kagan et al. | |
| 2005/0149114 A1 | 7/2005 | Cartledge et al. | |
| 2005/0159769 A1 | 7/2005 | Alverdy | |
| 2005/0177181 A1 | 8/2005 | Kagan et al. | |
| 2005/0183732 A1 | 8/2005 | Edwards | |
| 2005/0192599 A1 | 9/2005 | Demarais | 606/151 |
| 2005/0192615 A1 | 9/2005 | Torre et al. | |
| 2005/0203547 A1* | 9/2005 | Weller et al. | 606/139 |
| 2005/0203548 A1* | 9/2005 | Weller et al. | 606/139 |
| 2005/0216040 A1 | 9/2005 | Gertner et al. | |
| 2005/0216042 A1 | 9/2005 | Gertner | |
| 2005/0240279 A1 | 10/2005 | Kagan et al. | |
| 2005/0247320 A1 | 11/2005 | Stack et al. | |
| 2005/0250980 A1 | 11/2005 | Swanstrom et al. | |
| 2005/0251158 A1 | 11/2005 | Sadat et al. | |
| 2005/0251162 A1 | 11/2005 | Rothe et al. | 606/153 |
| 2005/0256533 A1 | 11/2005 | Roth et al. | 606/167 |
| 2005/0256587 A1 | 11/2005 | Egan | |
| 2005/0261712 A1 | 11/2005 | Balbierz et al. | |
| 2005/0267405 A1 | 12/2005 | Shah | |
| 2005/0267499 A1 | 12/2005 | Stack et al. | |
| 2005/0267595 A1 | 12/2005 | Chen et al. | |
| 2005/0267596 A1 | 12/2005 | Chen et al. | |
| 2005/0273060 A1 | 12/2005 | Levy et al. | |
| 2006/0015006 A1 | 1/2006 | Laurence et al. | |
| 2006/0020278 A1 | 1/2006 | Burnette et al. | |
| 2006/0058829 A1 | 3/2006 | Sampson et al. | |
| 2006/0129094 A1 | 6/2006 | Shah | |
| 2006/0151568 A1 | 7/2006 | Weller et al. | 227/175.1 |
| 2006/0155259 A1 | 7/2006 | MacLay | |
| 2006/0155311 A1 | 7/2006 | Hashiba et al. | |
| 2006/0178560 A1 | 8/2006 | Saadat et al. | |
| 2006/0178691 A1 | 8/2006 | Binmoeller | |
| 2006/0195139 A1 | 8/2006 | Gertner | |
| 2006/0271076 A1 | 11/2006 | Weller et al. | 606/153 |
| 2006/0282095 A1* | 12/2006 | Stokes et al. | 606/144 |
| 2007/0032800 A1 | 2/2007 | Ortiz et al. | 606/148 |
| 2007/0043384 A1 | 2/2007 | Ortiz et al. | 606/142 |
| 2007/0055292 A1 | 3/2007 | Ortiz et al. | 606/139 |
| 2007/0175488 A1 | 8/2007 | Cox et al. | 128/898 |
| 2007/0191870 A1 | 8/2007 | Baker et al. | 606/153 |
| 2007/0191871 A1 | 8/2007 | Baker et al. | 606/153 |

FOREIGN PATENT DOCUMENTS

| | | |
|---|---|---|
| EP | 1492478 | 1/2005 |
| EP | 1 602 336 A2 | 12/2005 |
| EP | 1602336 | 12/2005 |
| FR | 2768324 A1 | 3/1999 |

(56) References Cited

FOREIGN PATENT DOCUMENTS

| | | | |
|---|---|---|---|
| JP | 09-168597 | 6/1997 | |
| WO | WO 91/01117 | 2/1991 | |
| WO | WO 97/47231 A2 | 12/1997 | |
| WO | WO 00/12027 | 3/2000 | |
| WO | WO 00/32137 | 6/2000 | |
| WO | WO 00/78227 | 12/2000 | A61B 17/064 |
| WO | WO 01/41671 | 6/2001 | |
| WO | WO 01/45485 | 6/2001 | |
| WO | WO 01/49359 | 7/2001 | |
| WO | WO 01/66018 | 9/2001 | A61B 17/00 |
| WO | WO 01/85034 | 11/2001 | A61B 17/072 |
| WO | WO 01/89393 | 11/2001 | A61B 17/10 |
| WO | WO 02/060328 | 8/2002 | A61B 17/072 |
| WO | WO 03/017882 | 3/2003 | |
| WO | WO 03/086246 | 10/2003 | |
| WO | WO 03/086247 | 10/2003 | |
| WO | WO 03/090633 | 11/2003 | |
| WO | WO 03/094784 | 11/2003 | |
| WO | WO 03/094785 | 11/2003 | |
| WO | WO 03/099137 | 12/2003 | |
| WO | WO 03/099137 A2 | 12/2003 | |
| WO | WO 2004/019765 | 3/2004 | |
| WO | WO 2004/019787 | 3/2004 | |
| WO | WO 2004/032760 | 4/2004 | |
| WO | WO 2004/032760 A2 | 4/2004 | |
| WO | WO 2004/037064 | 5/2004 | |
| WO | WO 2004/041133 | 5/2004 | |
| WO | WO 2004/064680 | 8/2004 | |
| WO | WO 2004/064685 | 8/2004 | |
| WO | WO 2004/080336 | 9/2004 | |
| WO | WO 2004/110285 | 12/2004 | |
| WO | WO 2004/110285 A1 | 12/2004 | |
| WO | WO 2005/037152 | 4/2005 | |
| WO | WO 2005/037152 A1 | 4/2005 | |
| WO | WO 2005/079673 | 9/2005 | |
| WO | WO 2005/079673 A2 | 9/2005 | A61B 17/00 |
| WO | WO 2005/096991 | 10/2005 | |
| WO | WO 2005/096991 A1 | 10/2005 | |
| WO | WO 2005/105003 | 11/2005 | |
| WO | WO 2006/016894 | 2/2006 | |
| WO | WO 2006/016894 A1 | 2/2006 | |
| WO | WO 2006/055365 | 5/2006 | |
| WO | WO 2006/055365 A2 | 5/2006 | |
| WO | WO 2006/127593 | 11/2006 | |
| WO | WO 2007/041598 | 4/2007 | |
| WO | WO 2007/041598 A1 | 4/2007 | |

OTHER PUBLICATIONS

Stecco, K. et al., "Safety of a Gastric Restrictive Implant in a Canine Model", Stecco Group, San Jose and Barosnese, Inc., Redwood City, California (2004).
International Search Report from PCT Patent Application No. PCT/US2002/027177 mailed Feb. 14, 2003.
International Search Report from PCT Patent Application No. PCT/US2003/004378 mailed Aug. 13, 2003.
International Search Report from PCT Patent Application No. PCT/US2003/033605 mailed Mar. 29, 2004.
International Search Report from PCT Patent Application No. PCT/US2003/033606 mailed Mar. 29, 2004.
International Search Report from PCT Patent Application No. PCT/US2003/004449 mailed Aug. 13, 2003.
International Search Report from PCT Patent Application No. PCT/US2004/006695 mailed Sep. 8, 2004.
International Search Report from PCT Patent Application No. PCT/US2004/033007 mailed Feb. 9, 2005.
International Search Report from PCT Patent Application No. PCT/US2005/014372 mailed Jul. 28, 2005.
International Search Report from PCT Patent Application No. PCT/US2006/019727 mailed Apr. 19, 2007.
International Search Report from PCT Patent Application No. PCT/US2006/038684 mailed Feb. 14, 2007.
Felsher, et al., "Mucosal apposition in endoscopic suturing", Gastrointestinal Endoscopy, vol. 58, No. 6, pp. 867-870, (2003).
Stecco, et al., "Trans-oral plication formation and gastric implant placement in a canine model", Stecco Group, San Jose and Barosense, Inc., Redwood City, CA (2004).
Stecco, et al., "Safety of a gastric restrictive implant in a canine model", Stecco Group, San Jose and Barosense, Inc., Redwood City, CA (2004).

* cited by examiner

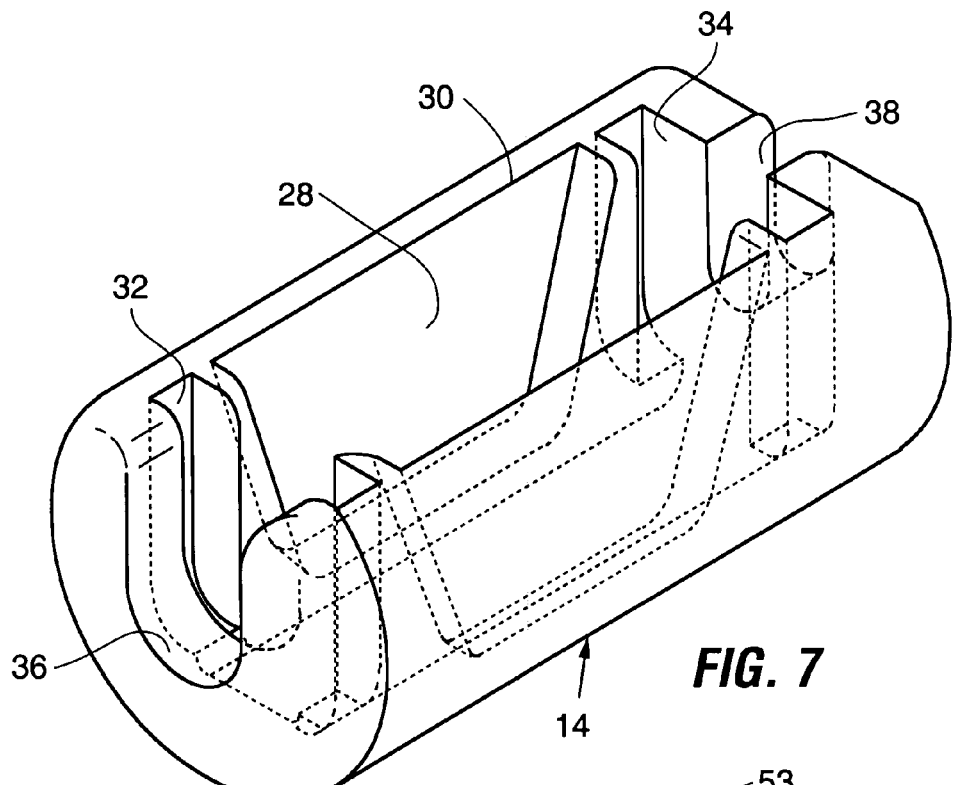
FIG. 7
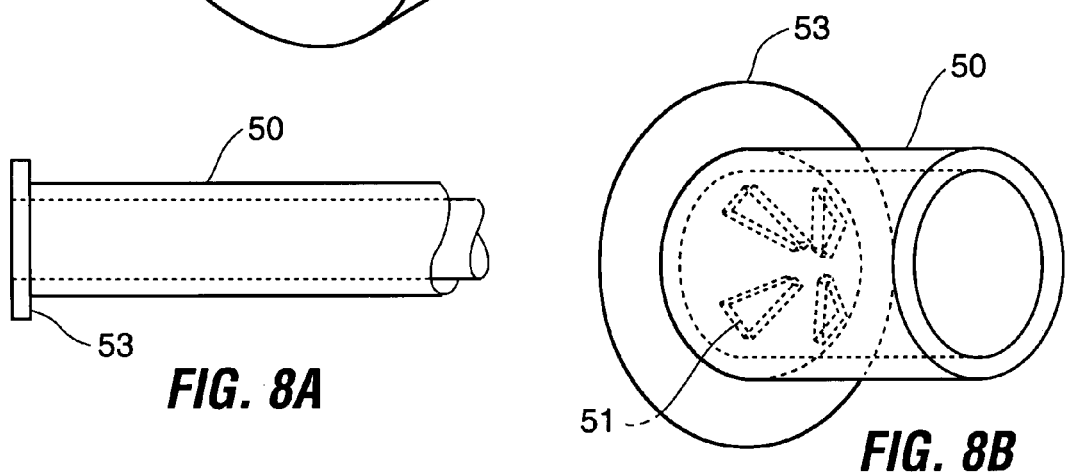
FIG. 8A
FIG. 8B
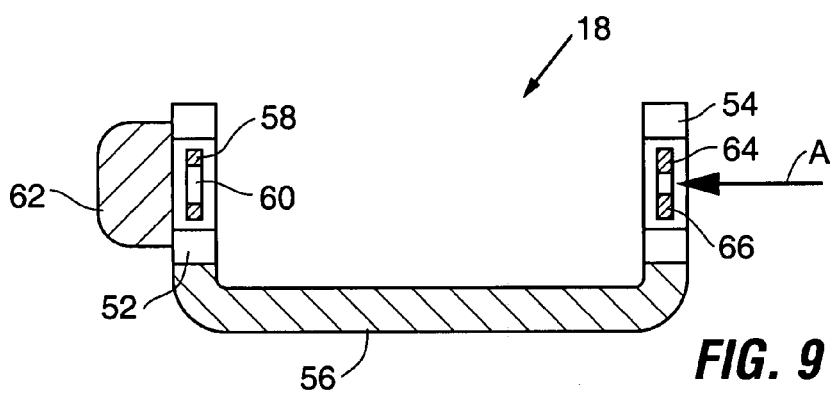
FIG. 9

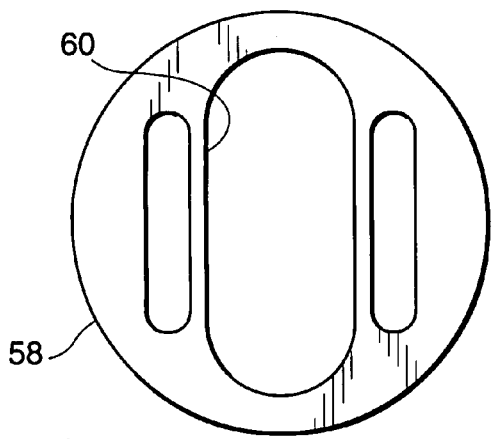
FIG. 10
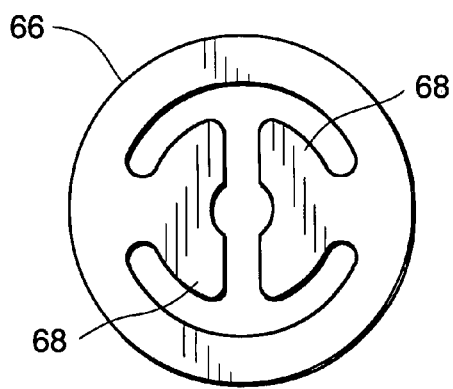
FIG. 11A
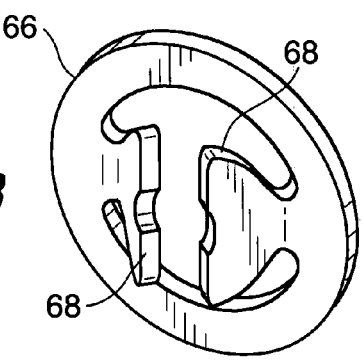
FIG. 11B
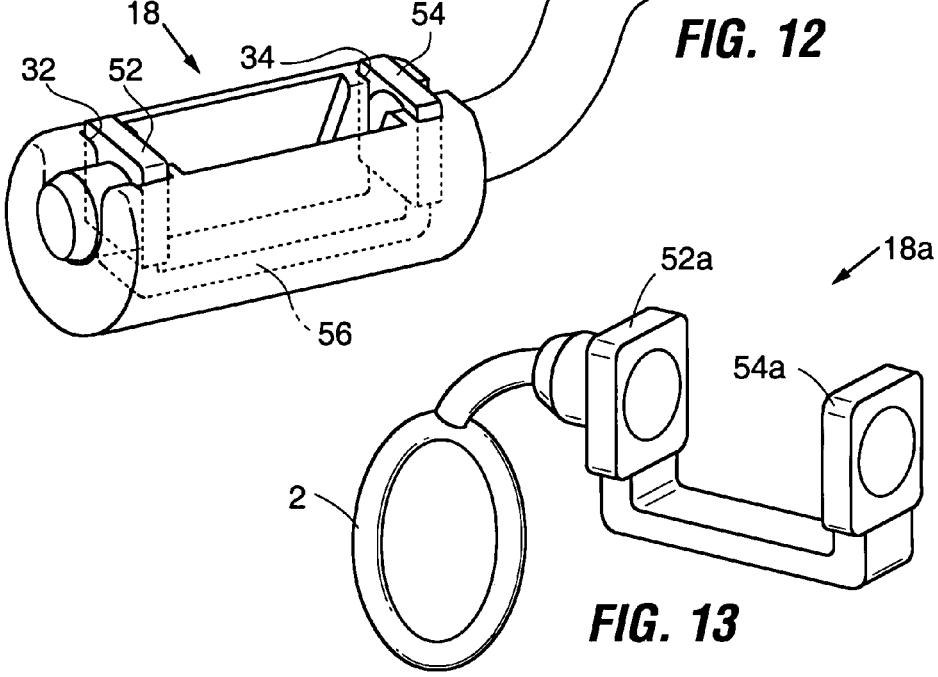
FIG. 12
FIG. 13

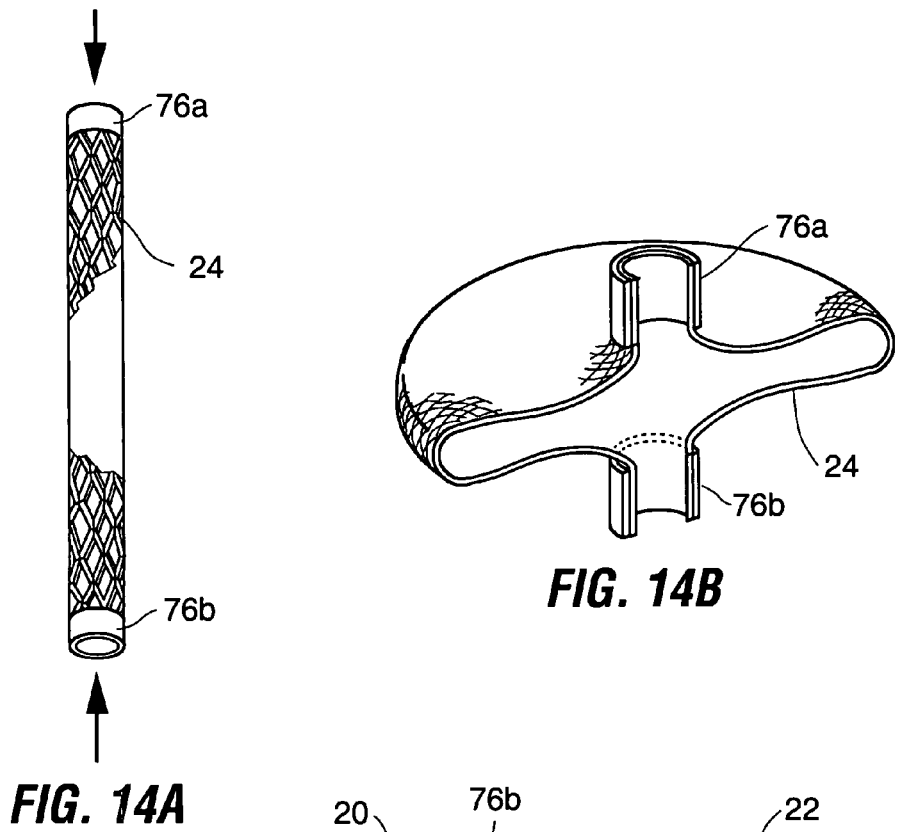
FIG. 14A
FIG. 14B
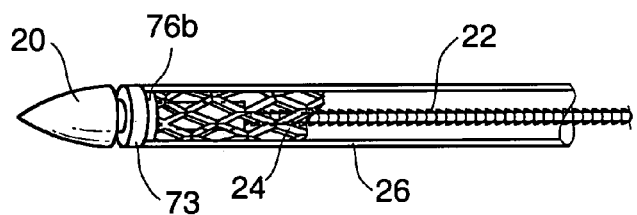
FIG. 15A
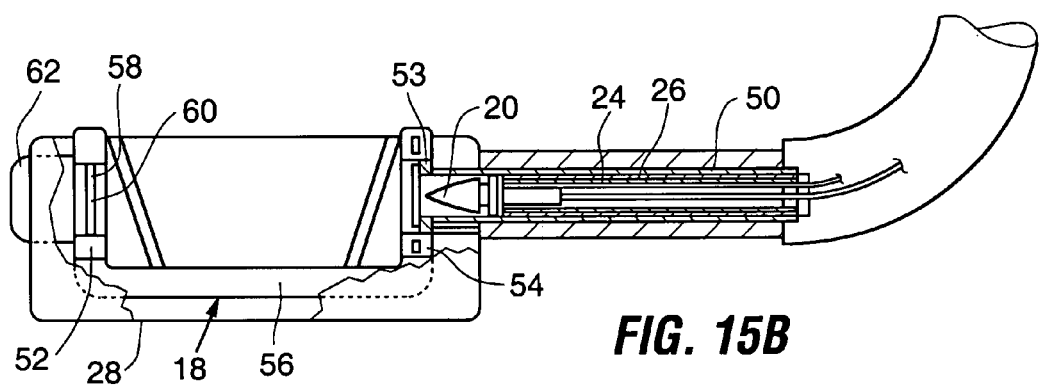
FIG. 15B

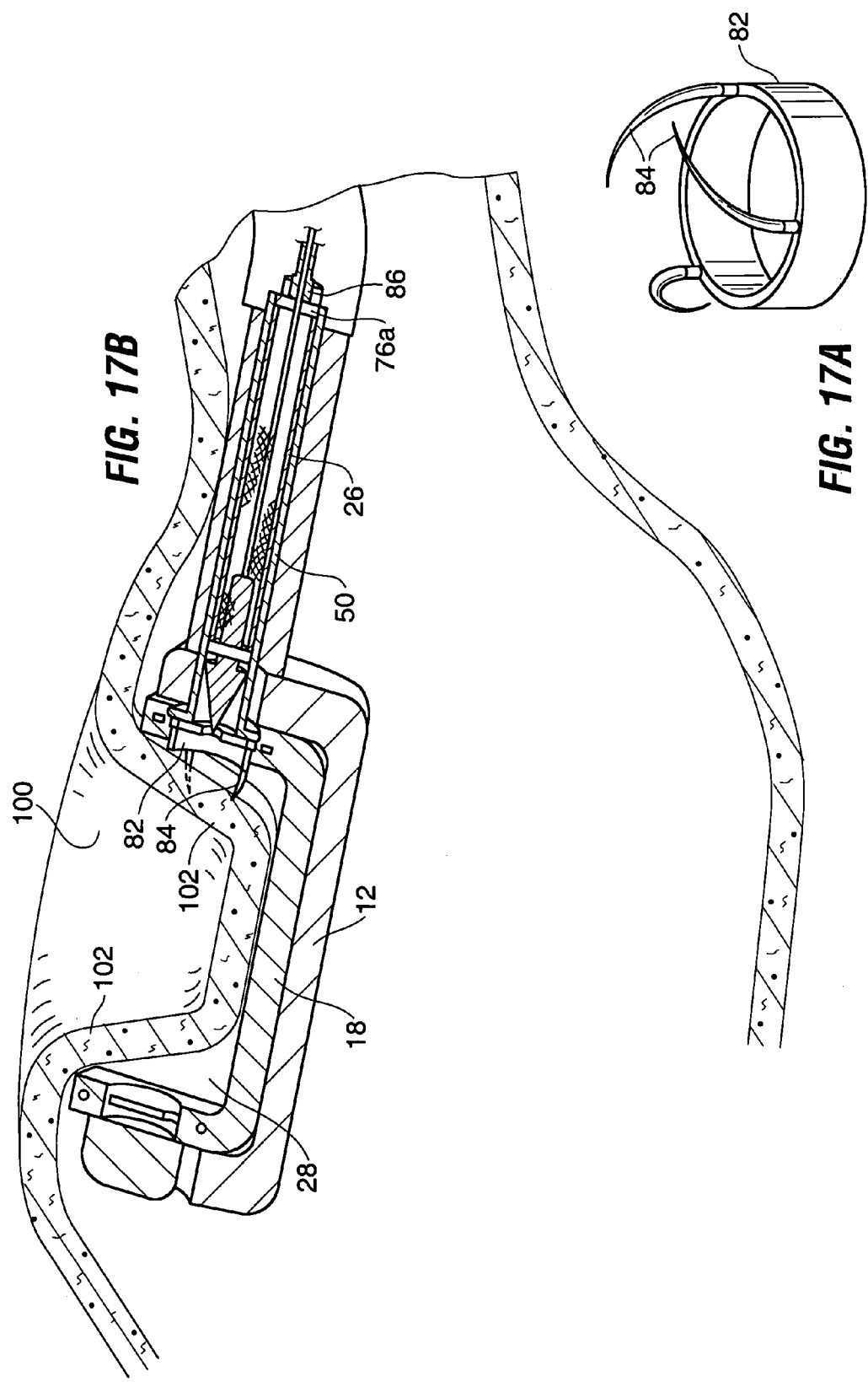

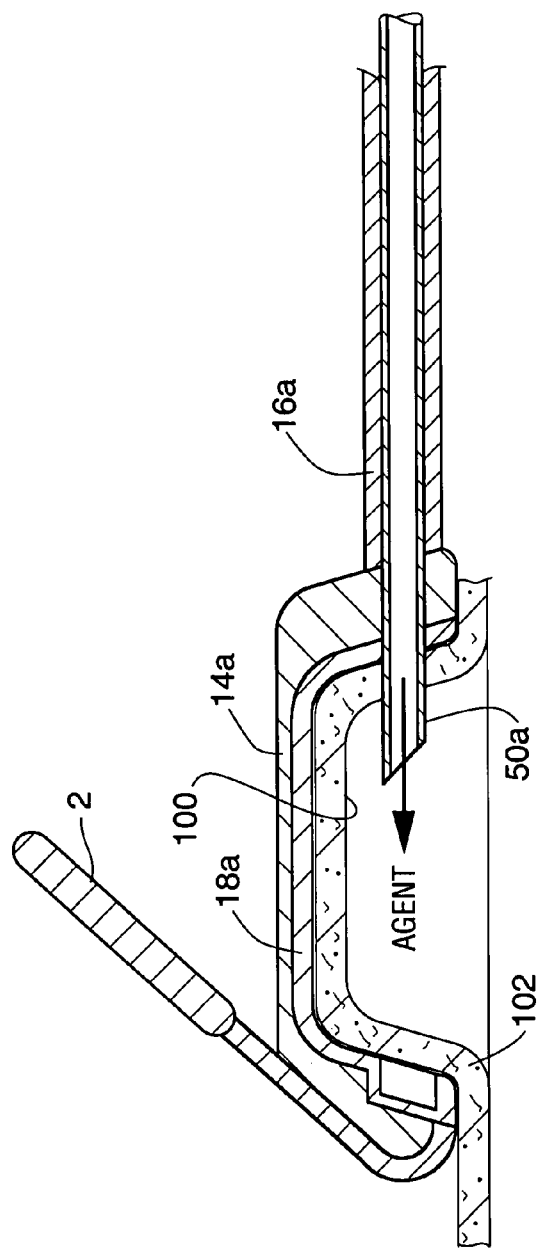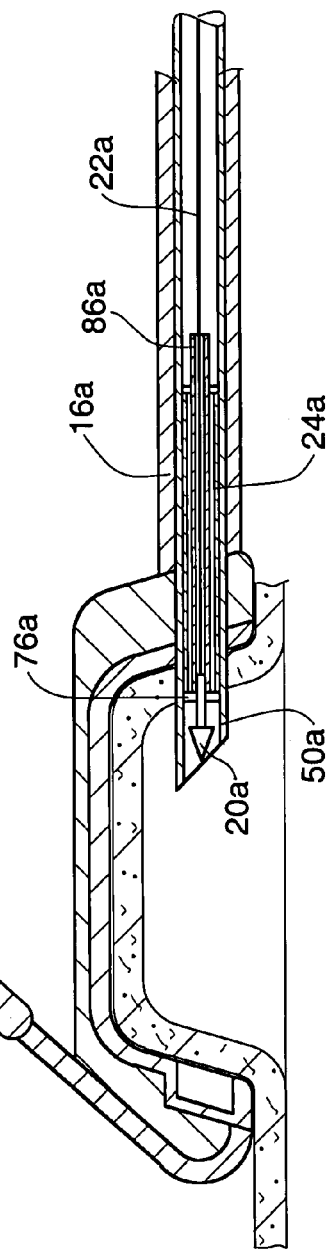

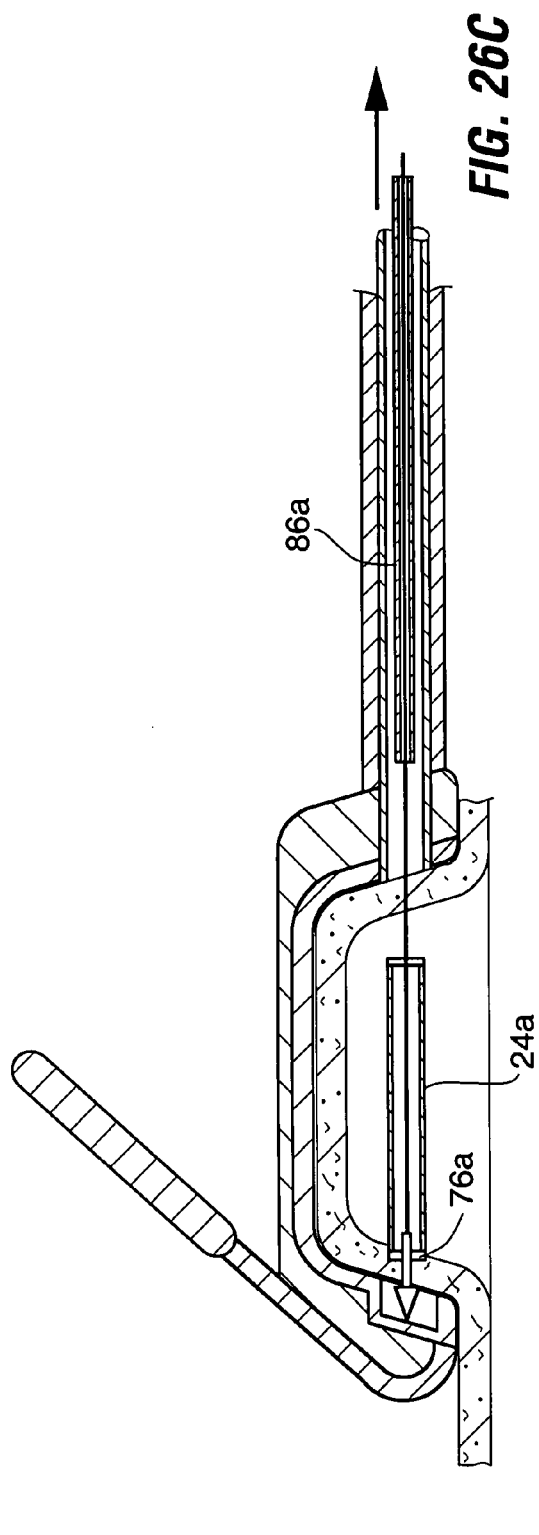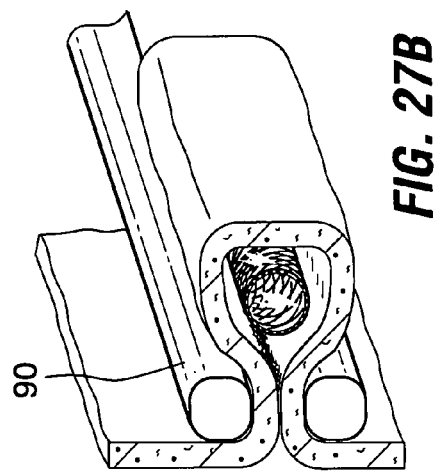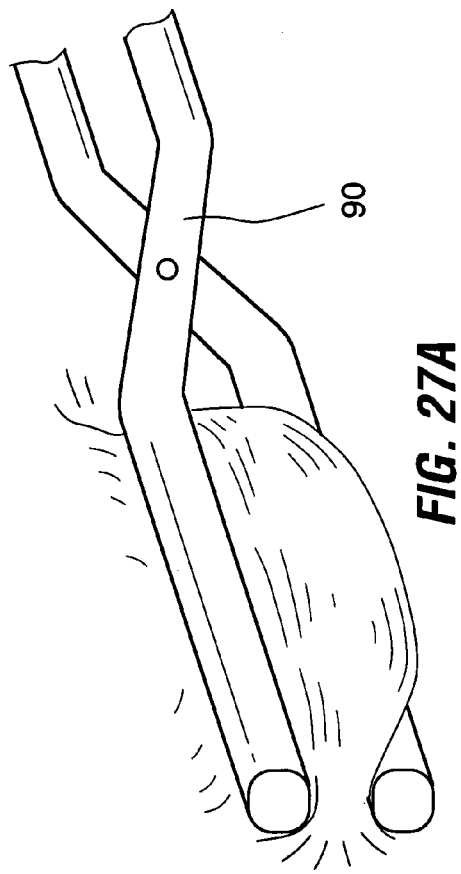

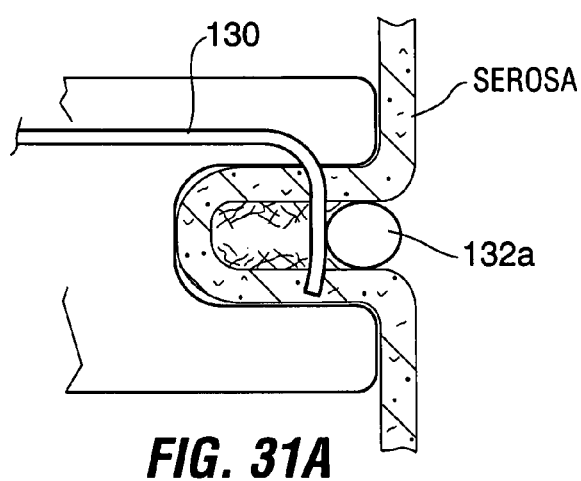
FIG. 31A
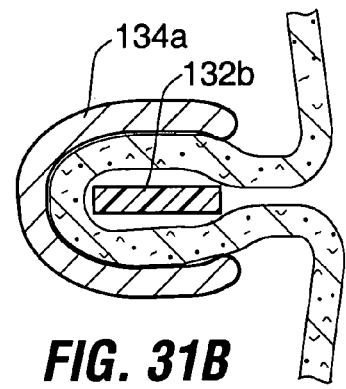
FIG. 31B
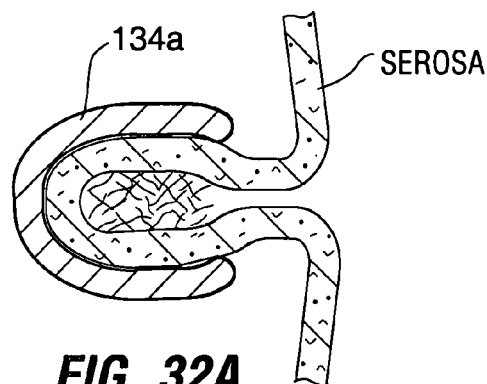
FIG. 32A
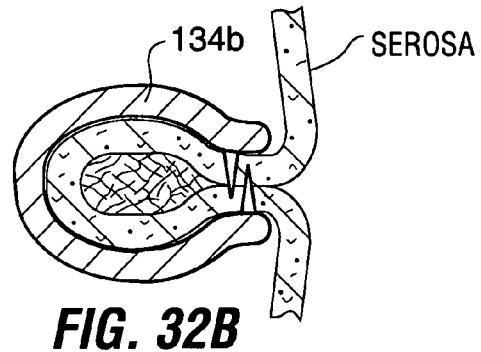
FIG. 32B
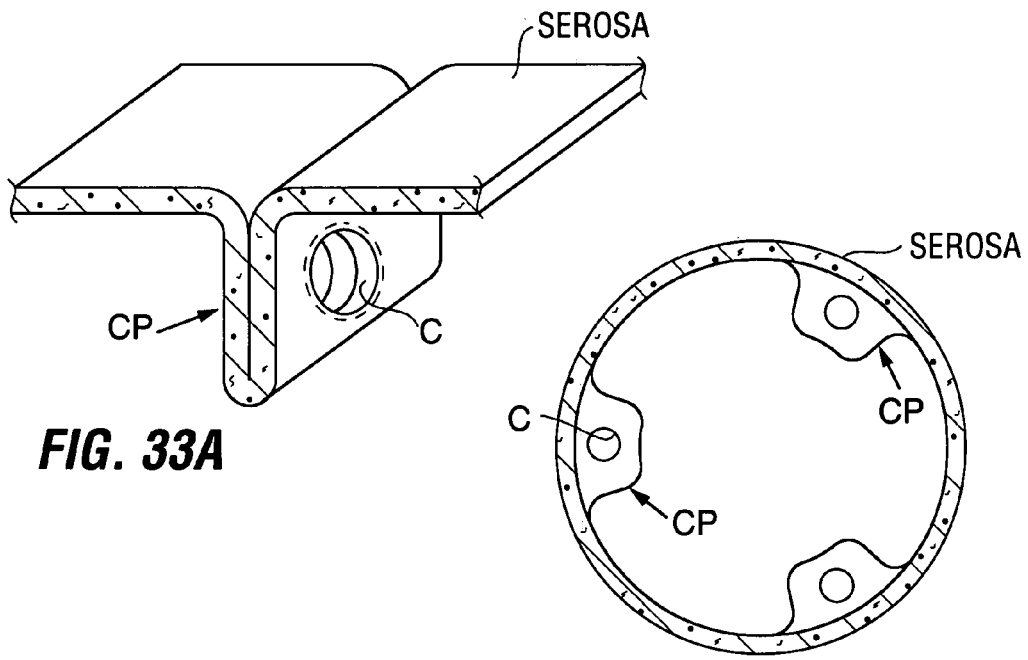
FIG. 33A
FIG. 33B

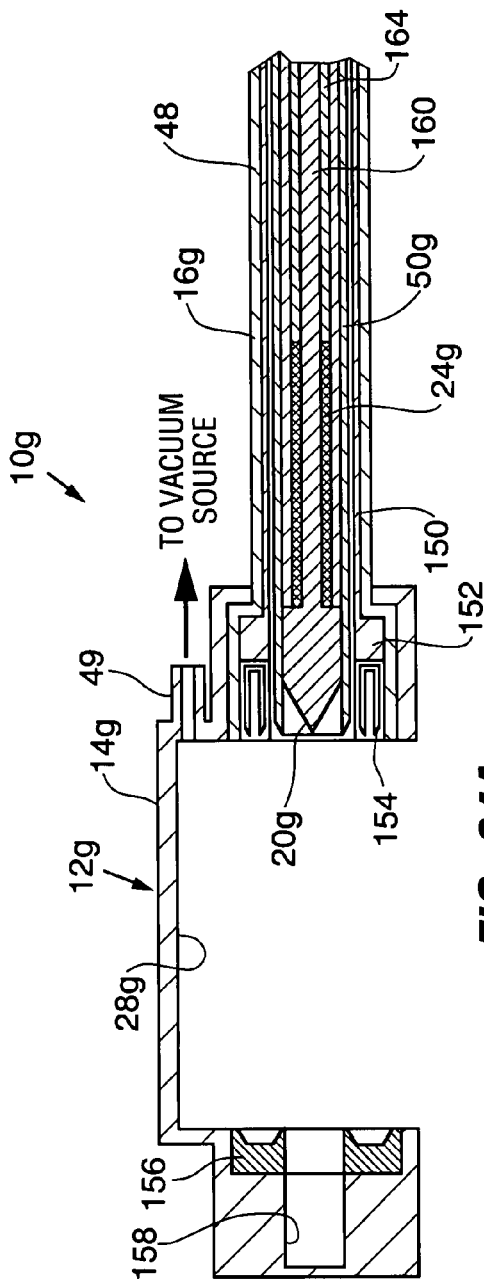
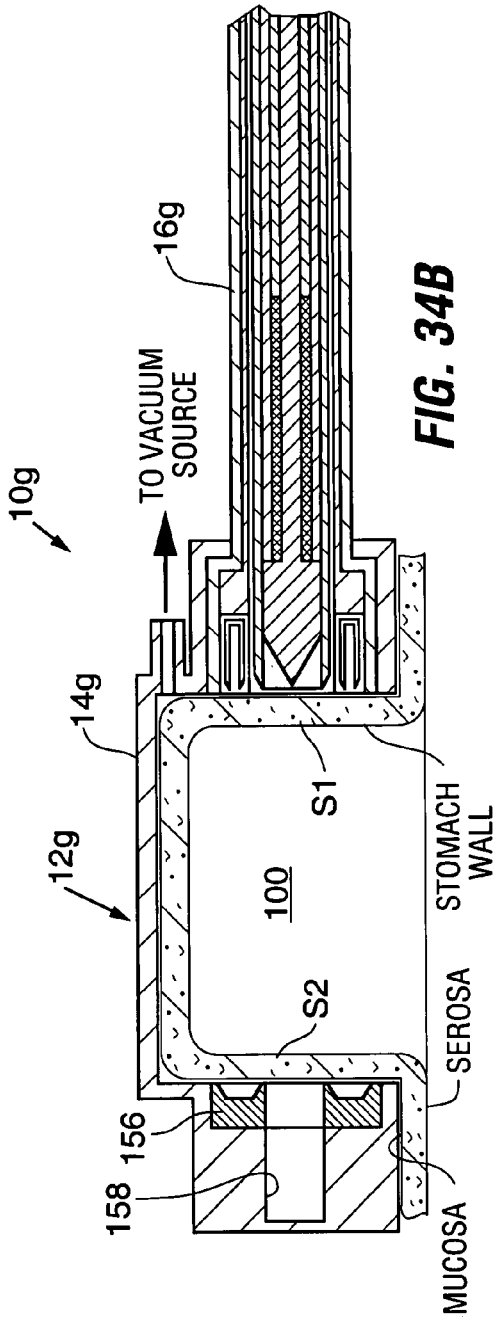

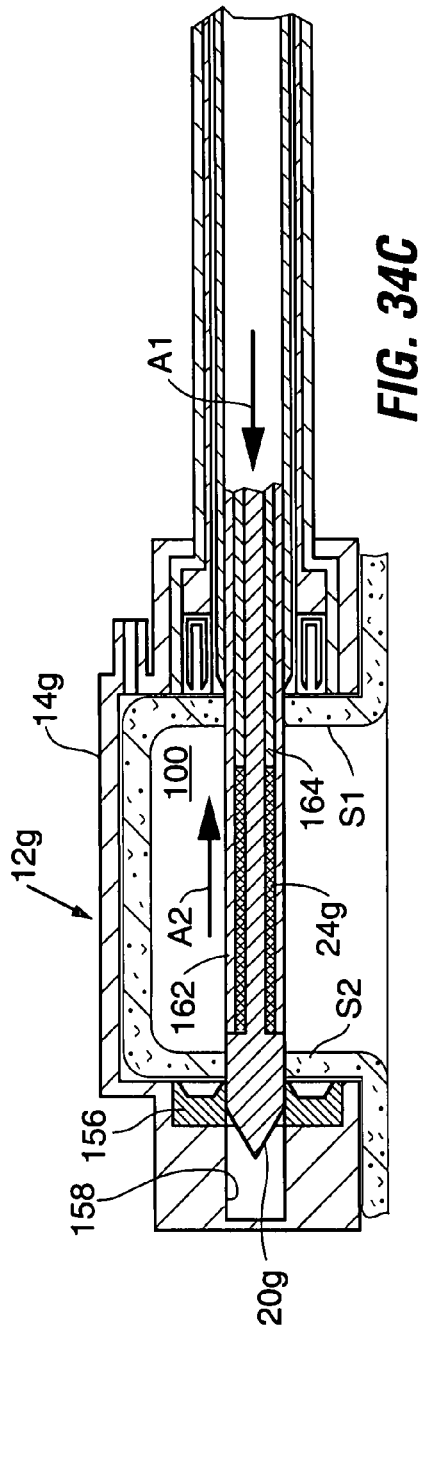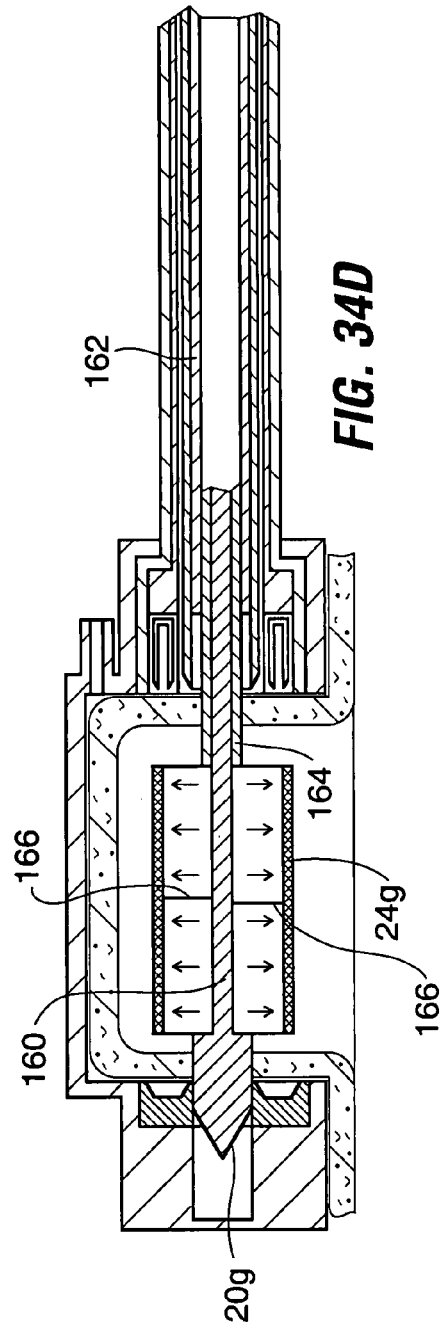

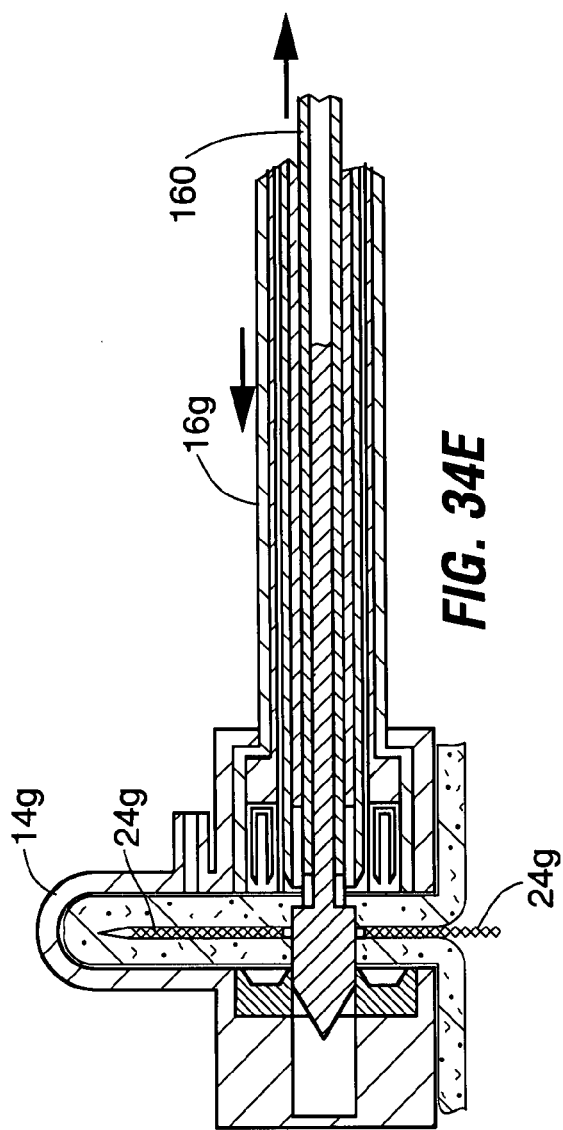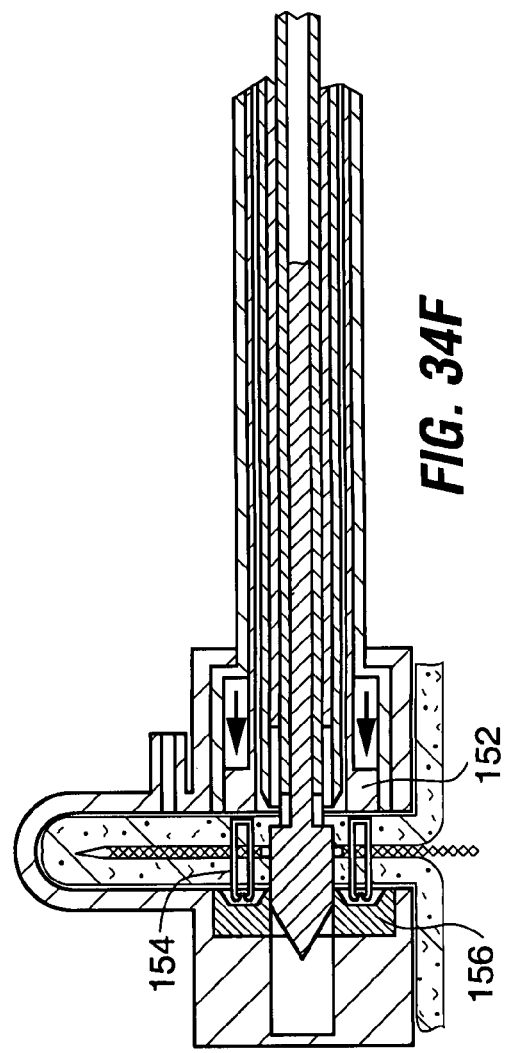

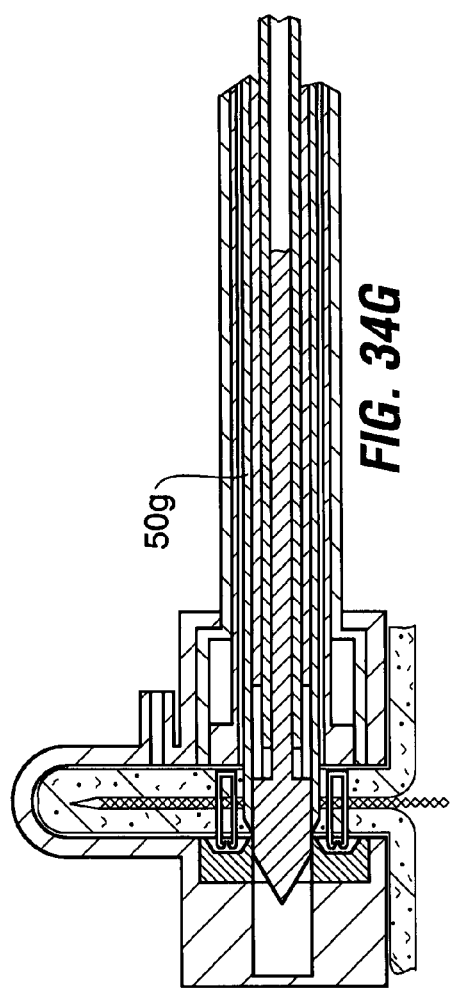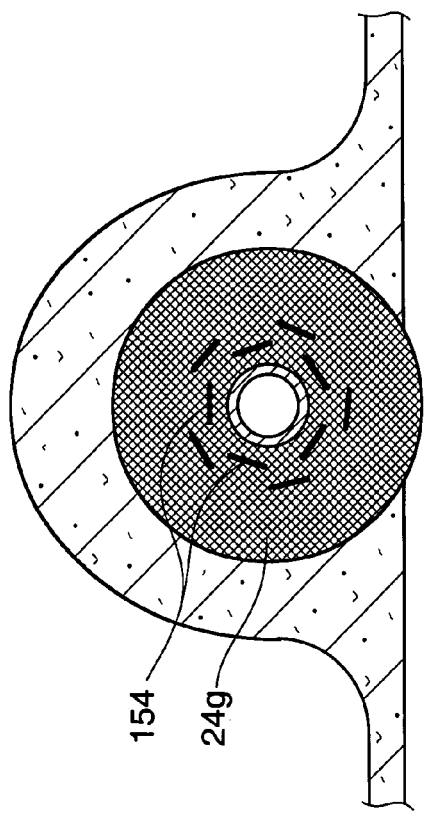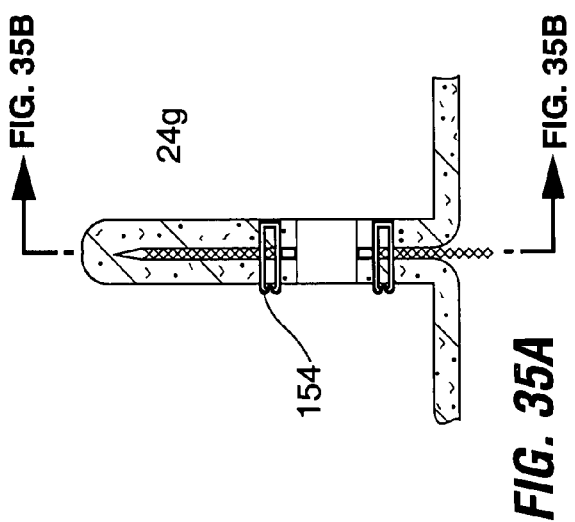

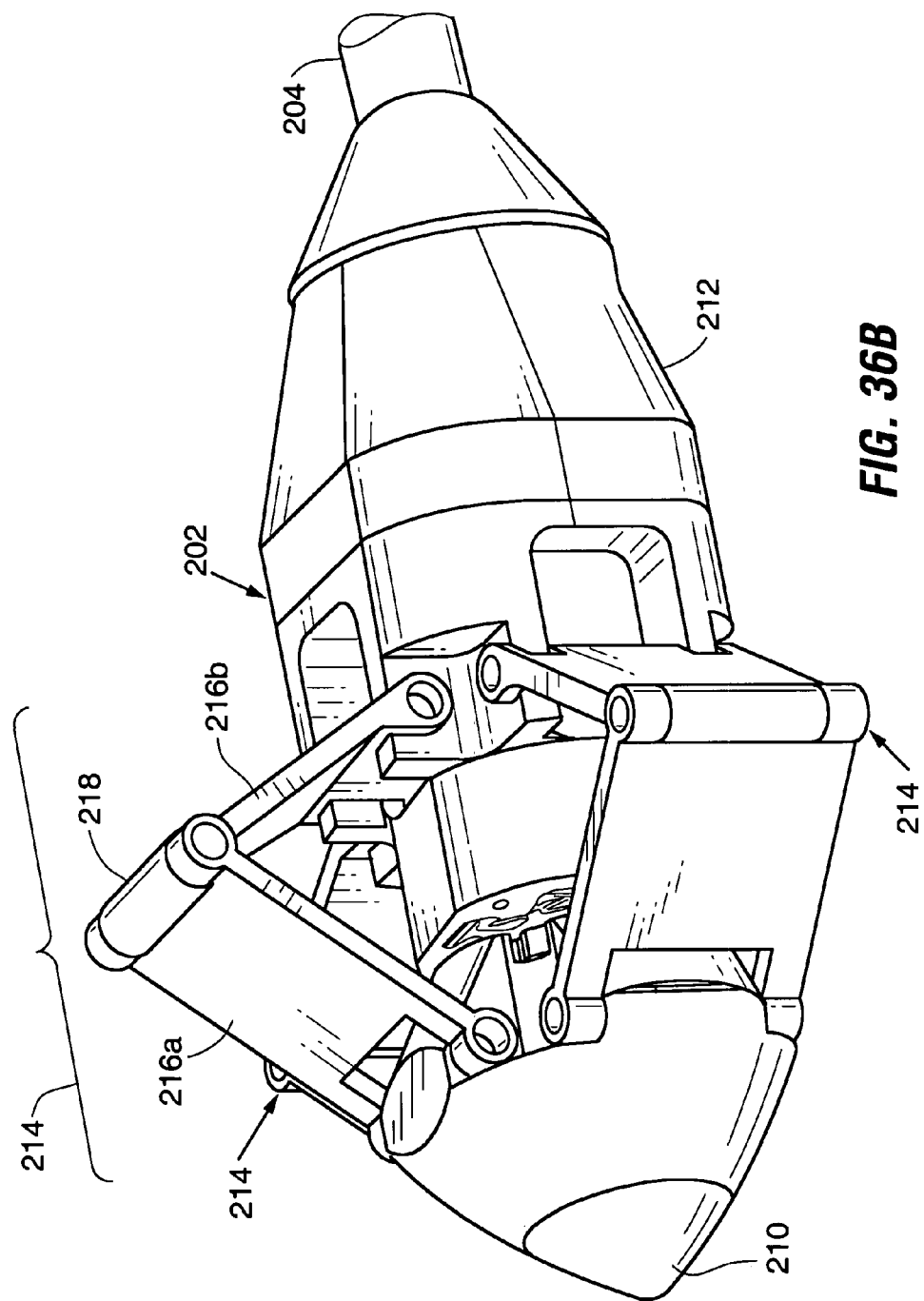

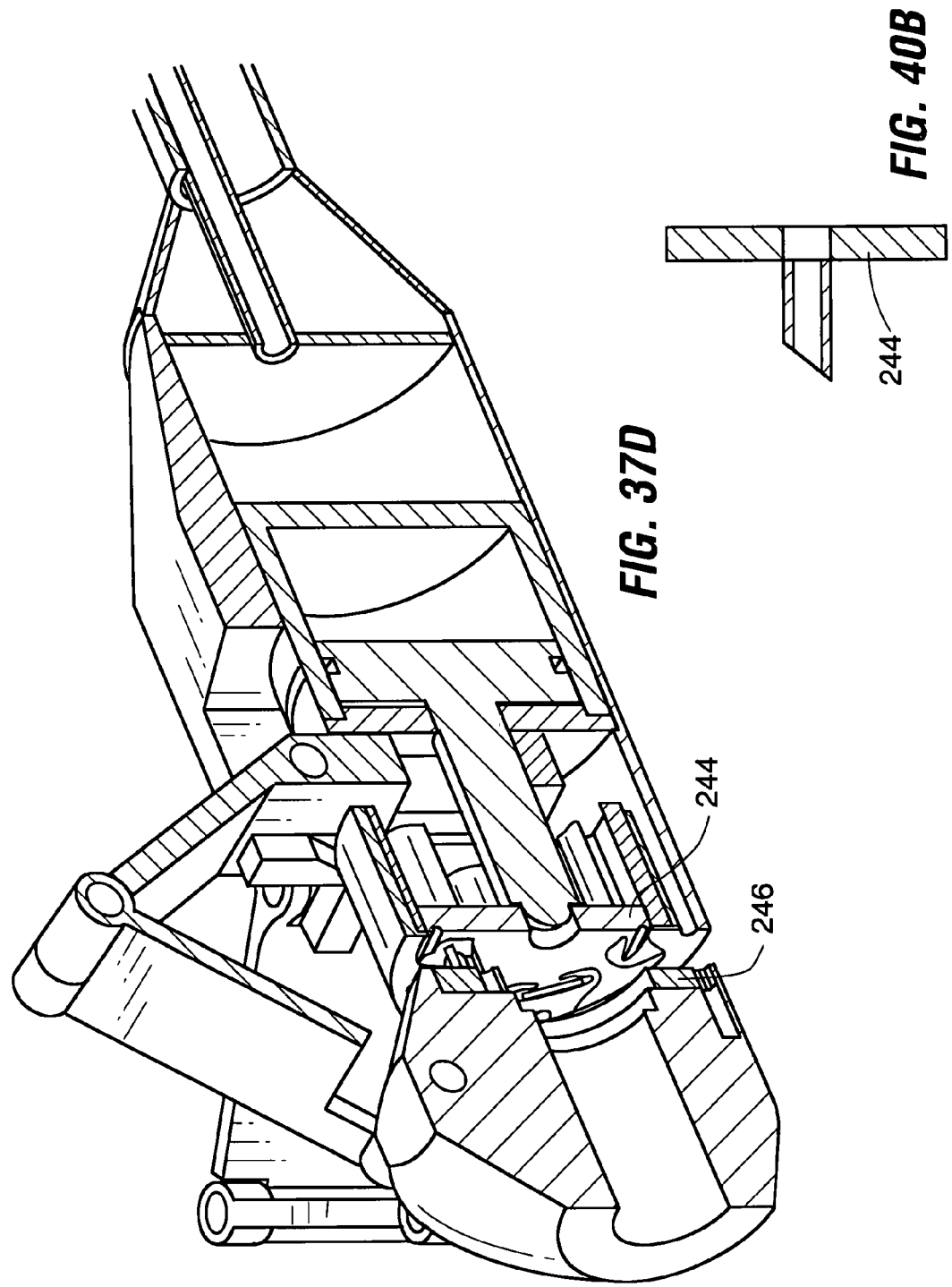

ions may themselves be sufficient to provide the necessary treatment. For example, the plications may be used to reduce stomach volume or form a flow restriction within the stomach.

ENDOSCOPIC PLICATION DEVICES AND METHODS

PRIORITY

This application claims the benefit of U.S. Provisional Application No. 60/723,160, filed Oct. 3, 2005; U.S. Provisional Application No. 60/754,417, filed Dec. 28, 2005; and U.S. Provisional Application No. 60/825,534, filed Sep. 13, 2006.

FIELD OF THE INVENTION

The present invention relates generally to the field of systems and methods for performing endoscopic surgery, and specifically to systems and methods for endoscopic plication of tissue within body cavities.

BACKGROUND OF THE INVENTION

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

FIG. 1B illustrates the tissue layers forming the stomach wall. The outermost layer is the serosal layer or "serosa" S and the innermost layer, lining the stomach interior, is the mucosal layer or "mucosa" MUC. The submucosa SM and the multi-layer muscularis M lie between the mucosa and the serosa.

Several prior applications sharing inventors with the present application, including International Application No. WO 2005/037152 having an international filing date of Oct. 8, 2004 and U.S. application Ser. No. 11/439,461, filed May 23, 2006 (both incorporated herein by reference) describe methods according to which medical implants are coupled to tissue structures formed within the stomach. According to these applications, devices for inducing weight loss (e.g. by restricting and/or obstructing flow of food into the stomach, and/or by occupying a portion of the stomach volume) may be coupled to tissue tunnels or plications P (FIG. 2) formed from stomach tissue.

For example, U.S. application Ser. No. 11/439,461 (incorporated herein by reference in its entirety), describes a restrictive and/or obstructive implant system for inducing weight loss. In one embodiment, flexible loops 2 (FIG. 3) are coupled to tissue plications P (FIG. 2) formed in the gastroesophageal junction region of the stomach. An implant, such as a flow restrictive and/or obstructive implant 4 (FIG. 4), is passed through the loops 2 and thus retained in the stomach as shown in FIG. 5.

In other instances, tissue plications may themselves be sufficient to provide the necessary treatment. For example, the plications may be used to reduce stomach volume or form a flow restriction within the stomach.

Other types of implants may be coupled to such plications or other tissue structures for a variety of purposes. These implants include, but are not limited to prosthetic valves for the treatment of gastro-esophageal reflux disease, gastric stimulators, pH monitors and drug eluting devices that release drugs, biologics or cells into the stomach or elsewhere in the GI tract. Such drug eluting devices might include those which release leptin (a hormone which creates feelings of satiety), Ghrelin (a hormone which creates feelings of hunger), octreotide (which reduces Ghrelin levels and thus reduces hunger), Insulin, chemotherapeutic agents, natural biologics (e.g. growth factor, cytokines) which aid in post surgery trauma, ulcers, lacerations etc. Still other implants might be of a type which might provide a platform to which specific cell types can adhere, grow and provide biologically-active gene products to the GI tract, and/or a platform for radiation sources that can provide a local source of radiation for therapeutic purposes, or provide a platform whereby diagnostic ligands are immobilized and used to sample the GI tract for evidence of specific normal or pathological conditions, or provide an anchor point for imaging the GI tract via cameras and other image collecting devices.

The prior applications listed above, address the desirability of forming tissue plications, pockets or tunnels in a way that regions of serosal tissue (i.e. the tissue on the exterior surface of the stomach) are retained in contact with one another. Over time, adhesions formed between the opposed serosal layers create strong bonds that can facilitate retention of the plication/pocket/tissue over extended durations, despite the forces imparted on them by stomach movement and implanted devices. More durable plications can be created by placing any of a number of materials and/or substances (i.e. injectable sclerosing agents) between the serosal surfaces prior to plicating the serosal surfaces together. One example of material suitable for this purpose is polypropolyene mesh, commonly used for hernia repair, which when inserted in the plication fold provides a durable anchoring position within the GI tract.

Regardless of the application for which a plication is being formed, it is highly desirable to form that plication using steps carried out from within the stomach using instruments passed down the esophagus, rather than using more invasive surgical or laparoscopic methods. The present application describes endoscopic plicators which may be passed transorally into the stomach and used to form serosal-to-serosal plications in a stomach wall.

BRIEF DESCRIPTION OF THE DRAWINGS

FIG. 7 is a perspective view of the vacuum head of the system of FIG. 6.

FIG. 8A is a side elevation view of the cannula of the system of FIG. 6.

FIG. 8B is a perspective view of the distal end of the cannula of FIG. 8A.

FIG. 9 is a cross-sectional side view of an anchor of the system of FIG. 6.

FIG. 10 is a plan view of the catch of the anchor of FIG. 9.

FIG. 11A is a plan view of the spring element of the anchor of FIG. 9.

FIG. 11B is a perspective view of the spring element of FIG. 11A, showing the spring tabs in the opened position.

FIG. 12 is a perspective view of the vacuum head of FIG. 7, showing the anchor of FIG. 9 positioned within the vacuum head.

FIG. 13 is a perspective view of the anchor of FIG. 9, which includes a loop of the type shown in FIG. 3.

FIG. 14A is a perspective view of the mesh tube of the system of FIG. 6.

FIG. 14B is cross-sectional perspective view showing the mesh tube of FIG. 14A in the compressed orientation.

FIG. 15A is a side elevation view showing the tip, cable, mesh tube, and sheath of FIG. 6 following assembly.

FIG. 15B is a side elevation view of the plicator of FIG. 6 assembled for use.

FIG. 17A is a perspective view of a barbed stabilizing cuff.

FIG. 17B is a perspective view similar to FIG. 16B, showing use of the barbed stabilizing cuff of FIG. 17A to stabilize tissue within the pocket.

FIGS. 23A and 23B are cross-sectional side views. FIGS. 24A and 24B are perspective views taken from within the stomach.

FIGS. 26A through 26C are cross-sectional side views of a plication system and a stomach wall, illustrating an alternative method in which a sclerosing agent is injected into the serosal pocket prior to advancement of the tip element.

FIGS. 27A and 27B are cross-section views illustrating a method for sealing sclerosing agent within the serosal pocket using a clamp.

FIGS. 28 and 29, in which FIG. 28 is a perspective view and FIG. 29 is a cross-section view of a distal end of a plication system and a portion of the stomach wall, illustrate methods for sealing sclerosing agent within the serosal pocket using the vacuum head.

FIGS. 31A and 31B illustrate alternate place holding elements for use in the method of FIGS. 30A-30D.

FIGS. 32A and 32B illustrate the use of clamps to retain plications formed using the FIG. 30A-30D method during healing of the plications.

FIG. 33A is a perspective view of a serosal plication having a cutout formed through the tissue. FIG. 33B is a cross-section view of a stomach illustrating three serosal plications of the type shown in FIG. 33A.

FIG. 34A is a cross-sectional side view of a second preferred embodiment of a plication system.

FIGS. 34B-34G are a sequence of cross-sectional side views illustrating formation of a plication of the type shown in FIG. 33A using the system of FIG. 34A.

FIG. 35A is a cross-section side view of the plication formed in accordance with the method of FIGS. 34A-34G.

FIG. 35B is a cross-sectional plan view taken along the plane designated 35B-35B in FIG. 35A.

FIG. 36B is a perspective view similar to FIG. 36A showing the plication head in the expanded position. The shroud is not shown to allow clear viewing of the underlying components.

FIGS. 37A through 37D are a sequence of cross-sectional perspective views of the plication head of FIGS. 36A and 36B, illustrating a method of using the plication head. The shroud is not shown to allow clear viewing of the underlying components.

FIG. 40B is a cross-sectional side view of the staple driver of the embodiment of FIGS. 36A-37D.

FIGS. 46A and 46B are plan views of a tissue plication, in which FIG. 46A shows the side of the plication positioned on the staple cartridge side of the plicator, and FIG. 46B shows the side of the plication position on the anvil side of the plicator.

DETAILED DESCRIPTION OF THE DRAWINGS

The present application describes endoscopic plicators which may be passed transorally into the stomach and used to plicate stomach tissue by engaging tissue from inside of the stomach and drawing it inwardly. In the disclosed embodiments, the tissue is drawn inwardly into a vacuum chamber, although tissue may be drawn inwardly using other components that do not involve the use of a vacuum. When a portion the stomach wall is drawn inwardly, sections of serosal tissue on the exterior of the stomach are positioned facing one another. The disclosed plicators allow the opposed sections of tissue to be moved into contact with one another, and preferably deliver sutures, staples or other means for maintaining contact between the tissue sections at least until serosal bonds form between them. Each of these steps may be performed wholly from the inside of the stomach and thus can eliminate the need for any surgical or laparoscopic intervention. After one or more plications is formed, medical devices (including, but not limited to any of the types listed above) may be coupled to the plication(s) for retention within the stomach.

Certain of the disclosed plicators pass a mesh element and/or a quantity of sclerosing agent through the stomach wall such that it is disposed between the opposed regions of serosal tissue thus enhancing serosal bonding. Some embodiments include a feature that forms a hole in a plication using the plication device, so that a portion of a medical implant may be passed through or linked to the hole the plications. Others of the embodiments are configured to couple an anchor to the plication as it is formed, so that a medical implant may later be coupled to the anchor.

While this application describes plication systems and methods with respect to the formation of plications in stomach tissue, the embodiments described herein have equal applicability for forming plications in parts of the body outside the GI system.

Plication System of the First Preferred Embodiment

Figure 6:
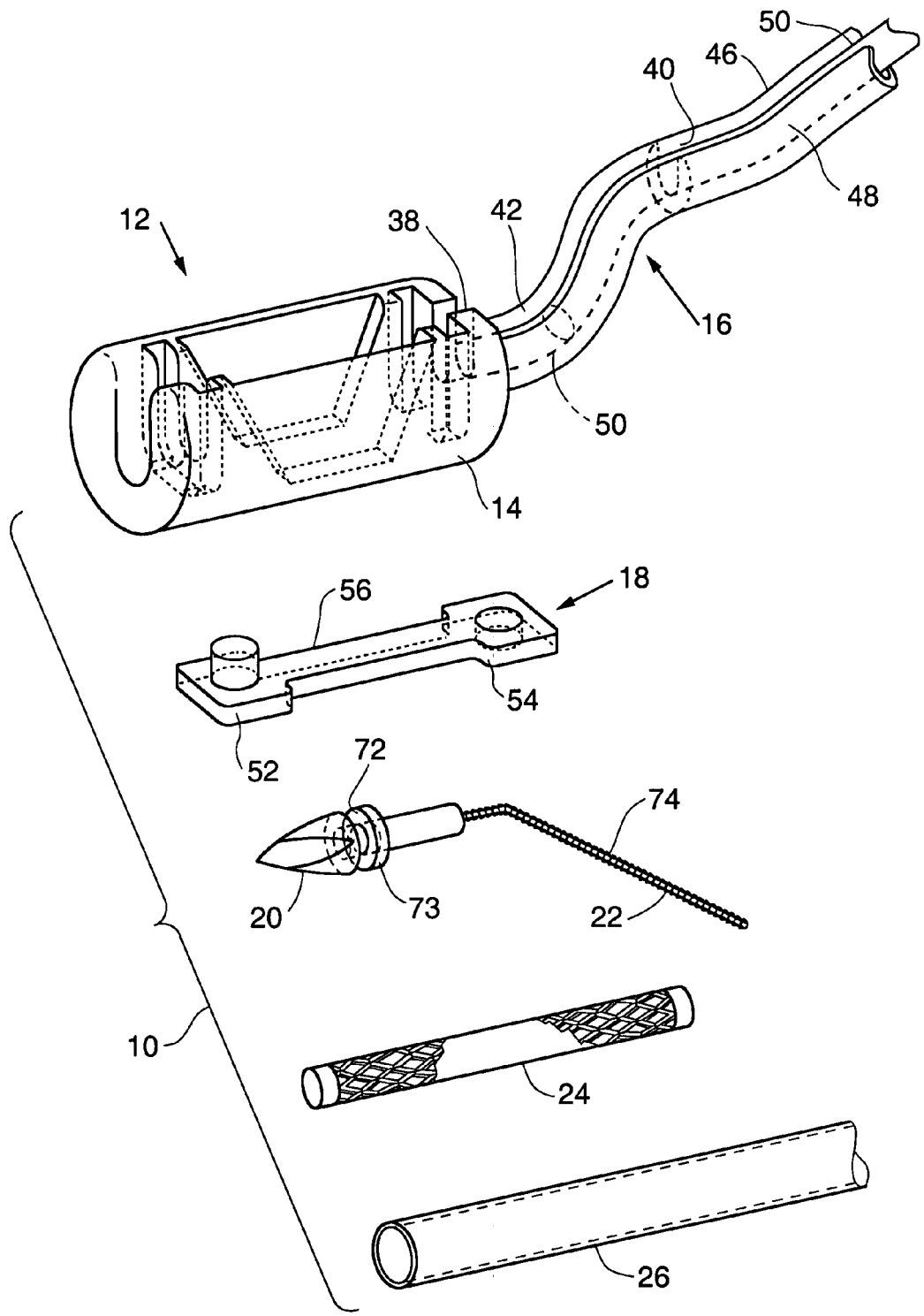
FIG. 6 is a perspective view of an endoscopic plication system.

FIG. 6 illustrates one embodiment of a system 10 for tissue plication that is suitable for endoscopic use, as well as surgical or laparoscopic use if desired.

Generally speaking, system 10 includes a plicator 12 having a vacuum head 14 and a shaft 16. The system further includes a flexible anchor 18 for attachment to stomach tissue, a tissue penetrating tip element 20 having a cable 22, a mesh element 24, and a sheath 26.

Referring to FIG. 7, vacuum head 14 defines a vacuum chamber 28 having an opening that, during use, is positioned into contact with stomach tissue so as to draw the tissue into the chamber 28. Vacuum head 14 further includes slots 32, 34 sized to receive portions of the anchor 18 as described below. The distal and proximal ends of the vacuum head 14 include U-shaped openings 36, 38.

Referring once again to FIG. 6, shaft 16 is a flexible elongate member extending from the proximal end of the vacuum head 14. Shaft 16 is equipped with pull-wires (not shown) and/or alternative means for articulating the vacuum head 14 as needed for proper positioning within the stomach. Shaft 16 includes a distal portion 40 having a generally U-shaped slot 42 corresponding to the U-shaped opening 38 in the vacuum head. The proximal portion 46 of shaft 16 is tubular and includes at least one lumen 48 extending its length.

A tubular cannula 50 extends through the shaft 16 as shown in FIG. 6. Cannula 50 is fluidly coupled to a source of negative pressure such as a syringe or vacuum pump. Application of suction to the cannula 50 creates a vacuum in the vacuum chamber as discussed in detail below. As most clearly visible in FIGS. 8A and 8B, cannula 50 includes an annular flange 53 (FIGS. 8A and 8B) surrounding its distal end. A plurality of proximally-oriented ratcheting elements 51 (FIG. 8B) are positioned within the lumen of cannula 50, adjacent to the cannula's distal end.

Anchor 18 includes a distal tab 52 and a proximal tab 54 on opposite ends of a central portion 56. Anchor 18 is a flexible element formed of silicone or other flexible, biocompatible material. Its properties permit it to be deformed into the orientation shown in FIG. 9 for insertion into the vacuum head. More specifically, the anchor 18 is positionable within the vacuum head 14 as shown in FIG. 12 with the distal tab 52 disposed in distal slot 32 and the proximal tab 54 within proximal slot 34.

As best seen in the cross-section view of FIG. 9, a catch 58 is seated within a recess in the distal tab 52 of anchor 18. Catch 58 may be formed of a resilient material such as stainless steel, nitinol, or resilient polymer that has been overmolded using rubber. As will described in detail below, catch 58 functions to engage a portion of the tip element 20 (FIG. 6) after it has been advanced through the tissue undergoing plication. In the illustrated embodiment, catch 58 includes a cutout 60 proportioned to engage the tip 20, however any alternative configuration for the cutout 60 and tip 20 that will permit engagement of the two is equally suitable. A rubber protrusion 62 is positioned on the anchor 14 to receive the sharp tip of the tip element to prevent injury to surrounding tissue.

Referring again to FIG. 9, proximal tab 54 includes an opening 64 within which a spring element 66 is positioned. Materials used for the spring element may be similar to those used for the catch 58. Spring element functions to engage cable 22 to retain the anchor in position, and it should be appreciated that alternative features that can perform this function can instead be used. As best shown in FIG. 11A, a preferred spring element 66 includes a pair of tabs 68 that can be pushed to a slightly outward orientation (see FIG. 11B) when acted upon by a force shown by arrow A in FIG. 9, but that will return to the closed orientation when the force is relieved. Tabs 60, in their closed orientation, define a central cutout 70.

It is appropriate to note that anchor 18 may take many alternate forms without departing from the scope of the invention. For example, in one alternative embodiment shown in FIG. 13, anchor 18a includes a loop 2 of the type described in connection with FIGS. 2-5 coupled to its distal end.

Referring again to FIG. 6, tip element 20 includes a piercing element that is sufficiently sharp to penetrate abdominal wall tissue when subjected to an appropriate amount of force. The tip element 20 may be formed of stainless steel or any other material suitable for this purpose. A preferred tip element includes a collar 73 which defines a recess 72 between the distal edge of the collar and the proximal edge of the tip. Recess 72 is proportioned to seat within the cutout 60 (FIG. 10) of the anchor's distal catch 58 when the tip element is passed through the cutout 60.

Cable 22 is coupled to the proximal portion of the tip element 20. Cable 22 preferably includes a series of barbs 74, teeth, or other engagement elements. As will be described in connection with FIG. 19A, during use the cable is engaged by spring element 66 which allows the cable to slide in a proximal direction but that prevents movement of the cable in a distal direction. In other words, the cable functions in a manner similar to a cable tie found in hardware stores.

As discussed, the system is preferably designed to pass material between the serosal tissue layers so as to faciliate serosal tissue bonding. The material may be a synthetic or non-synthetic mesh (formed of nitinol or other material), porous or non-porous material, slotted material, or any other material through which adhesions will form or onto which tissue will grow. Examples include, but are not limited to, polypropylene, materials sold under the trade names Goretex or Dacron, or tissue graft material such as the Surgisis material sold by Wilson Cook Medical, Inc. The material may be treated with tissue-ingrowth promoting substances such as biologics.

The delivered material can be constructed into any shape or configuration that will achieve its purpose of promoting strong serosal adhesions. As illustrated in FIGS. 14A and 14B, a convenient form for the delivered material is that of a mesh tube 24 designed such that application of compressive forces between the proximal and distal ends will cause the mesh to take the form of a disk, or such that it will self-expand to a disk-like shape when released from a restrained position. Tubular caps 76a, 76b formed of a suitable polymeric material may be attached to the distal and proximal ends of the tube to minimize damage to the mesh during compression.

Exemplary Method of Using the First Preferred Embodiment

One method of using the system of FIG. 6 will next be described.

In preparation for use, tip 20, cable 22, mesh element 24, and sheath 26 are assembled for insertion into cannula 50. Specifically, as shown in FIG. 15A, mesh tube 24 is threaded over cable 22 and positioned such that its distal cap 76b abuts the collar 73 of tip 20. Sheath 26 is positioned over the mesh tube 24 and advanced such that its distal end is also in contact with the collar 73.

Referring to FIG. 15B, the assembled tip, cable, mesh element and sheath are inserted into the cannula 50. Anchor 18 is seated within the vacuum chamber 28 as described above. The flange 53 of the cannula 50 is positioned in sealing contact with the anchor 18. For example, the flange 53 may be inserted into the proximal opening 64 (FIG. 9) of the anchor so as to create an interference fit between the two. Adequate sealing is desirable to prevent loss of vacuum pressure from the vacuum chamber 28 during use.

Figure 16A:
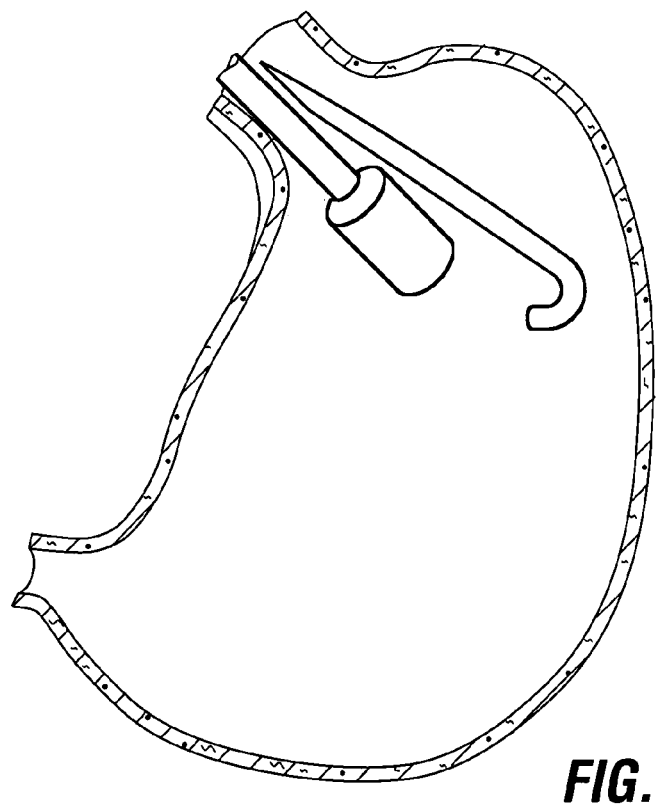
FIG. 16A schematically illustrates introduction of the assembled plicator and an endoscope into the stomach.

Next, the assembled plicator 12 is passed into the stomach S via the esophagus as shown in FIG. 16A. An endoscope 80 is also passed into the stomach to provide visualization of the procedure. Although the endoscope 80 is shown as a separate component, the plicator 12 may be modified to include an integrated endoscope.

Figure 16B:
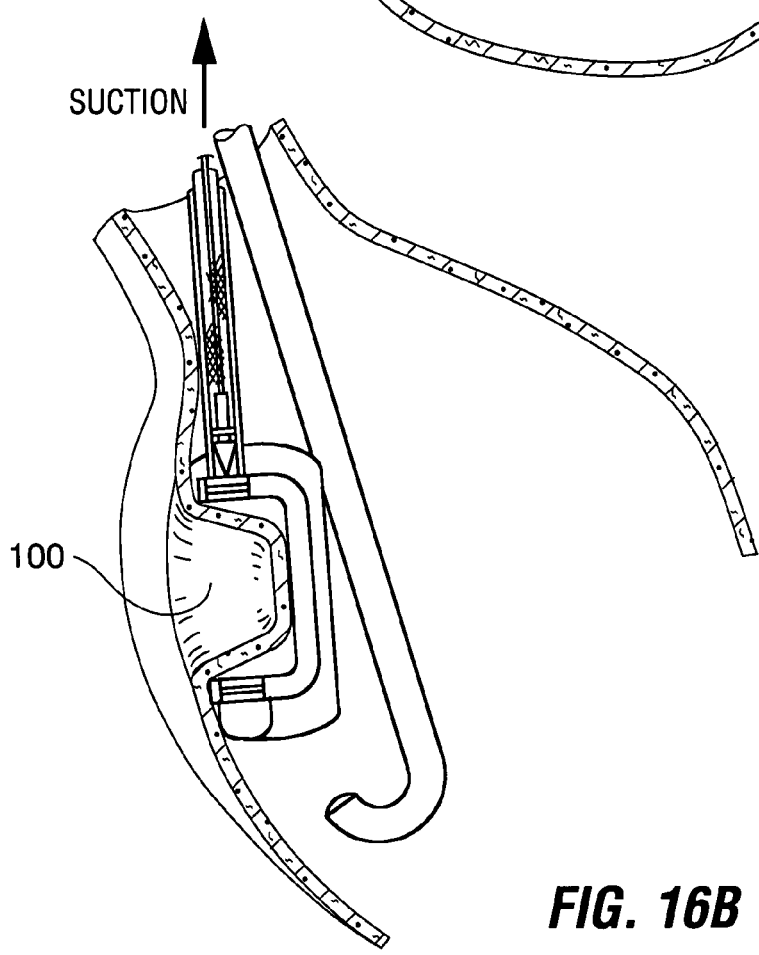
FIG. 16B schematically illustrates creation of a tissue pocket using the plicator of FIG. 16A.

Referring to FIG. 16B, the plicator 12 is advanced to a target location at which a plication is to be formed. The plicator is manipulated using pull wires or other steering elements to place vacuum chamber 28 against the stomach tissue. Suction is applied to the vacuum chamber 28 via cannula 50, thus drawing stomach tissue into the vacuum chamber as shown. Consequently, a pocket 100 forms in the tissue such that if the stomach were to be viewed from the outside a depression in the stomach wall would be visible. Suction is maintained to stabilize the tissue within the vacuum chamber. If additional stabilization of the tissue is desired, the plicator 12 may be provided with a barbed stabilization cuff 82 of the type shown in FIG. 17A. Cuff 82 includes a plurality of barbs 84 oriented to penetrate stomach tissue as shown in FIG. 17B when the tissue is drawn into the chamber 28, thus holding the proximal portion of the captured tissue in place during advancement of the tip member 20 and mesh 24 element. Other stabilizing mechanisms may alternatively be used in lieu of, or in addition to, the cuff and barbs.

At this point, the tissue is ready for advancement of the tip member 20 through the tissue, as well as deployment of the mesh tube 24 into the pocket 100. Advancement of the tip and deployment of the mesh may be performed in a single step, or they may be formed as a sequence of steps. For simultaneous advancement and deployment, sheath 26 is advanced in a distal direction, thereby driving the tip 20 distally through the tissue walls 102 defining the pocket 100. If the forces of friction between the tubular mesh element 24 and the sheath 26 are sufficiently large, the advancing sheath carries the mesh tube 24 into the pocket. Alternatively, a pushing mandrel 86 (shown in FIG. 17B) may be advanced distally against the proximal cap 76a of the mesh element 24 to advance the mesh element 24 into the pocket 100. If separate advancement of the tip member 20 and deployment of the mesh element 24 is preferred, the tip member 20 is first driven in a distal direction by distal movement of the sheath 26, and the mesh element is then separately pushed over the cable 22 using the mandrel 86.

Many alternative structures useful for separately or simultaneously applying pushing forces to the tip element 20 and the mesh element 24 are readily conceivable and may also be used.

Regardless of the mode of deployment, as the tip member 20 is advanced, its pointed distal end moves into contact with the spring element 66 on the anchor 18, causing tabs 68 (FIGS. 9, 11A and 11B) to push distally into the position shown in FIG. 11B, and to then return to their substantially planar orientation (FIG. 11B) once the tip member 20 has cleared the spring element 66. The tip element 20 then passes through the walls 102 of tissue and into engagement with the distal catch 58 of the anchor 18 (i.e. the edges of the cutout 60 seat within recess 72 of the tip element 20), thereby locking the tip element to the catch 58. The distal-most portion of the tip element 20 embeds within the protrusion 62 of the anchor.

Figure 18A:
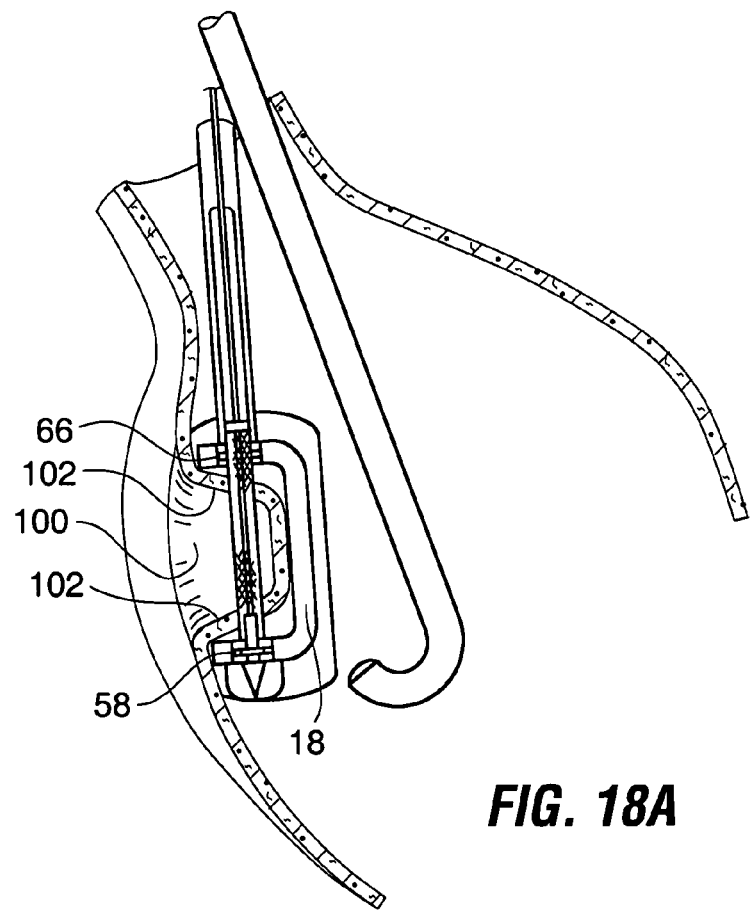
FIG. 18A schematically illustrates positioning of the tip element and mesh tube following their deployment.
Figure 18B:
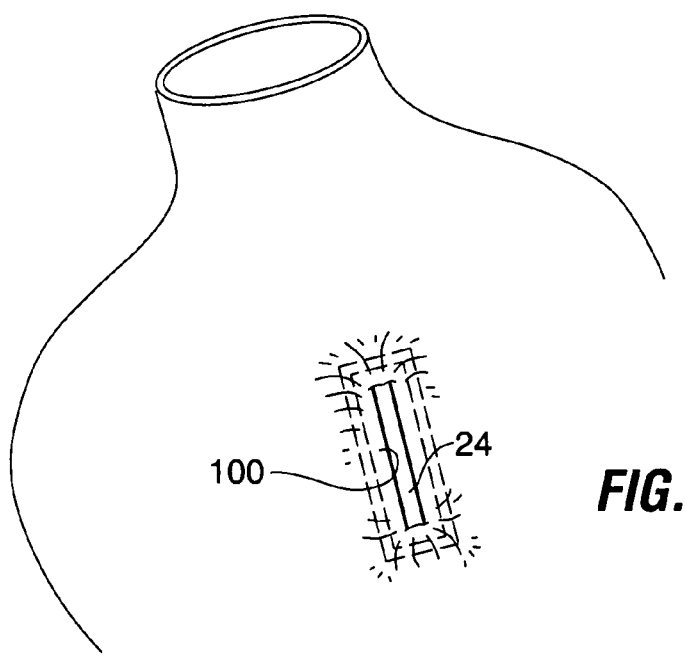
FIG. 18B schematically illustrates the stomach exterior surface following deployment of the tip and anchor.

The cable 22 remains attached to the tip element 20 and thus extends through the walls 102, through catch 58 and spring element 66, and through the cannula 50. The mesh tube 24 remains disposed around the cable 22. FIG. 18A is a cross-section view of the stomach illustrating the arrangement of the components after the tip element 20 and mesh tube 24 have been deployed. FIG. 18B shows the outside of the stomach at this stage of the procedure.

Figure 19A:
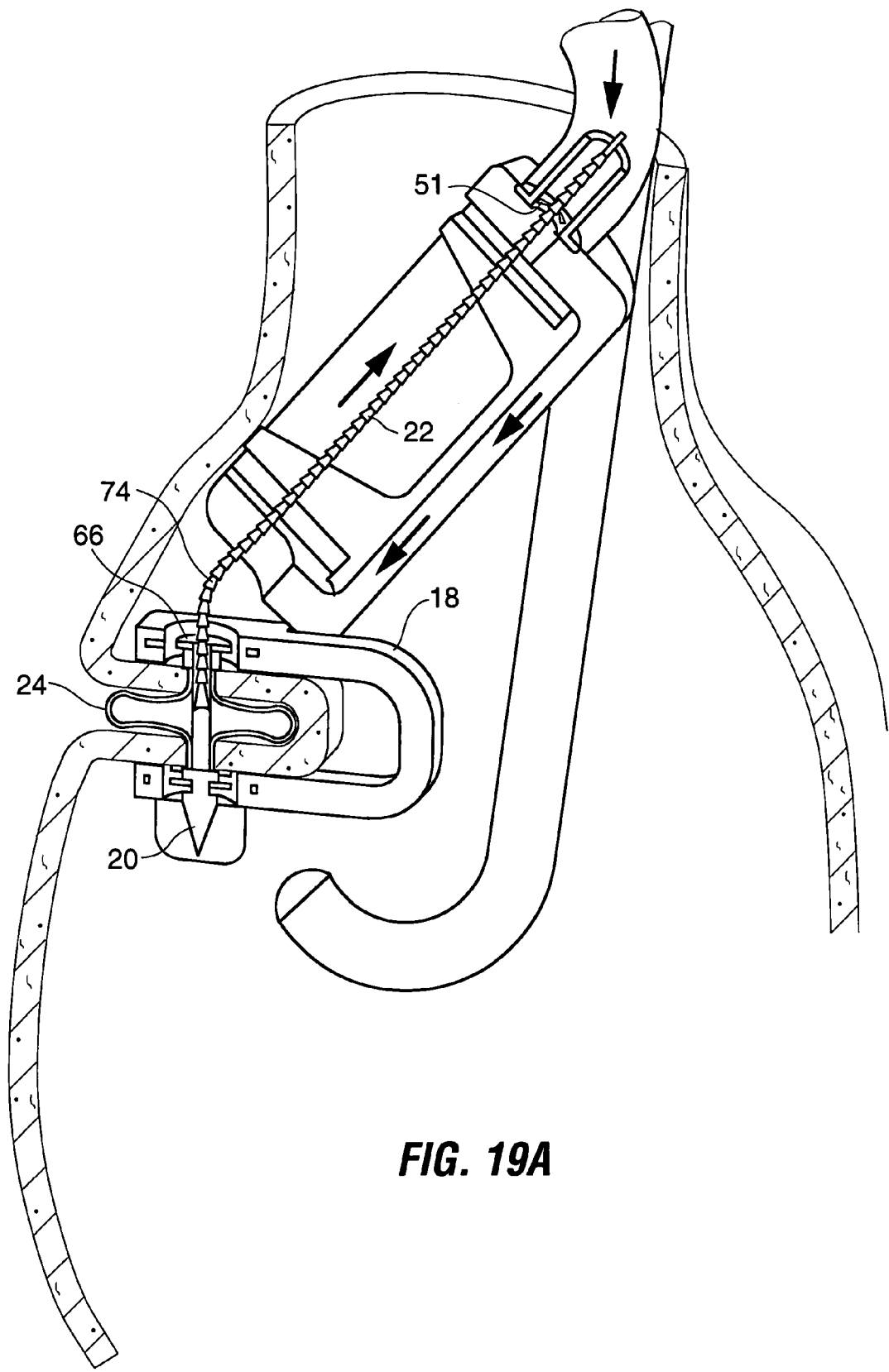
FIG. 19A illustrates compression of the anchor using the plicator and cable.

The next series of steps are geared towards drawing the distal and proximal tabs 52, 54 of the anchor 18 towards one another, so as to enclose the mesh element 24 within the pocket 100. Referring to FIG. 19A, the vacuum head 14 is moved in a lateral direction until it separates from the anchor 18 and the pocket 100. (If a barbed stabilization cuff 82 of the type shown in FIG. 17A has been used to engage the tissue, the cuff is first rotated to "unscrew" its barbs from the tissue. This might be achieved, for example, using a rotatable element (not show) that may be grasped and rotated by the user.) Vacuum head 14 is then positioned against the anchor 18 and used to impart a distally-oriented force against the proximal side of the anchor 18. At the same time, traction is applied to cable 22 so as to impart proximally directed forces to the distal end of the anchor. Ratcheting elements 51 in the cannula 50 prevent the cable 22 from sliding distally in the event that traction of the cable 22 is momentarily released.

Figure 19B:
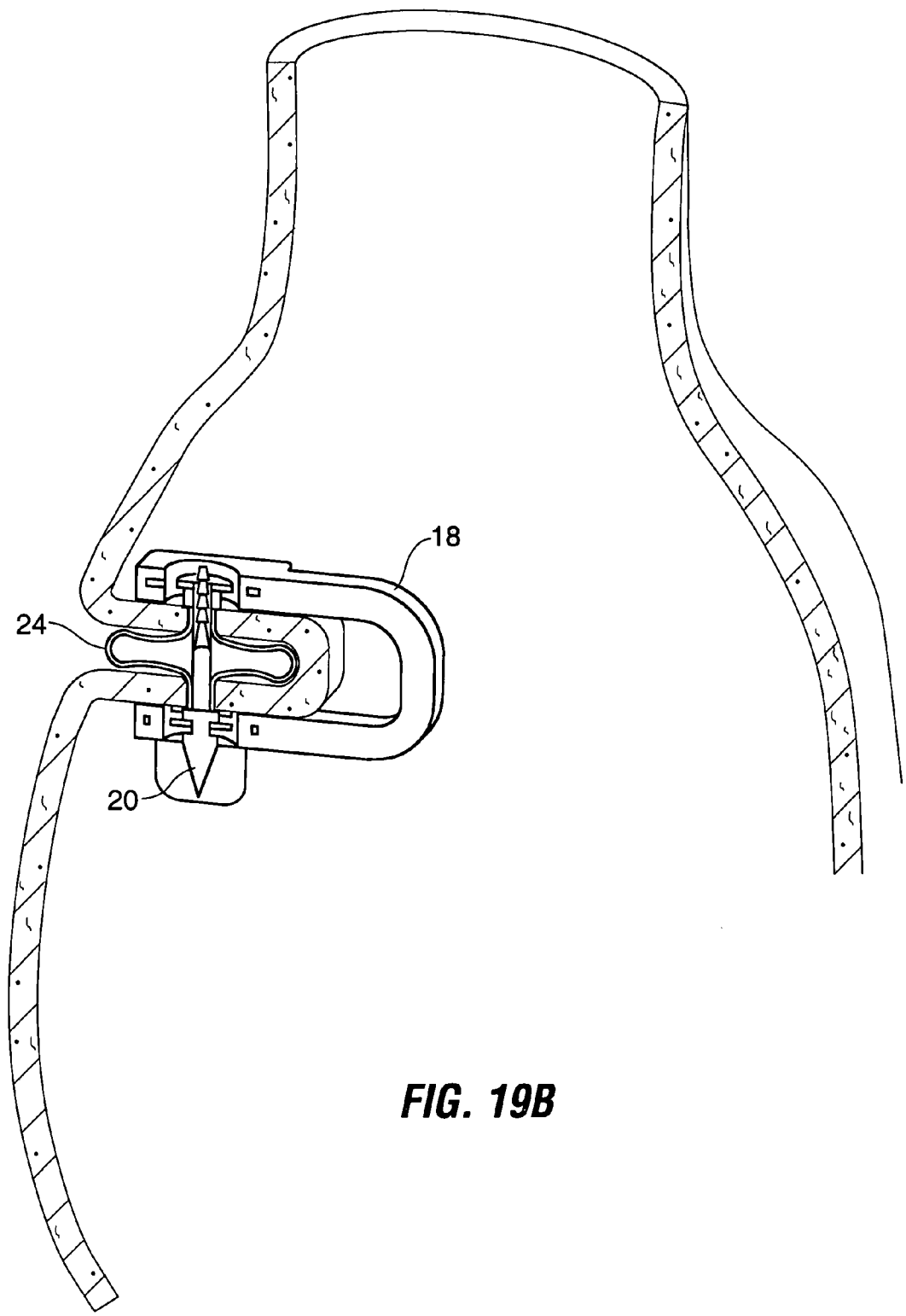
FIG. 19B shows the final anchor and mesh position following removal of the plicator and endoscope.

The opposed forces between cable 22 and vacuum head 14 result in compression of the anchor 18 and the mesh tube 24 into the illustrated positions. As the cable 22 tightened, the spring element 66 of the anchor sequentially engages barbs on the cable 22. Once tension on cable 22 is released, the spring element 66 remains engaged with the adjacent barb on the cable so as to retain the anchor in the compressed position. Finally, the cable 22 is clipped, and the plicator 12 is withdrawn from the body, leaving the anchor 18 and mesh positioned as shown in FIG. 19B. The procedure may be repeated to form multiple plications if needed. Following formation of the plication(s), a medical implant may be coupled to the anchor(s) 18 during the course of the same procedure or during a later procedure scheduled to permit sufficient formation of adhesions between the serosal tissue layers 102 to support the implant.

Figure 20:
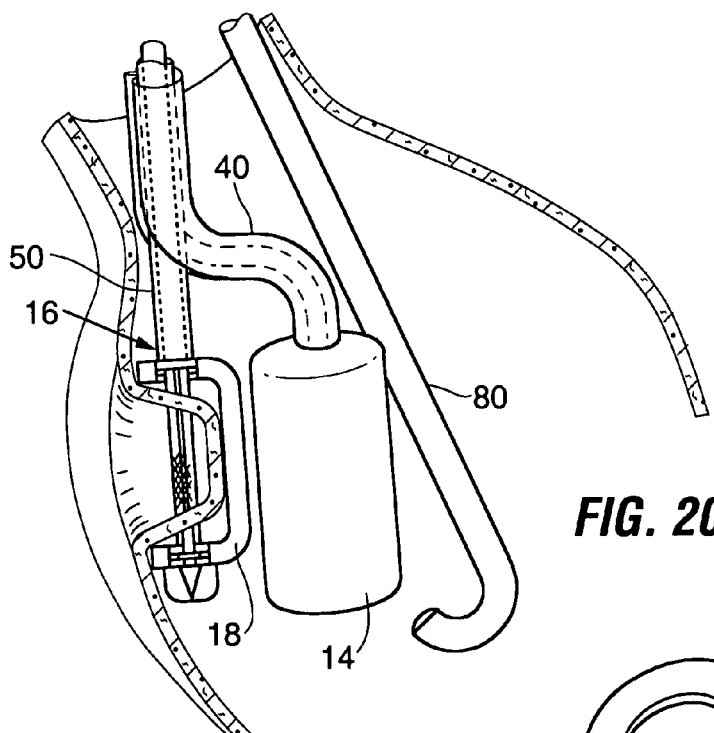
FIG. 20 illustrates an alternative method for compressing the anchor.

It should be noted with reference to FIG. 20 that in an alternative method, the cannula 50 may remain coupled to the anchor 18 during lateral movement of the vacuum head 14, causing the proximal portion 40 of the shaft 16 to separate from the cannula 50. According to this embodiment, the anchor 18 may be compressed by pressing the cannula 50 downwardly against the anchor 18 while applying tension to the cable 22. Once the anchor has been secured as described with respect to FIGS. 19A and 19B, the cannula 50 is detached from the anchor 18 and withdrawn from the body.

Alternatives to the First Embodiments

Figure 21A:
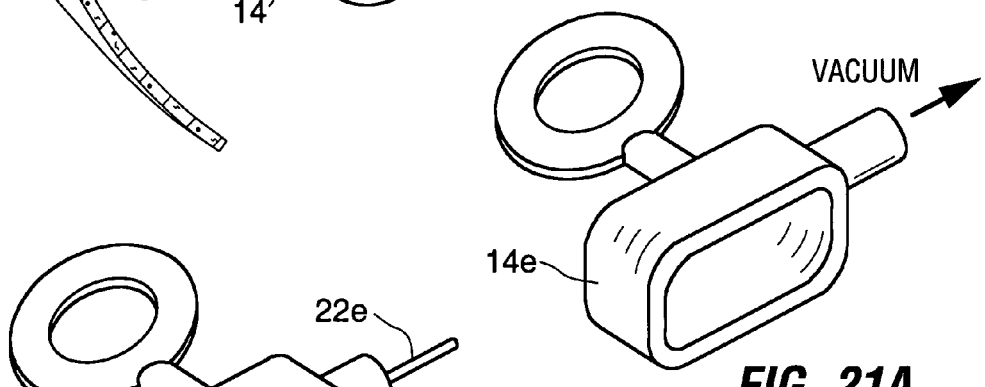
FIGS. 21A through 21C are perspective views illustrating an alternative vacuum chamber in which the vacuum chamber also forms the implantable anchor.
Figure 21B:
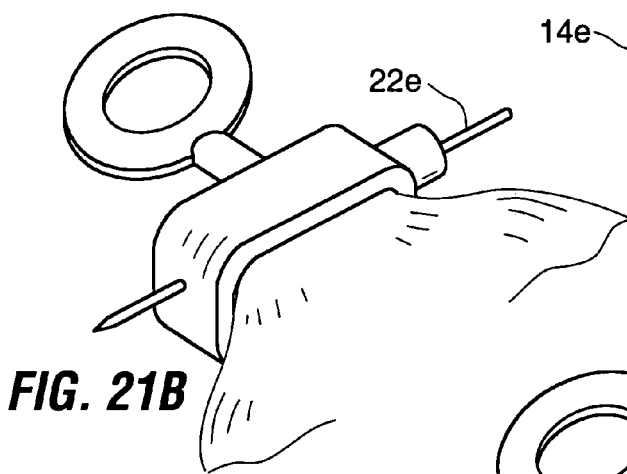
Figure 21C:
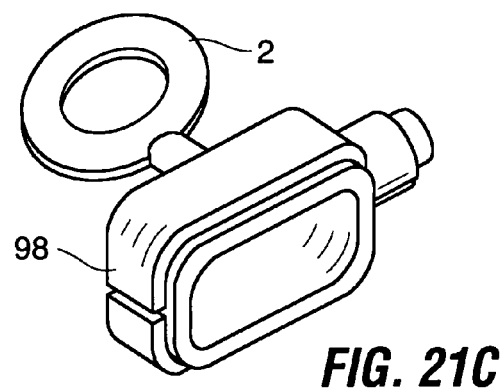

One alternative system illustrated in FIGS. 21A through 21C is similar to the first preferred embodiment, but differs in that the vacuum head 14e is formed of a compliant material such as silicone and also functions as the anchoring device. During use of the vacuum head 14e, suction is applied to draw tissue into the vacuum head, and a cable 22e (or suture, etc) is passed through the compliant silicone material to form the tissue plication. If necessary, a removable rigid housing 98 may be positioned around the vacuum head to prevent it from collapsing during application of suction.

In another alternative system shown in FIGS. 22A through 22D, a flexible vacuum paddle 110 is positionable into contact with stomach tissue. In this embodiment, paddle 110 also serves as the anchor that will remain coupled to the tissue.

Figure 22A:
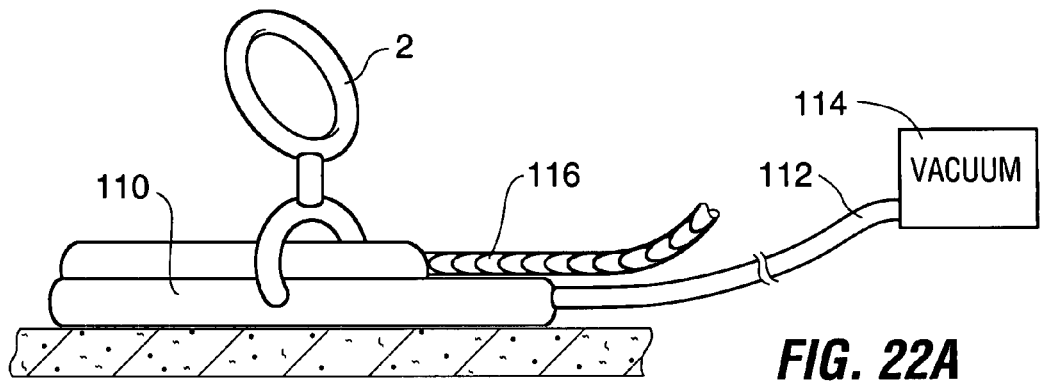
FIGS. 22A through 22D are a sequence of steps illustrating an alternative method using a vacuum paddle that additionally functions as an implantable anchor.
Figure 22B:
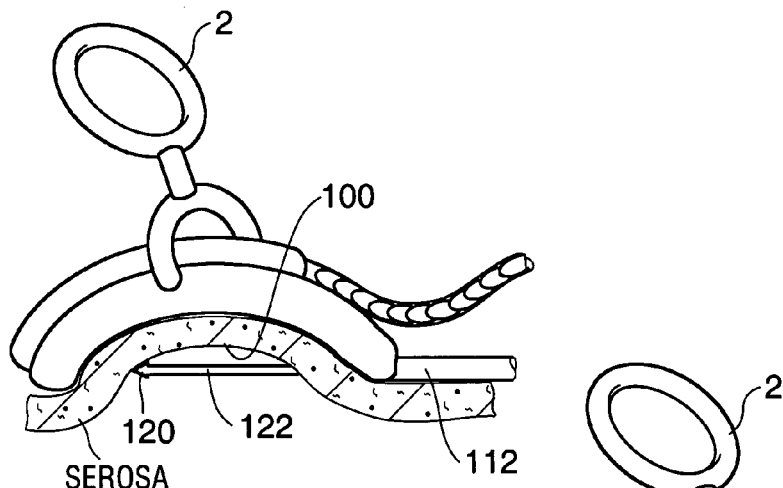
Figure 22C:
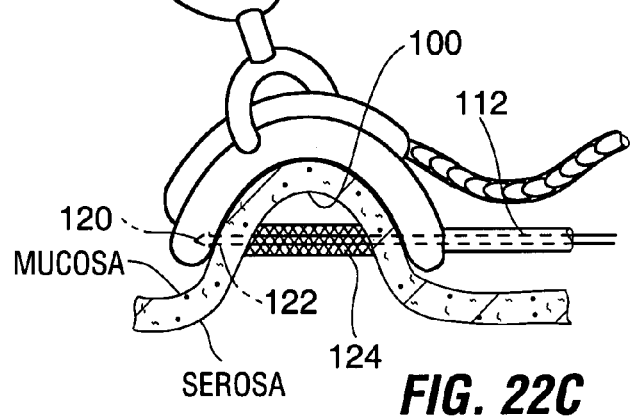
Figure 22D:
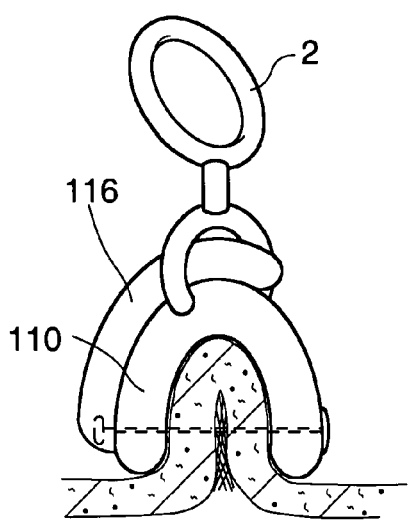

Paddle 110 includes an elongate tube 112 that extends through the esophagus and is connectable to a vacuum source 114 positioned outside the body. Paddle 110 is formed of silicone or other flexible material suitable for long term implantation. Loop 2 is integrally coupled to the paddle. An elongate spine 116 is positionable against the paddle 110, and may include elements for temporarily engaging the paddle 110. Spine 116 includes pull wires or other features that may be manipulated from outside the body to deflect it and the adjacent paddle 110 into nested curved positions as shown in FIG. 22B, thus creating a pocket 100 in the tissue. A tip 120 coupled to a cable 122 may be advanced through the elongate tube 112 such that it penetrates the tissue lining the pocket 100 and advances into a portion of the paddle 110, where it is engaged by a catch (e.g. see catch 58 of FIG. 8A). A mesh element 124 may be advanced over the cable 122 as shown in FIG. 22C, and the cable 122 may be cinched to form the plication using techniques such as those described above, leaving the paddle 110 and loop 2 in place.

Figure 23A:
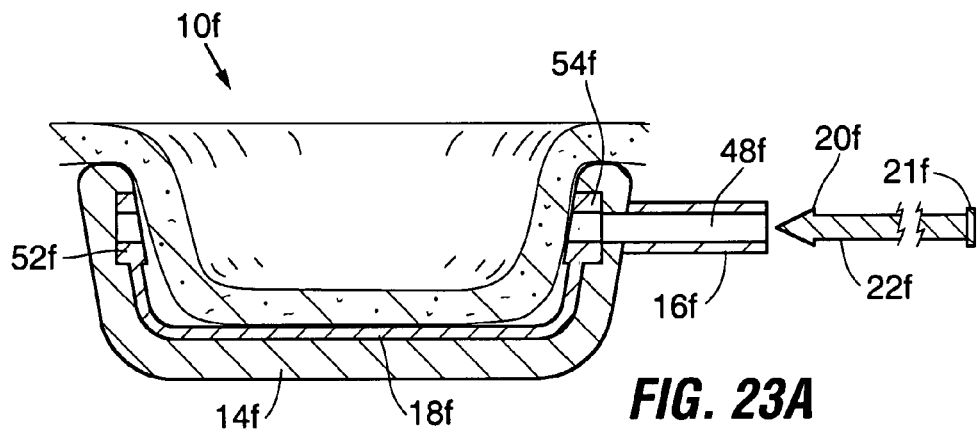
FIGS. 23A through 23B and 24A through 24B are a sequence of steps illustrating an alternative method which forms a serosal tunnel and positions a leg of an anchor within the serosal tunnel.
Figure 23B:
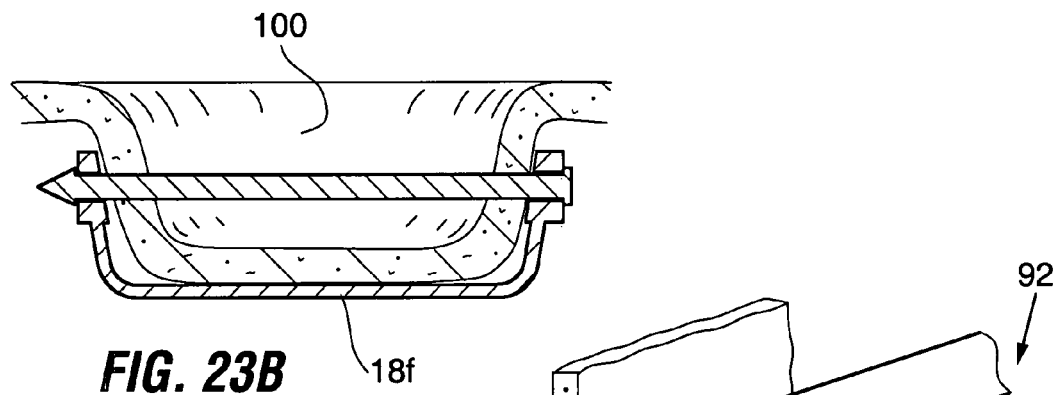

An alternative system illustrated in FIGS. 23A and 23B is similar to the system of the first embodiment of FIG. 6. Specifically, system 10f includes a vacuum head 14f mounted at the distal end of a shaft 16f of sufficient length to permit the vacuum head 14f to be positioned within the stomach while the proximal portion of the shaft 16f remains outside the oral cavity. The vacuum head is coupled to a source of suction, such as a syringe or vacuum pump.

A flexible anchor 18f is seated within vacuum head 14f prior to use, similar to the positioning of the anchor 18 of the first embodiment shown in FIG. 12. The anchor 18f includes a distal tab 52f and a proximal tab 54f having corresponding openings longitudinally aligned with the lumen 48f of the shaft 16f. The system differs from the first embodiment in that the anchor 18f further includes an elongate leg 22f that is coupled to the tabs 52f, 54f during assembly to form the anchor 18f into a loop. Leg 22f includes a tip 20f and a catch 21f positioned to engage the distal tab 52f and the proximal tab 54, respectively. The leg 22f may be manufactured of a flexible polymeric material such as silicon, or it could be formed of a mesh, braid, stent into which surrounding tissue will grow. However, the tip 20f should be capable of penetrating stomach wall tissue.

Prior to use, the leg 22f is positioned within the lumen 48f of shaft 16f. During implantation of the anchor 18f, serosal tissue is drawn into the vacuum head 14f as shown in FIG. 23A. The leg 22f is advanced through the tabs 52f, 54f, and the sections of stomach wall lying between the tabs, using a push rod (not shown) or other pushing mechanism as described above. The tip 20f engages with distal tab 52f and the catch 21a is restrained by proximal tab 54f. The vacuum head 14f is subsequently removed, leaving the anchor and leg forming a loop surrounding a portion of the stomach wall as shown in FIG. 23B.

Figure 24A:
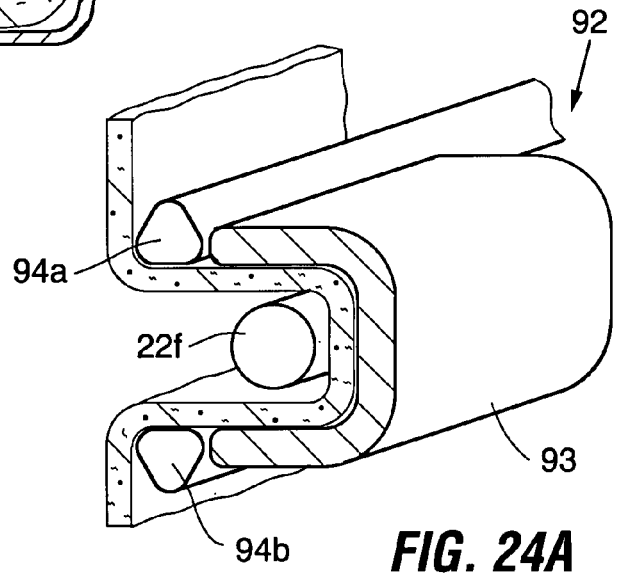

Although the method of implanting the anchor 18f may end with the anchor 18f positioned as shown in FIG. 23B, it is preferable to bring some of the serosal tissue surfaces surrounding pocket 100 into contact with one another so as to trigger growth of serosal bonds between the contacting tissues surfaces, as described before. Methods for cinching the tissue to form a serosal plication are described above and may be modified for use with the FIGS. 23A-23B method. Alternatively, elongate regions of tissue on opposite sides of the leg 22*f* may be brought into contact with one another and clamped, stapled and/or otherwise held in contact to turn the pocket 100 into a sealed serosal pocket 100*f* surrounding the leg 22*f* and isolated from the sterile environment outside the stomach. For example, as shown in FIG. 24A, a jaw-type stapling instrument 92 having a vacuum housing 93 may be endoscopically introduced into the stomach and positioned with the jaws 94*a*, 94*b* contacting mucosal tissue on opposite sides of the leg 22*f*. This instrument may be separate from the instrument used to couple the anchor 18*f* to the tissue, or the instrument of FIG. 23A may be modified to include the stapler jaws 94*a*, 94*b*.

Figure 24B:
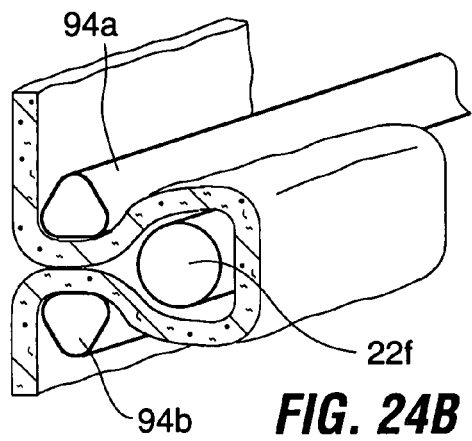
Figure 25A:
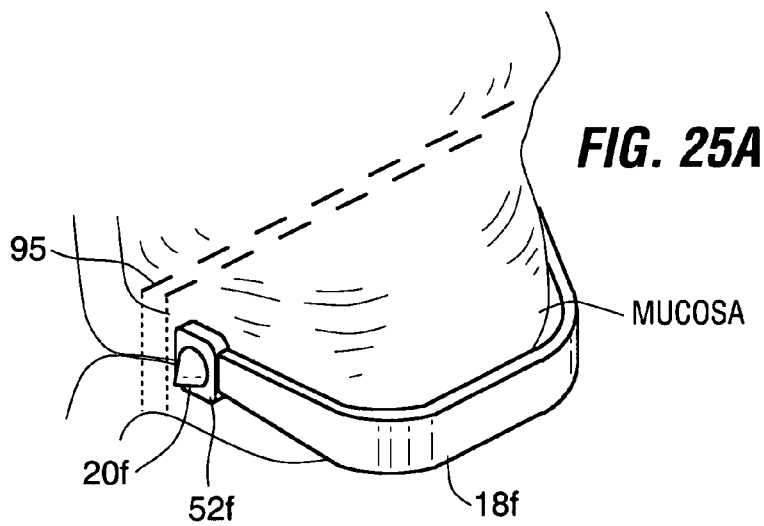
FIG. 25A is a perspective view taken from within the stomach illustrating the serosal tunnel formed during the sequence of steps illustrated in FIGS. 23A through 24B.
Figure 25B:
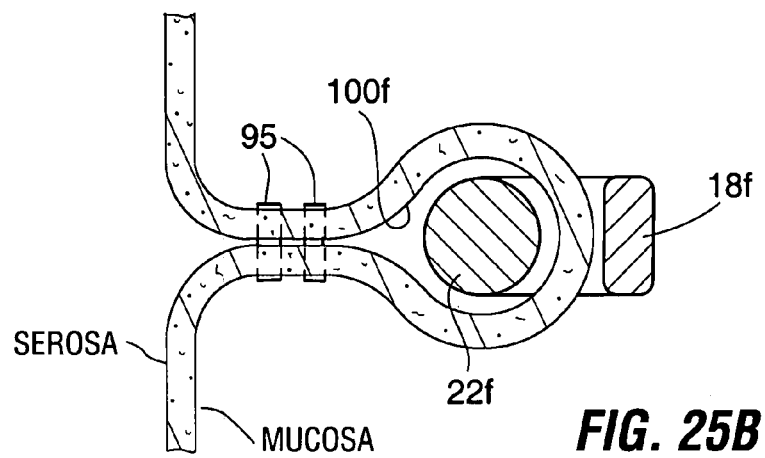
FIG. 25B is a cross-section view of the serosal tunnel and anchor shown in FIG. 25A.
Figure 25C:
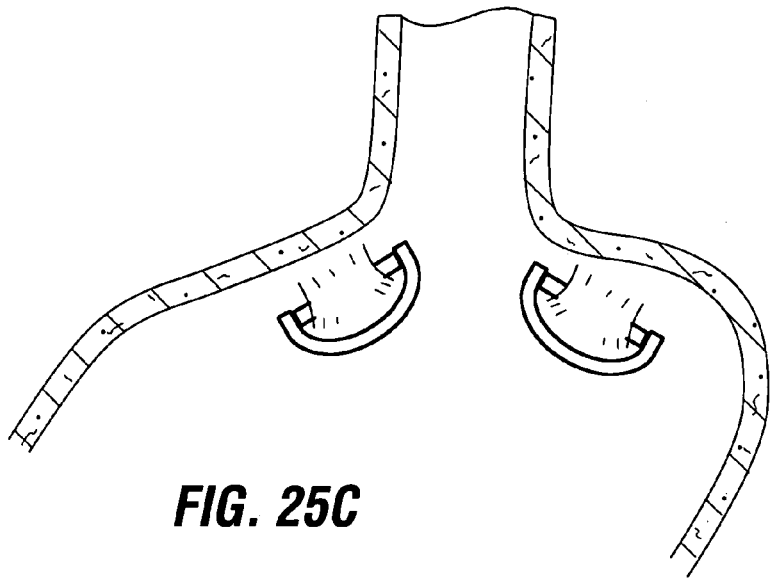
FIG. 25C illustrates placement of two of the anchors of FIGS. 23A-24B within a stomach.

The jaws are clamped as shown in FIG. 24B to bring the serosal tissue surfaces together, and staples are passed through the tissue using the jaws, enclosing the pocket 100 in the tissue and helping to retain the anchor using the re-shaped stomach tissue. After the instrument 92 is removed from the stomach, the serosal tissue surfaces remain held in contact by one or more staple lines 95 (FIGS. 25A and 25B). The staple lines 95 seal the pocket 100*f* and reduce the chance of infection by forming a barrier preventing gastric contents that might enter the pocket 100*f* from moving into the extragastric space. Adhesions will then form between the serosal tissue surfaces as described above. To optimize the strength of the adhesions, the leg 22*f* may include ingrowth-promoting features. For example, leg 22*f* may be configured to support macro-level ingrowth using a mesh design, or it may include micro-ingrowth promoting features such as a porous surface. Leg 22*f* might alternatively or additional have a surface coated or impregnated with sclerosing agents. Multiple anchors 18*f* may be implanted using this method, as shown in FIG. 25C.

In alternate plication methods, one or more sclerosing agents may be used in conjunction with or in lieu of the mesh element 24. Examples of sclerosing agents include but are not limited to Sodium Tetradecyl Sulfate (STS), Poliodocanol, Chromated Glycerin, Hypertonic saline, Sodium Morrhuate, Sclerodex (hypertonic saline in combination with Dextrose). Other substances that may be positioned with or in place of the mesh element 24 include methylmethacrylate, glues, adhesives, and biorubbers. These may be injected at the time of mesh placement or loaded into the mesh itself and eluded out over a period of time.

FIGS. 26A through 26F illustrates an alternative method in which a cannula 50*a* having a tissue-penetrating distal end is passed into the tissue pocket 100 for delivery of an agent. According to the alternative method, tissue pocket 100 is formed using methods similar to those described above. Cannula 50*a* is advanced through the shaft 16*a* of the plicator 12*a*, through anchor 18*a* and tissue 102, and into the pocket 100. The desired agent is passed through the cannula 50*a* and into the pocket.

Once the agent is administered, steps similar to those described above may be performed to form the plication and to attach anchor 18*a* to the plication. Tip 20*a* (FIG. 26B) is thus advanced through the cannula 50*a* (or through a separate cannula introduced upon removal of the cannula) and advanced as described in connection with the first embodiment. If a mesh element 24*a* is to be introduced, it may be positioned around the cable 22*a* as described previously. A pusher tube 86*a* may be threaded over the cable 22*a*, through the interior of the mesh tube 24*a*, and into contact with proximal cap 76*a* on the mesh element 86*a*. Sliding the pusher tube 86*a* distally drives the tip 20*a* through the plication and into engagement with a distal catch 58*a* on the anchor, as also advances the mesh element 24*a* into the pocket 100. In a final sequence of steps, the plication may be "cinched" using methods similar to those described above.

Figure 28:
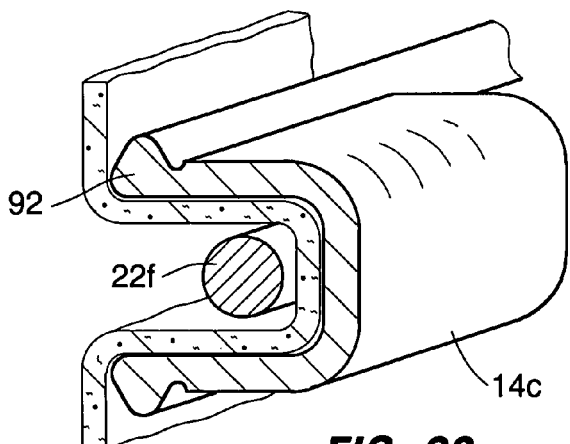
Figure 29:
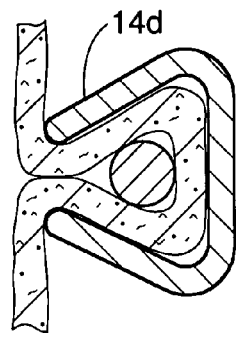

In certain instances, it might be desirable to completely close the serosal pocket 100 to avoid leakage of injected agents into the peritoneal cavity. The pocket 100 may be sealed using an elongate clamp 90 endoscopically introduced into the stomach and clamped over the tissue pocket to press the serosal surfaces into contact with one another as shown in FIGS. 27A and 27B. Alternatively, vacuum head 14*c* (FIG. 28) may include clamping bars 92, such as elongate rods or inflatable balloons, that are positioned on opposite sides of the pocket to clamp the pocket 100 between them. As yet another alternative, the vacuum head 14*d* may be biased or hinged to clamp the pocket 100 as shown in FIG. 29.

An alternative method for forming plications using sclerosing agents to accelerate scar formation is illustrated in FIGS. 30A through 30E. This method is advantageous in that it allows plications to be formed without the use of sutures or cables, and thus can simplify the procedure.

As with previous methods, a pocket 100 or depression is formed on the serosal surface by drawing a portion of the stomach wall inwardly using a vacuum head 14*f* or other device introduced transorally into the stomach. A delivery member 130 is next introduced into the stomach. The delivery member 130 is an elongate tubular device having a lumen through which a sclerosing agent may be delivered, as well as a delivery means for delivering a place holding element 132 into the pocket 100. The delivery member 130 preferably includes a sharpened distal tip capable of penetrating the stomach wall.

Figure 30A:
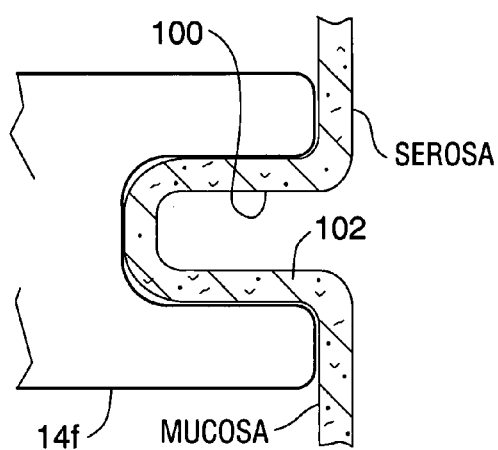
FIGS. 30A through 30D are a sequence of side views of a stomach wall engaged by a vacuum chamber, and illustrate steps of an alternative method of forming a tissue plication using sclerosing agents.
Figure 30B:
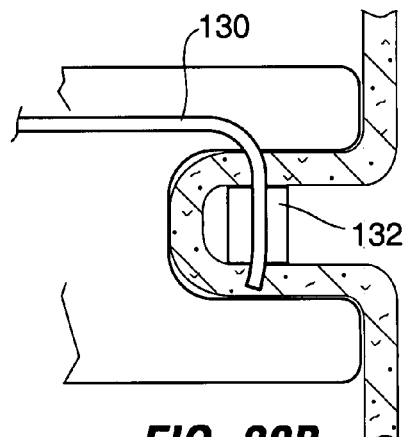

As shown in FIG. 30B, the delivery member 130 is advanced through at least one portion of the stomach wall 102, and used to deliver the place holding element 132 into the pocket 100. The place holding element 102 functions to maintain separation between opposed serosal walls 102, so that the volume between the walls can be filled by a sclerosing agent introduced by the delivery member 130 or a separate delivery method.

In one embodiment, the place holding element 132 may be delivered by pushing it through the lumen of the delivery member using a pushing mandrel. The place holding element might be a section of material that has a compact size and shape for delivery by the delivery member 130, but that expands upon delivery into the pocket 100. To give a few examples, the element may be formed of a structure having mechanical properties (e.g. sponge or nitinol mesh) that cause it to self-expand when released from the delivery member, or it may be an inflatable balloon tethered to an inflation lumen in the delivery member, or it may be a swellable hydrogel that will increase in volume once exposed to fluid within the pocket (e.g. the sclerosing agent or other fluid injected into the body, and/or fluids present in the peritoneal cavity). In alternate embodiments the place holding element might be delivered directly to the outside of the stomach using laparoscopic methods.

The element may be formed of a permanent or semi-permanent material (such as the examples described in connection with mesh element 24 above), that will reinforce the plication and/or work together with the sclerosing agent to promote scar formation. Alternatively, the element may be one that is biodegradable or bioabsorbable over a period of time.

Figure 30C:
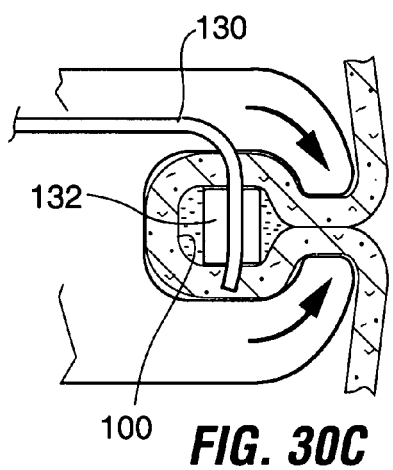
Figure 30D:
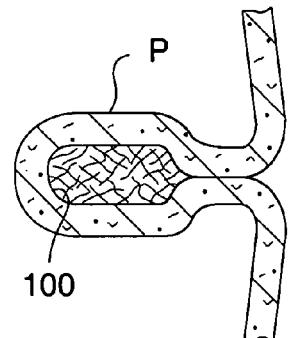

Once the place holding element 132 has been positioned, the vacuum head 14*f* or a separate clamping device is utilized to clamp and seal the pocket 100 as shown in FIG. 30C (see, for example, the sealing methods described above). Sclerosing agent is injected through the delivery member 130 into the pocket 100. Referring to FIG. 31A, if the place holding element is an inflatable balloon 132a or another type of element that can seal against the tissue forming the pocket, it may be acceptable to eliminate the step of applying sealing forces to the pocket. Referring to FIG. 31B, use of a sponge 132b in lieu of balloon 132a may minimize migration of sclerosing agent out of the cavity. The sponge 132b may be filled with sclerosing agent prior to its delivery into the pocket 100, or it may instead absorb agent introduced into the pocket.

Sealing forces continue to be applied to the pocket 100 until ample scar tissue has formed within the pocket to maintain the P. Once adequate scar tissue has been formed, sealing forces may be released and the vacuum head removed from the stomach. If the balloon of FIG. 31A is used in lieu of sealing forces, inflation of the balloon is maintained until the sclerosing agent has formed an adequate amount of scar tissue.

It should be noted with reference to FIGS. 32A and 32B that if sealing forces are needed over an extended during (i.e. to ensure sufficient tissue scarring to retain the plication), a clip 134a may be clipped around the plication to maintain the plication until sufficient scarring has occurred. If needed to prevent unwanted detachment of the clip, an alternative clip 134b (FIG. 31B) may include prongs positioned to pass through the tissue.

Plication System of the Second Preferred Embodiment

In many instances it may be desirable to form serosal tissue plications of the type shown in FIG. 33A, which include a cutout C or hole formed through the plication P. As shown in FIG. 33B, multiple such plications may be formed within the stomach to provide a platform for mounting an intragastric device or for other purposes that will be described below.

When a cutout plication is formed, it may be beneficial to form a seal around the cutout C using staples, sutures or adhesives etc so as to prevent food material and/or gastric juices from passing between the opposed layers of serosal tissue where they can potentially cause infection between the tissue layers or within the extra gastric space. In the FIG. 33A example, a circular array of staples is placed in the tissue surrounding the cutout C for this purpose. Sealing the cutout using staples provides the additional benefit of controlling the bleeding that will occur along the edges of the cutout. In forming the plication P, reinforcing mesh or other suitable material may be positioned between the opposed serosal layers so as to achieve the benefits discussed in connection with the first embodiment.

A second preferred embodiment of a plication system 10g, shown in cross-section FIG. 34A, is particularly useful for forming a serosal plication having a cutout surrounded by a staple line, and also for positioning a reinforcing mesh element within the plication.

In general, system 10g includes a plicator 12g comprising a vacuum head 14g having a vacuum chamber 28g and a shaft 16g defining a lumen 48g. A port 49 is fluidly coupled to the vacuum chamber 28g and is connectable to an extracorporeal source of suction (e.g. a syringe or a vacuum pump).

An elongate staple driver 150 is longitudinally moveable within the lumen 48g. Staple driver may take the form of an elongate tube having a broadened annular head 152 positioned within the vacuum head 14g. A plurality of staples 154 is arranged adjacent to the staple head, preferably in a circular arrangement, but alternative arrangements are equally suitable. A circular anvil 156 is positioned within the vacuum head 14g opposite the staples. Staple driver head 152 is moveable in a distal direction to advance the staples across the vacuum chamber and into contact with the anvil 156.

The system includes a tubular cannula 50g for forming the cutout C in the tissue. Cannula 50g extends through the lumen of the staple driver 150, with its tissue-penetrating distal end oriented towards the vacuum chamber 28g. Cannula 50g may be advanced in a distal direction to extend through the vacuum chamber 28g and into a tubular channel 158 formed in the distalmost section of the vacuum head.

An elongate rod 160 having a pointed distal barb or tip 20g extends through the lumen of the cannula 50g. Tubular mesh element 24g surrounds a portion of the exterior surface of rod 160, with its distal end adjacent to the proximal end of tip 20g. Mesh element 24g is preferably a self-expandable tubular element of the type described in connection with FIGS. 14A and 14B. When positioned on the rod 160, the mesh element is compressed to a reduced-diameter position and retained in the compressed position using a retention sleeve 162. A tubular support 164 may be positioned on the rod 160 in abutment with the proximal end of the mesh element 24g.

System 10g further includes a proximal handle (not shown) that remains outside the body during use of the system. The handle includes actuators, pull wires, push rods, or equivalent components that facilitate longitudinal advancement and withdrawal of the tip 20g, cannula 50g, retention sleeve 162, and staple driver 150, as well as deflection or articulation of the components, as needed to carry out the method for using the system described in the following section.

Exemplary Method for Using the Second Preferred Embodiment

A method for using the system of the second embodiment will next be described. First, the vacuum head 14g is introduced into a stomach and endoscopically positioned with the vacuum chamber facing the interior surface of the stomach wall. This step is similar to the step illustrated in FIGS. 16A-16B in connection with the first embodiment.

Suction is applied to the vacuum head 14g via port 49 to draw a portion of the stomach wall into the chamber as shown in FIG. 34B, thus orienting sections S1, S2 of the stomach wall with their serosal surfaces generally facing one another.

Next, the rod 160 is advanced to drive tip 20g through the sections S1, S2. Tip 20g is captured within the channel 158 adjacent to anvil 156. The mesh element 24g is carried by the rod 160 into position between the stomach wall sections S1, S2. The retention sleeve 162 is retracted, allowing the mesh element 24g to expand to the position shown in FIG. 34D. One or more centering struts 166 extend between the mesh element 24g and rod 160 and maintain the mesh element in a generally centered orientation relative to the rod 160.

After the mesh element 24g is deployed, the tissue is compressed to the position shown in FIG. 34E to bring the opposed sections S1, S2 of the stomach wall into contact or close proximity with one another and to compress the mesh element 24g into a disk shape (also see FIG. 14B). This folding/compressing step may be accomplished by folding the vacuum chamber 14g itself, such as by pushing the shaft 16g in a distal direction while maintaining traction on the rod 160. After folding, the staple driver head 152 is pushed distally, driving the staples 154 through the tissue and against the anvil 156 as shown in FIG. 34F. In a simultaneous or separate step illustrated in FIG. 34G, the cannula 50g is advanced to core the tissue, thus forming the cutout C and snipping the centering struts 166 (not visible in FIG. 34G) connecting the mesh element to the rod 160. In forming the cutout C, the cannula 50g removes a margin of tissue surrounding the punctures created by tip 20g during its advancement towards channel 158.

The cannula 50g and tip 20g are withdrawn into shaft 16f, and the vacuum head 14g is separated from the tissue, leaving the cutout reinforced plication as shown in FIGS. 35A and 35B.

Plication System of the Third Preferred Embodiment

A third embodiment of a plicator 200 is shown in FIGS. 36A through 39. Plicator 200 includes a plication head 202 positioned on the distal end of an elongate shaft 204. As with prior embodiments, shaft 204 is of sufficient length to allow passage of the plication head 202 through the mouth and esophagus into the stomach, while the proximal end of the shaft remains outside the body. A vacuum source 206 is fluidly coupled to the proximal end of the shaft 202. Pullwires 208 extend through the shaft 204 from a handle (not shown) in the proximal end of the shaft and are anchored to a more distal location within the shaft 204, so that manipulation of the pullwires by a user allows for steering/deflection of the plication head 202. Shaft 204 may be formed of a plurality of spine members that articulate relative to one another but that may be locked in a desired position to fix the spine a desired shape.

Plication head 202 includes a tapered, atraumatic, distal tip 210 and a proximal portion 212 coupled to one another by one, two or more hinge member 214. In the FIGS. 36A-39 embodiment, three hinge members 214 are shown. Each of the illustrated hinge members includes distal and proximal hinge plates 216a, 216b joined together at central hinge 218. The hinge members 214 are moveable between the generally elongated position shown in FIG. 36A, and to the expanded position of FIG. 36B in which the central hinge 218 extends outwardly and in which the distance separating distal tip 210 and proximal end 212 of the plication head is decreased. As shown as a transparent element in the bottom plan view of FIG. 38A and the end view of FIG. 38B, a membrane or shroud 215 covers the hinge members 214 and is connected to the distal tip 210 and proximal portion 212 of the plication head 202 to form a vacuum chamber 217. An opening 219 in the shroud positionable in contact with stomach wall tissue to allow tissue to be drawn into the chamber during use. Shroud 215 is preferably formed of silicone, elastomeric material, or any other inelastic or elastic flexible or deformable biocompatible material capable of forming a vacuum chamber.

Figure 37A:
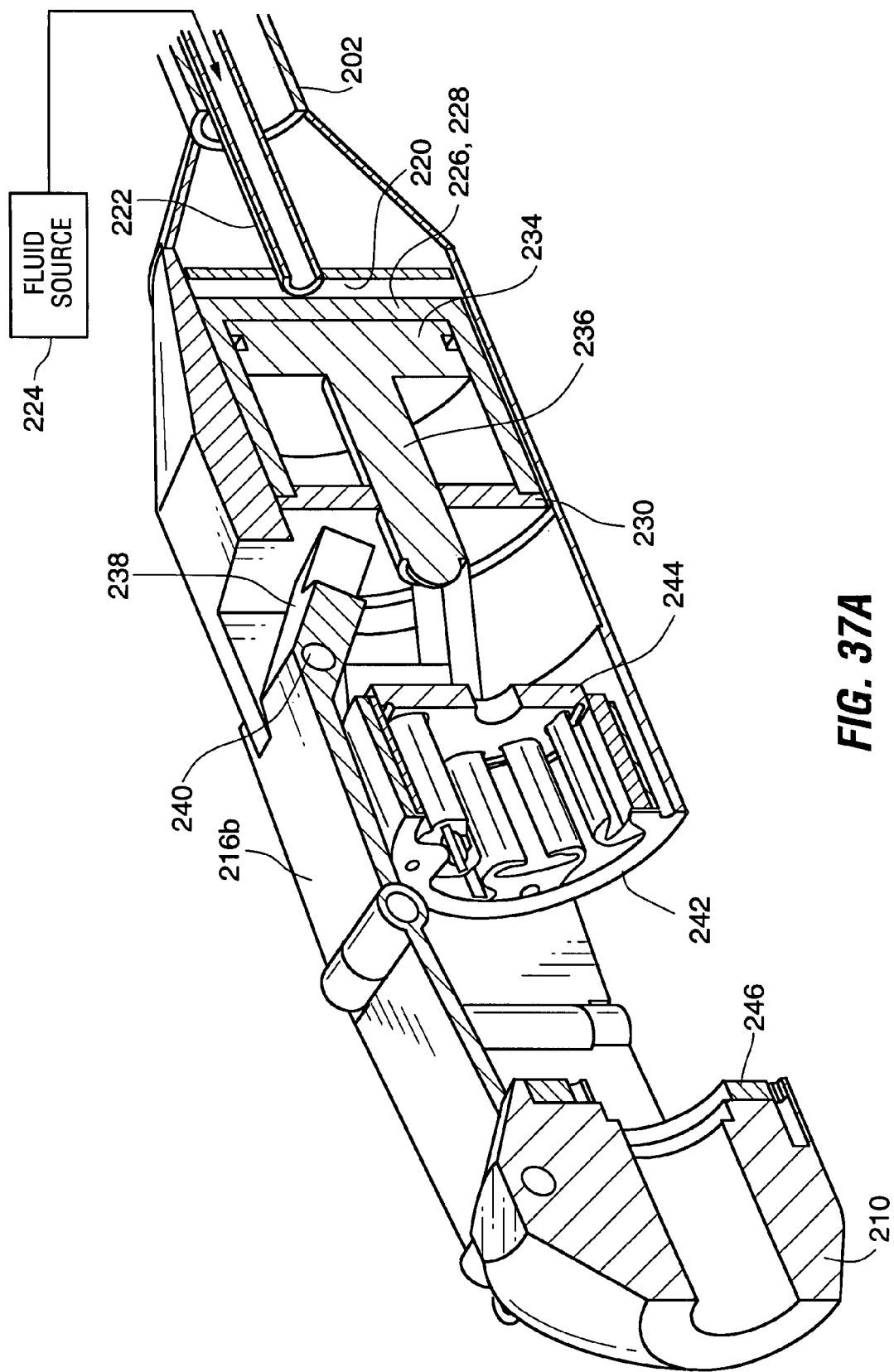

Referring to FIG. 37A, the proximal portion 212 of the plication head 202 includes a hydraulic chamber 220. The hydraulic chamber 220 is fluidly coupled by a fluid line 222 to a source of fluid 224. An outer piston 226 is disposed within the hydraulic chamber 220. In the illustrated embodiment, piston 226 is a hollow cylinder having a rear wall 228 and a front wall 230. Front wall 230 includes a center cutout 232. An inner piston 234 is disposed within the outer piston 226, and includes a longitudinal plunger 236 extending through the cutout 232.

Each of the proximal hinge plates 216b includes an inwardly-extending camming surface 238. The hinge plates include proximal pivots 240 such that distally-oriented pressure against camming surfaces 238 causes the hinge plates 216b to pivot about the pivots 240 into the position shown in FIG. 37B.

Proximal portion 212 of the plication head 202 includes a staple cartridge 242 containing staples arranged in an annular arrangement (not visible in the drawing), and a staple driver 244 positioned to drive staples from the distal end of the cartridge 242 when it is advanced in a distal direction into contact with the staples. Staple driver 244 may include a tissue penetrating element 248 (FIG. 40B) sufficiently sharp to form a hole in tissue.

An anvil 246 on the distal tip 210 is positioned to receive the prongs of staples driven by staple driver 242 and to fold the prongs into a closed position. Staple cartridge and anvil arrangements are well known in the surgical and endoscopic stapling art and need not be discussed in further detail. The staples (and sutures) described for use herein may be permanent or bioerodible/biodegradable.

Exemplary Method for Using the Third Preferred Embodiment

As with the previously discussed methods, a method of using the plication system 200 of the third embodiment is carried out under visualization using an endoscope advanced via the esophagus into the stomach.

Figure 36A:
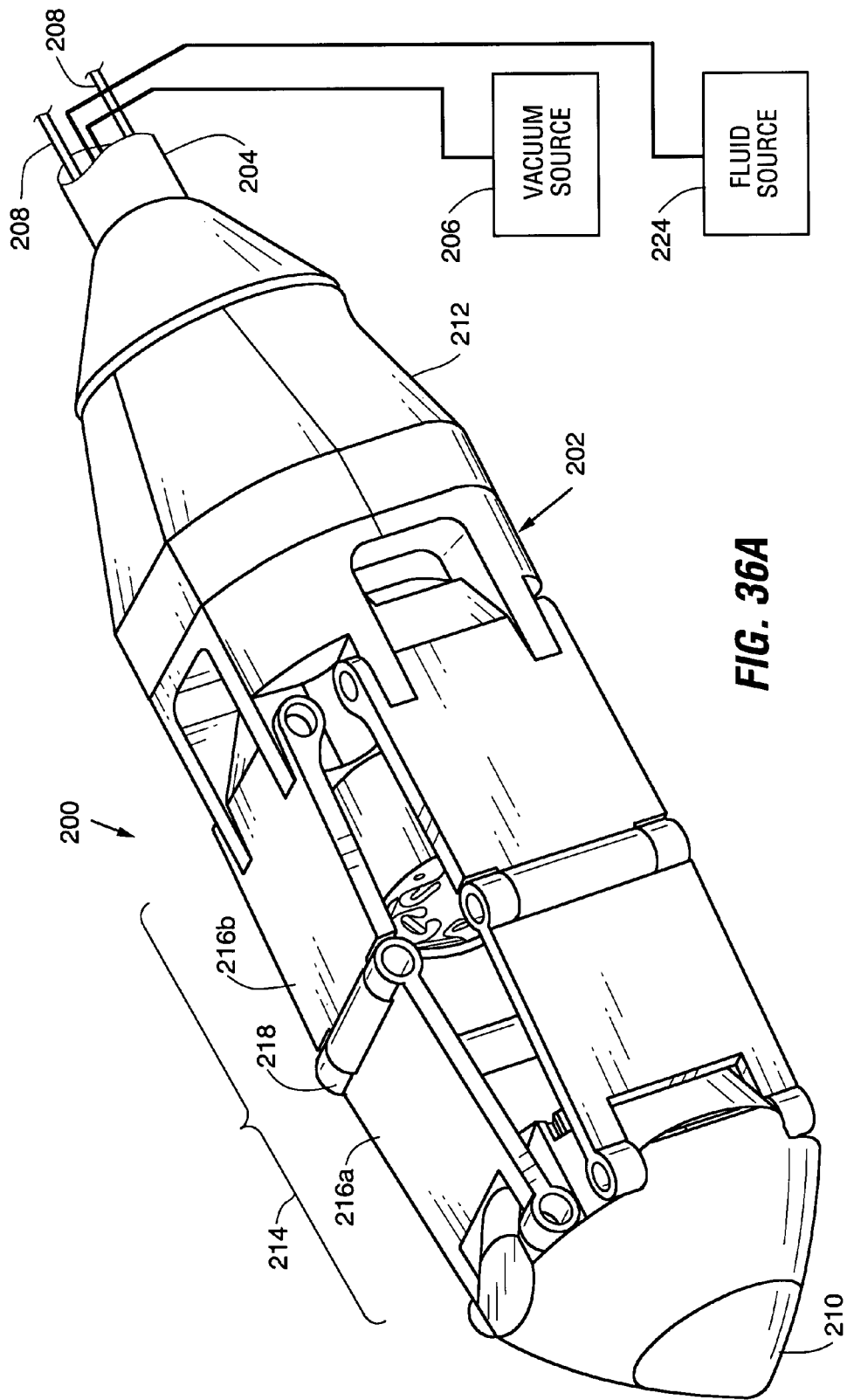
FIG. 36A is a perspective view of the plication head of an alternative embodiment of a plicator, shown in the streamlined positioned for transoral delivery to the stomach. The shroud is not shown to allow clear viewing of the underlying components.

In preparation for use, the plication head is positioned with the hinge members 214 in the streamlined position shown in FIGS. 36A and 37A. The plication head 202 is introduced transorally into the stomach, through an introducer sheath if needed to ensure smooth passage through the esophagus. Pullwires 208 are manipulated to orient the plication head 202 so that the opening 219 in the vacuum chamber 217 (FIGS. 38 and 39) is positioned in contact with stomach wall tissue at a location at which a plication is to be formed.

Figure 37B:
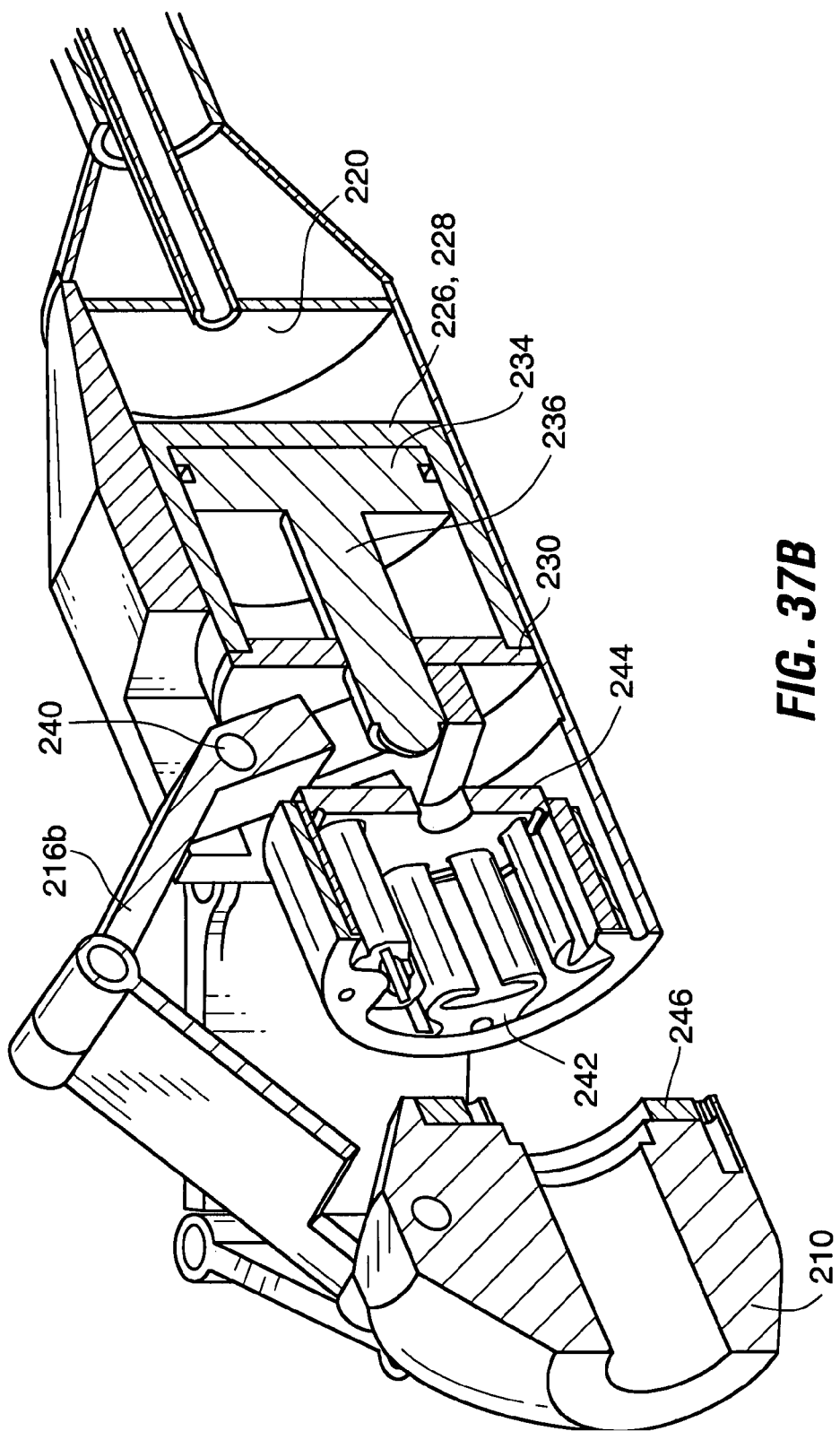

Next, as shown in FIG. 37B, hydraulic fluid is injected from fluid source 224 into chamber 220. The fluid pressure advances outer piston 226 in a distally direction, causing the front wall 230 of the piston 226 to contact the camming surfaces 238, thus pivoting the pivot plates 216b about proximal pivots 240. In response, hinge members 214 pivot as shown in FIG. 37B until they reach the partially expanded position shown in FIG. 37B. The vacuum source 206 is activated to create a vacuum which draws a pinch of tissue into the vacuum chamber 217, with serosal tissue surfaces generally facing one another as has been described with the other embodiments (see e.g. FIG. 34B). The flexible nature of the shroud forming the vacuum chamber 217 allows the vacuum chamber 217 to deform outwardly as tissue is drawn into the chamber.

Figure 37C:
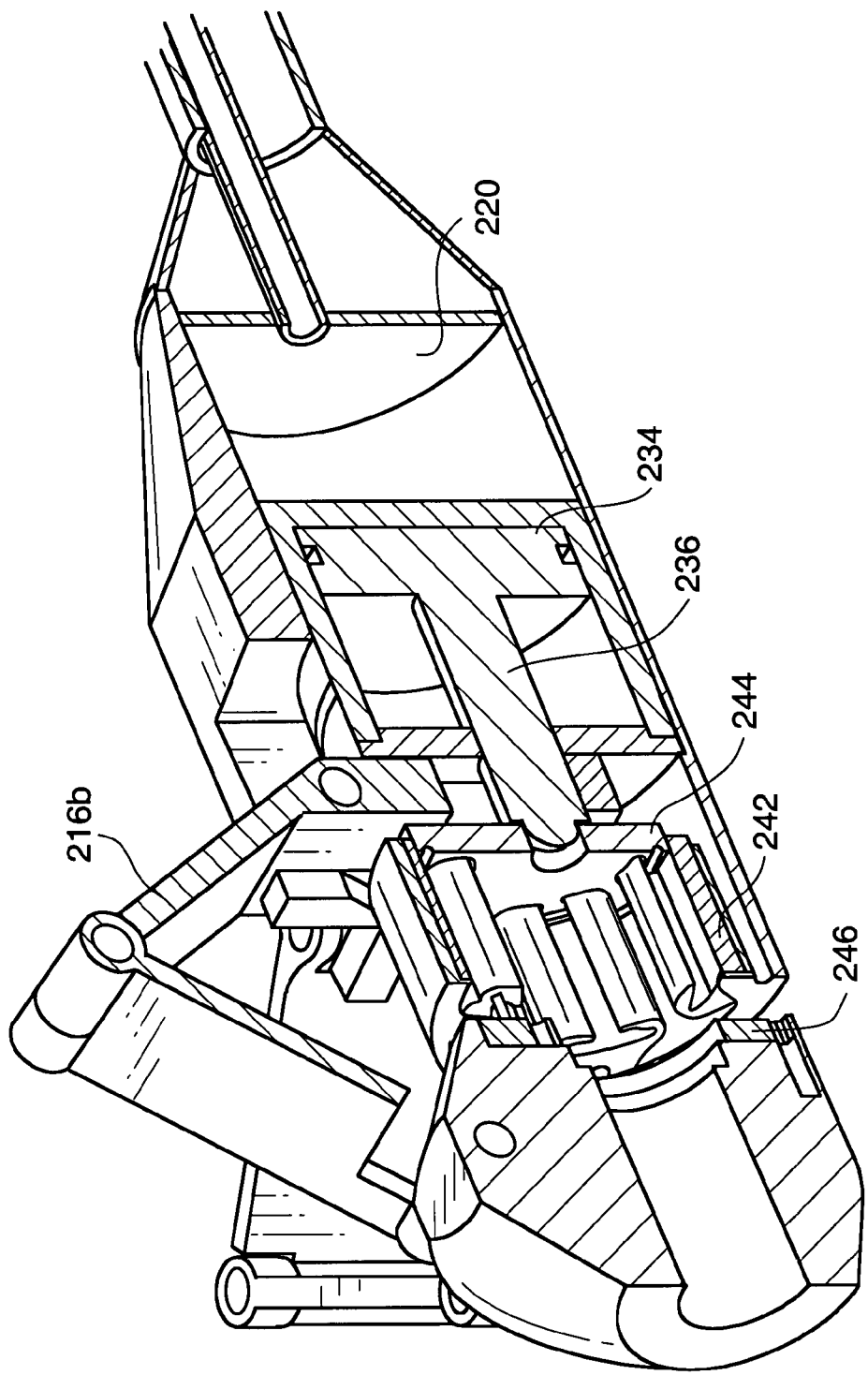
Figure 38:
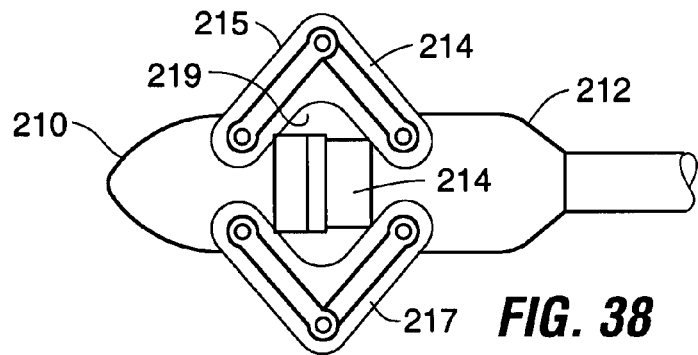
FIG. 38 is a bottom plan view of the plication head of FIGS. 36A-37C with the shroud in place and the hinge members in the expanded position.
Figure 39:
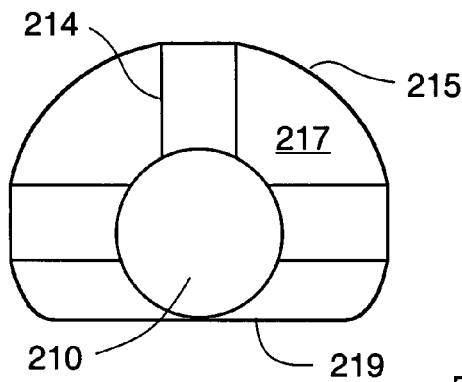
FIG. 39 is a front elevation view of the plication head as positioned in FIG. 38.

Once tissue is drawn in to the vacuum chamber 217, additional fluid is directed into the hydraulic chamber 220 to advance the outer piston 226 until the hinge members 214 are in the fully expanded position shown in FIG. 37C. Expansion of the hinge members 214 draws the distal tip 210 towards the proximal portion 212 of the plication head 202. This compresses the tissue within the vacuum chamber 217, bringing the opposed serosal tissue surfaces into contact or close proximity with each other similar to the tissue positions shown in FIG. 34E. Once the tissue is compressed, staples from the cartridge 242 are fired through the tissue by passing the staple pusher 244 through the staple cartridge 242. If the staple pusher 244 is provided with a tissue penetrating element 248 as shown in FIG. 40B, the tissue penetrating element 248 penetrates the opposed layers of stomach wall tissue as the staples are driven through the tissue, forming a hole surrounded by an annular pattern of staples.

The staples fold against the anvil 246. After stapling, the hinge members are moved to the collapsed position shown in FIG. 36A. The plicator is separated from the tissue and withdrawn from the body. The tapered profile of the proximal portion 212 of the plication head 202 allows the plication head 202 to pass through the gastro-esophageal junction, esophagus, and mouth with minimal trauma.

Figure 40A:
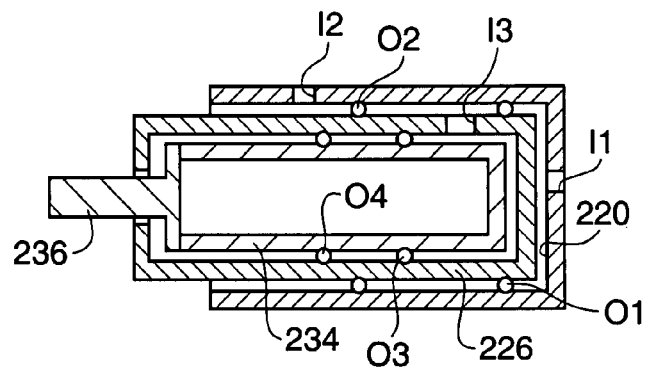
FIG. 40A is a cross-sectional side views of the hydraulic chamber a piston assembly used for expanding the vacuum chamber, compressing tissue, and driving the staples in the embodiment of FIGS. 36A-39.

In the illustrated embodiment, the staple pusher 244 is driven by the injection of hydraulic fluid into the cylindrical piston 226. The fluid drives plunger 236 distally into contact with the staple pusher 244, which in turns drives through the cartridge 242 to advance the staples. FIG. 40A illustrates one arrangement of the pistons 226, 234 within the hydraulic chamber 220 that will allow this to be achieved. As shown, hydraulic cylinder 220 includes first and second inlets I1 and I2, and the piston 226 includes a third inlet I3. O-ring seals O1, O2 are positioned on the exterior surface of piston 226 and o-ring seals O3 and O4 are positioned on the exterior surface of the inner piston 234. When hydraulic pressure is applied to I1, the piston 226 advances distally (towards the left in the view shown) to expand the hinge members 214 (FIG. 37C) and compress the tissue as discussed above. After o-ring seal O2 has moved distally of inlet I2, fluid pressure can be directed through I2 and into I3, causing inner piston 234 to be driven distally to advance the staple pusher 244 (FIG. 37A). Although in the FIG. 40A embodiment the hydraulics for tissue compression and stapling and combined on the proximal side of the plication head, these functions may be separated, with the hydraulics driving one function positioned distally of the vacuum chamber and the hydraulics driving the other function positioned proximally of the vacuum chamber.

Figure 41A:
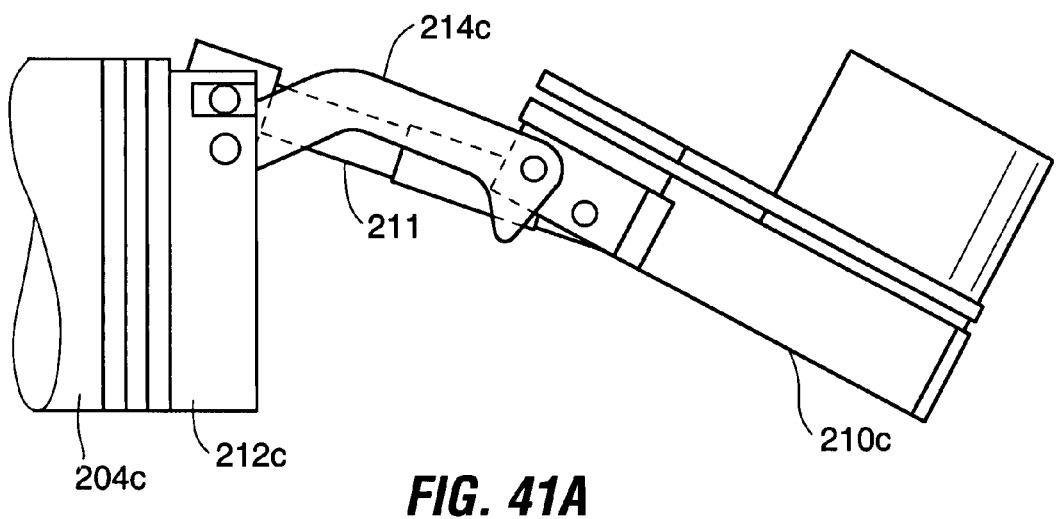
FIGS. 41A and 41B are side elevation views of a modified plication head with the shroud not shown to permit the underlying components to be seen.
Figure 41B:
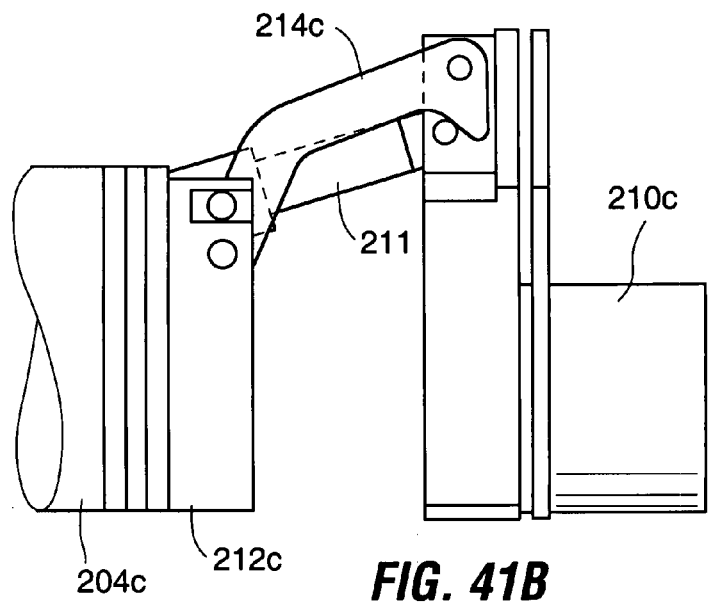
Figure 41C:
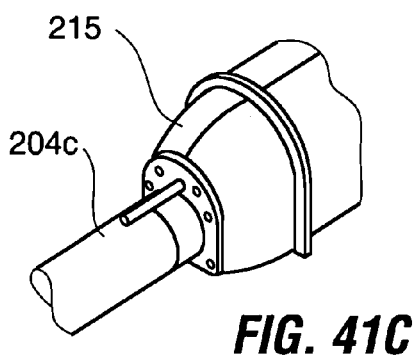
FIG. 41C is a perspective view of the plication head of FIGS. 41A and 41B, with the shroud shown.

FIGS. 41A and 41B are side elevation views of a modified plication head 202c in which the distal and proximal portions 210c, 212c are coupled by a hinge 214c that is actuated by a lead screw 211. Lead screw is extended as shown in FIG. 41A to elongate the plication head 202c for passage into the body and for expansion of the vacuum chamber which, as with the FIG. 36A embodiment, is defined by a shroud 215 (FIG. 41C). Once tissue is drawn into the chamber, the lead screw 211 is actuated to bring the distal and proximal portions 210c, 212c into alignment for compression and stapling of the tissue as described above.

Plication Reinforcements

Reinforcements of various types may be implanted in or on plications formed using the plication system. Such reinforcements may function to reinforce the staple array, help to more evenly distribute the forces applied to the tissue by the staples, and/or facilitate bonding between the opposed serosal layers. Suitable reinforcements include ones positionable on or between the serosal tissue layers ("serosal side reinforcements"), as well as those delivered on the side of the mucosal tissue ("mucosal side reinforcements").

Serosal side reinforcements have been discussed in connection with the first and second embodiments. A reinforcement similar to mesh element 24 described in connection with FIGS. 14A, 14B may serve as a permanent or semi-permanent implant that will reinforce the staple array applied to the tissue and/or facilitate serosal tissue bonding between the layers of stomach wall tissue that are to be stapled or sutured together. For this purpose, the material may be a synthetic or non-synthetic mesh (formed of nitinol, polyester, or other natural or synthetic material), porous or non-porous material, slotted material, or any other material through which adhesions will form or onto which tissue will grow. Examples include, but are not limited to, polypropylene, materials sold under the trade names Goretex or Dacron, or tissue graft material such as the Surgisis material sold by Wilson Cook Medical, Inc. The material may be treated with tissue-ingrowth promoting substances such as biologics.

Figure 42A:
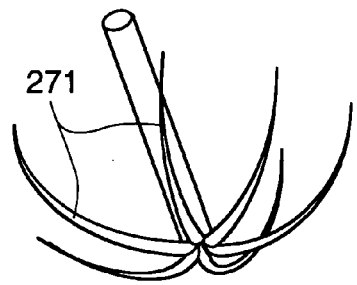
FIG. 42A is a perspective view of an expandable frame for deploying a reinforcing element.
Figure 42B:
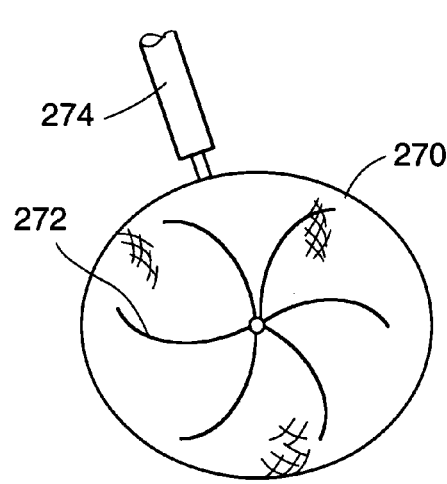
FIG. 42B shows a reinforcing element on the frame of FIG. 42A.

In an alternative embodiment of a serosal side reinforcement shown in FIGS. 42A and 42B, a reinforcement 270 (which may be formed of a polyester fabric, mesh, or any other material including those listed elsewhere in this application) is carried by a frame 272 having a plurality of outwardly extending arms that spring to an expanded position when released from a hollow tube. The tube might be any of the tubes described above for delivering mesh or sclerosing agents etc. to the serosal tissue, e.g. tube 50g of FIG. 34A. The hollow tube 274 is passed through stomach wall tissue so that its distal end is positioned between serosal layers (e.g., the position of needle 50a in FIG. 26B). The frame 272 is advanced out the distal end of the needle to allow the arms of the frame to spread to the expanded position shown, thereby expanding the reinforcement between the opposed serosal layers. The reinforcement is fixed between the layers by the staples driven through the opposed regions of stomach wall, and the frame is withdrawn from the needle and out of the body.

Mucosal side reinforcements may take the form of reinforcements that are positioned on or adjacent to one or both of the mucosal surfaces lining the "pinch" of tissue that will form the plication. These reinforcements may be features of the staples or staple arrays, or they may be separate components engaged by staples as the staples are advanced through the tissue.

Figure 43A:
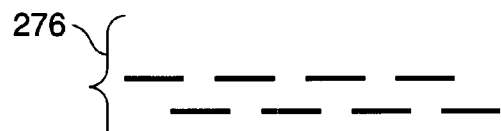
FIGS. 43A and 43B are plan views illustrating staple patterns.
Figure 43B:
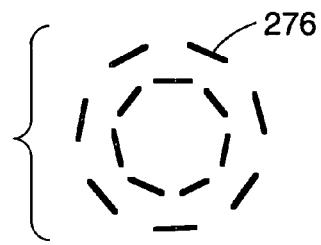
Figure 43C:
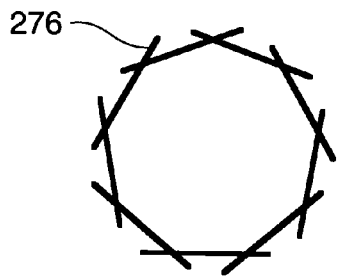
FIGS. 43C-43E are plan views illustrating interlocking staple patterns.
Figure 43D:
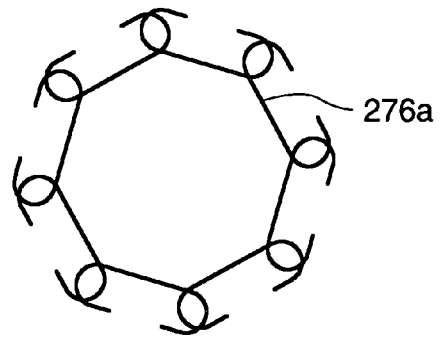
Figure 43E:
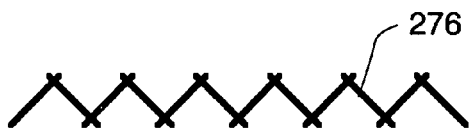

Referring to FIG. 43A, conventional stapling procedures will often include two parallel rows of staples, in which the staples in one row are laterally offset from the staples of the other row. According to the disclosed method, it is useful to employ this technique to the circular staple pattern delivered using the plicators described above, to produce two concentric rings of offset staples 276, as shown in FIG. 43B. It has been found to be additionally beneficial to form mucosal side reinforcements by linking or interlocking the staples to provide greater structural reinforcement to the stapled tissue and/or to more evenly distribute forces applied to the tissue by the staples. Linked staple arrays may be formed by arranging the staples 276 in the cartridge of the plicator in a single circular pattern to interlock as shown in FIG. 43C, or in a double circular pattern with two concentric rings of interlocked staples. The staples 276a may be curvilinear so as to form a locking pattern shown in perspective view of FIG. 43D. A linear arrangement of staples 276 may also be linked as shown in FIG. 43E.

Figure 44A:
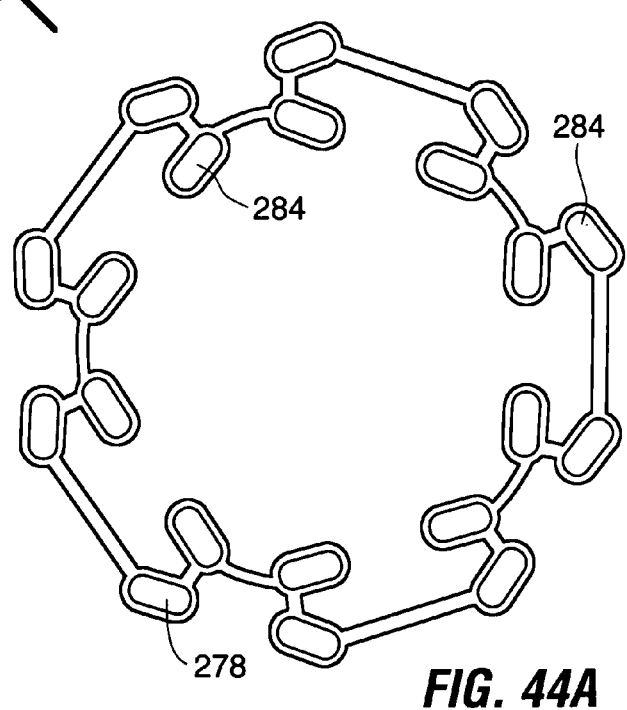
FIGS. 44A and 44B are plan views of reinforcing rings.
Figure 44B:
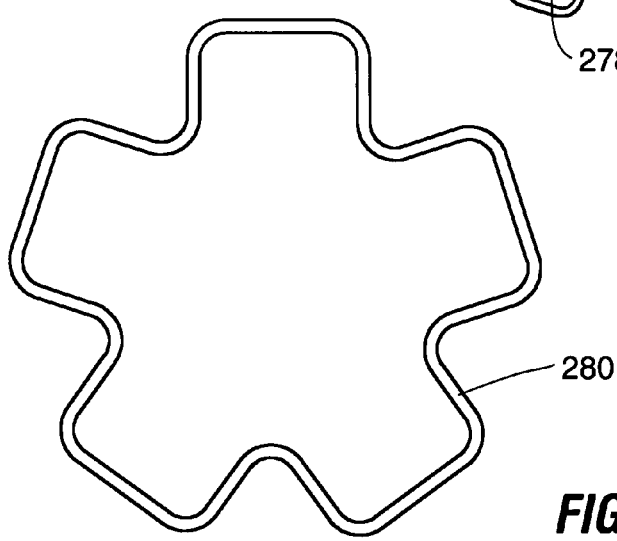

In alternative embodiments, staples are linked together by reinforcing members formed of metallic or polymeric materials, such as nitinol, titanium, stainless steel PEEK, or other biocompatible materials including those that are bioerodible/biodegradable. According to these embodiments, the reinforcing members are positioned on one or both of the mucosal sides of the "pinch" of tissue engaged by the plication system such that they are captured by staples being driven through the tissue. In a preferred embodiment, the staples capture a cartridge side reinforcing ring 278 (FIG. 13A) as they leave the cartridge and capture an anvil side reinforcing ring 280 (FIG. 44B) as the anvil shapes and bends them. Upon completion of the plication, the staples are linked to one another so that they cannot separate or expand radially. The rings promote even distribution of forces around the ring of staples.

Figure 45A:
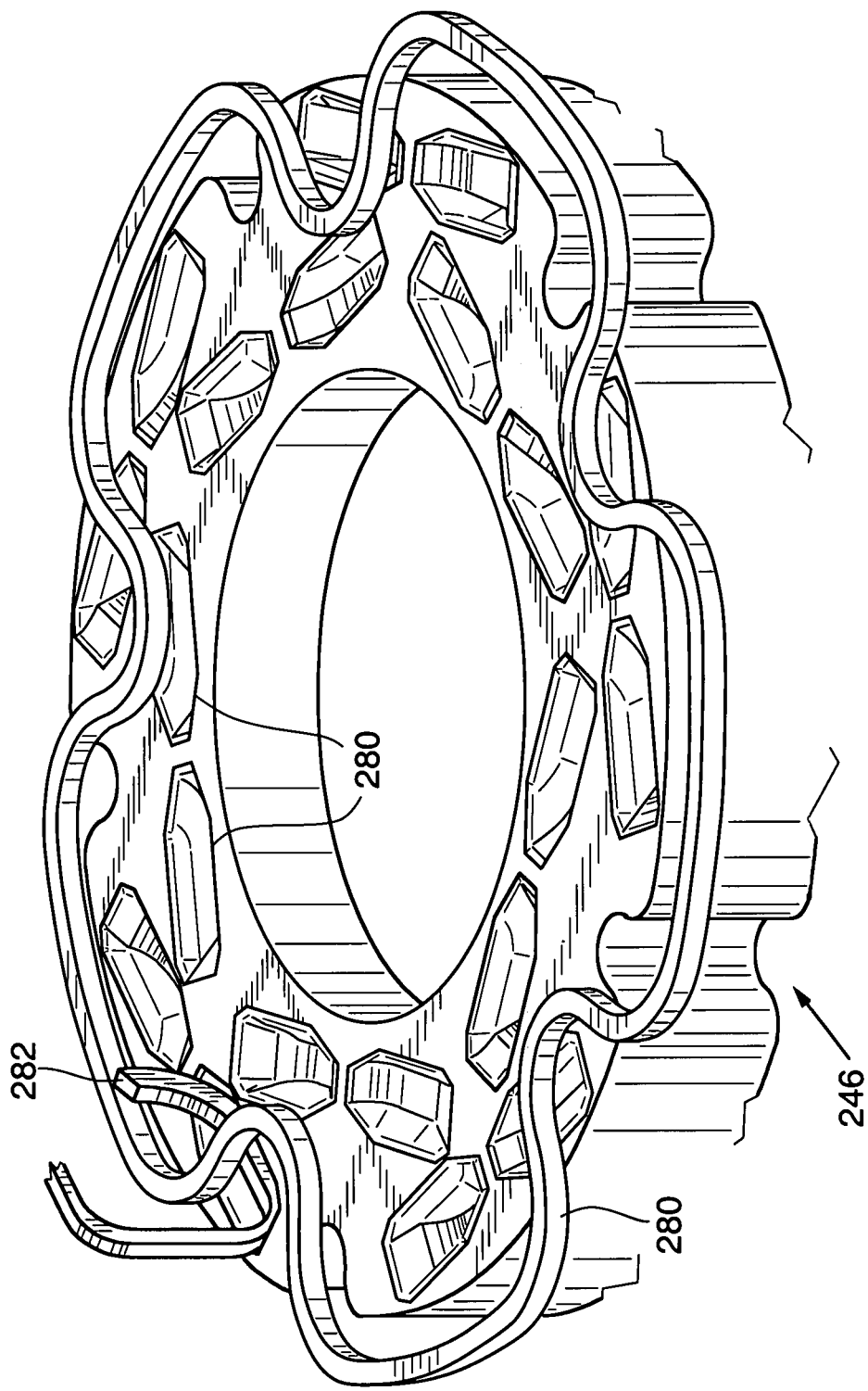
FIG. 45A is a perspective view showing the reinforcing ring of FIG. 44B on a stapler anvil.
Figure 45B:
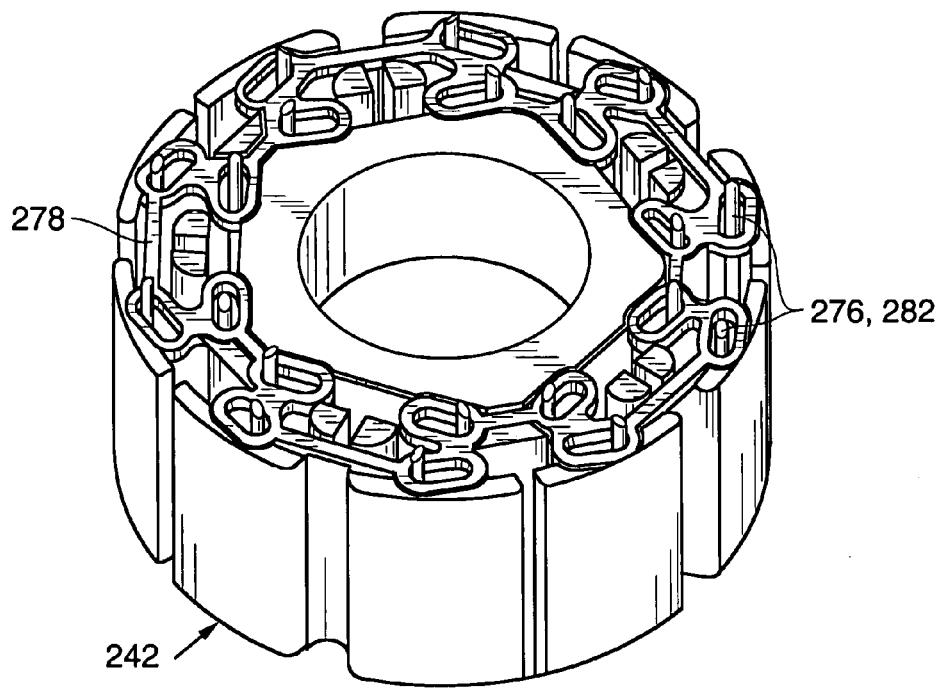
FIG. 45B is a plan view of the reinforcing ring of FIG. 44A on a staple cartridge.
Figure 46A:
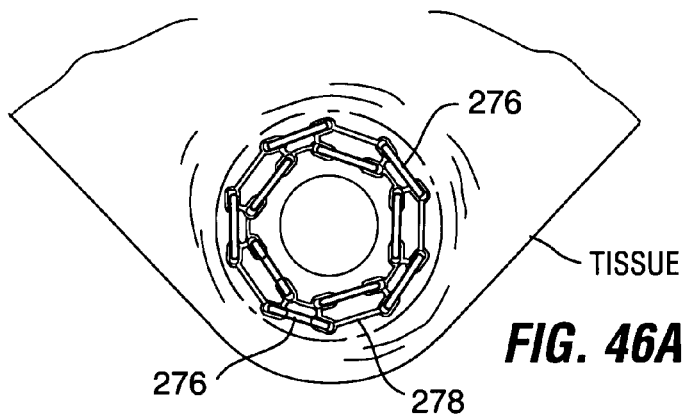
Figure 46B:
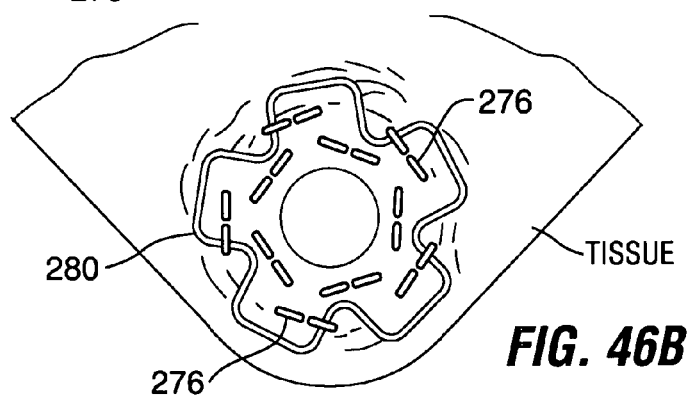

The reinforcing rings are preferably provided separate from the staples although they instead may be integral with the staples. In the illustrated embodiment, ring 280 is positioned against the staple anvil 246 as shown in FIG. 45A. Ring 278 is seated within the cartridge 242 (FIG. 45B), with the staples 276 aligned with their prongs 282 extending through a plurality of the loops 284 in the ring 278. When staples 276 are driven from the cartridge, they capture ring 278 against the adjacent mucosal tissue as shown in FIG. 46A. The staple legs/prongs 282 pass through the stomach wall tissue into contact with the indentations 286 of the anvil 246. When they contact the anvil 246, the prongs 282 fold around the staple ring 280 to capture the ring 280 and interlock the staples on the anvil side of the plication as shown in FIG. 46B. Rings or other interlocking elements of this type may be used with single- or double-staple row configurations.

Rings 278, 280 are shown as generally circular, although alternative reinforcements of different shapes and patterns may also be used, including those shaped to accommodate linear, oval and other staple patterns.

Applications for Cutout Plications

FIGS. 47A through 49 illustrate examples of applications for cutout plications formed within the stomach using any methods or system, including those described above. As shown, the cutout plications can eliminate the need for anchor loops of the type described in connection with the first embodiment. Each of these applications is preferably (but optionally) performed in a separate procedure from that in which the plications are formed, so as to allow serosal bonding to occur before the plicated tissue is subjected to stresses imparted by implants and/or further manipulation.

Figure 1A:
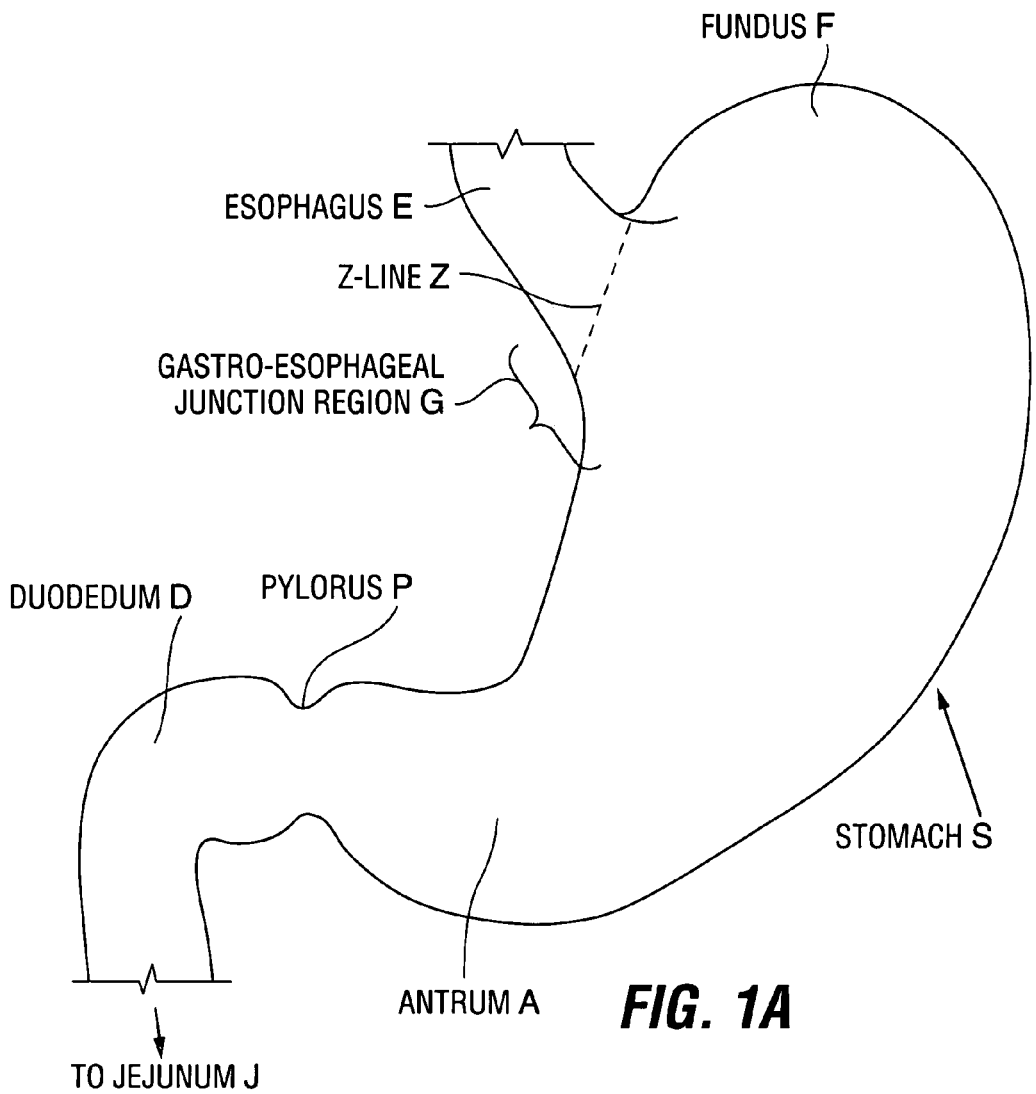
FIG. 1A is a schematic illustration of a human stomach and a portion of the small intestine.
Figure 1B:
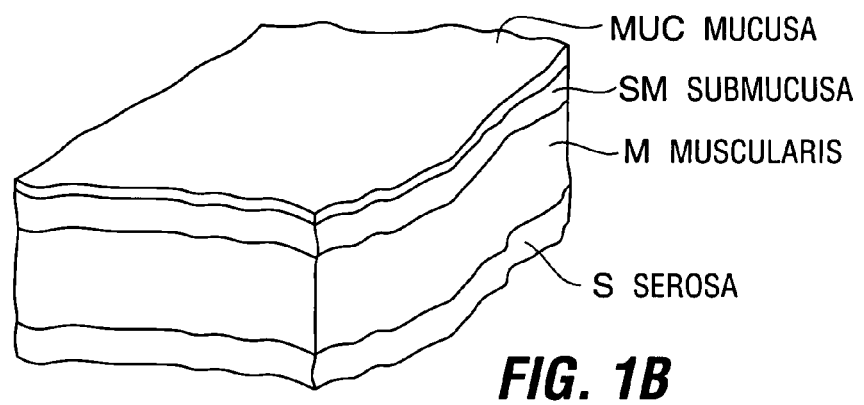
FIG. 1B is a cross-sectional perspective view of a portion of a stomach wall, illustrating the layers of tissue forming the wall.
Figure 2:
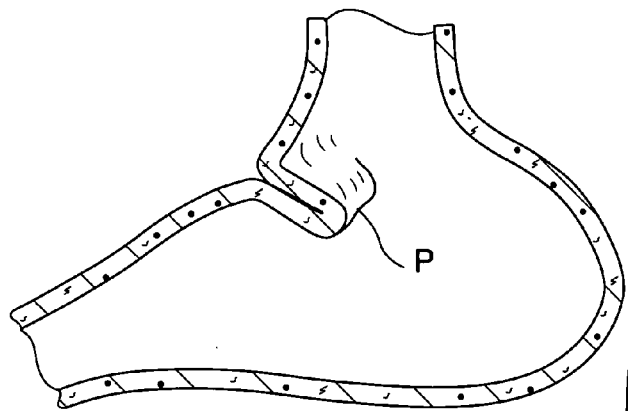
FIG. 2 schematically illustrates a serosal tissue plication formed in stomach tissue.
Figure 5:
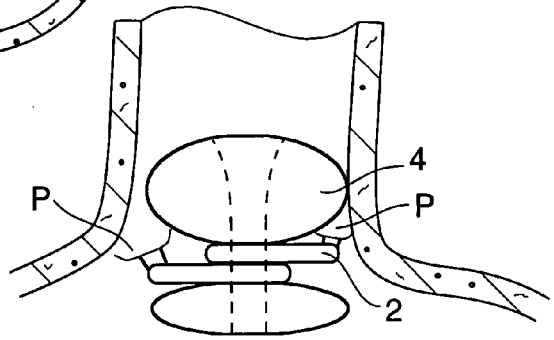
FIG. 5 schematically illustrates the satiation implant of FIG. 4 coupled to the loops of FIG. 3.
Figure 3:
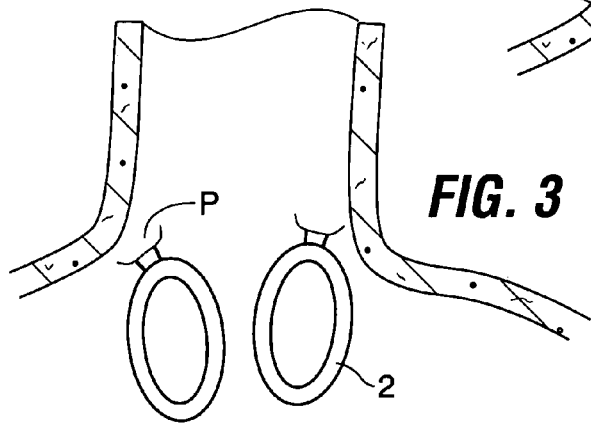
FIG. 3 schematically illustrates a pair of loops attached to serosal tissue plications, prior to the positioning of a medical implant within the loops.
Figure 4:
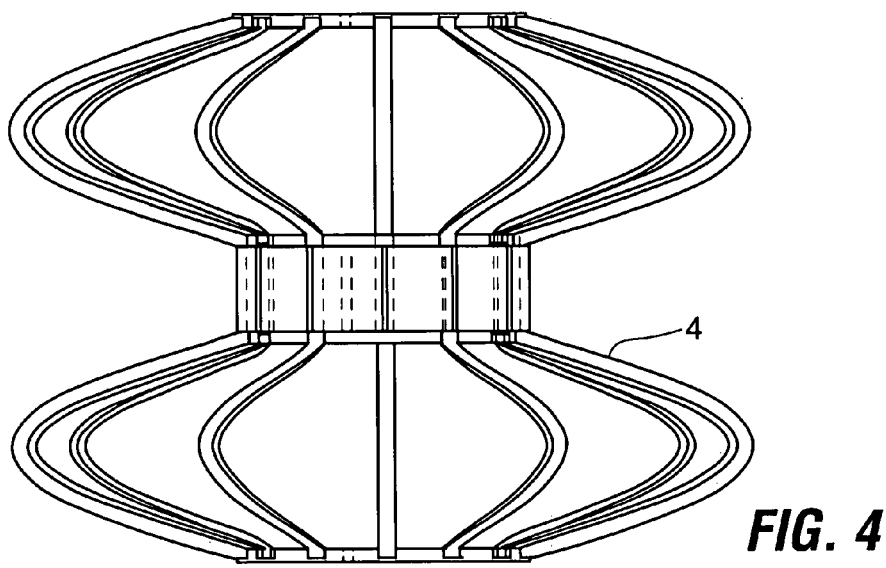
FIG. 4 is a cross-sectional side elevation view of a satiation implant.
Figure 47A:
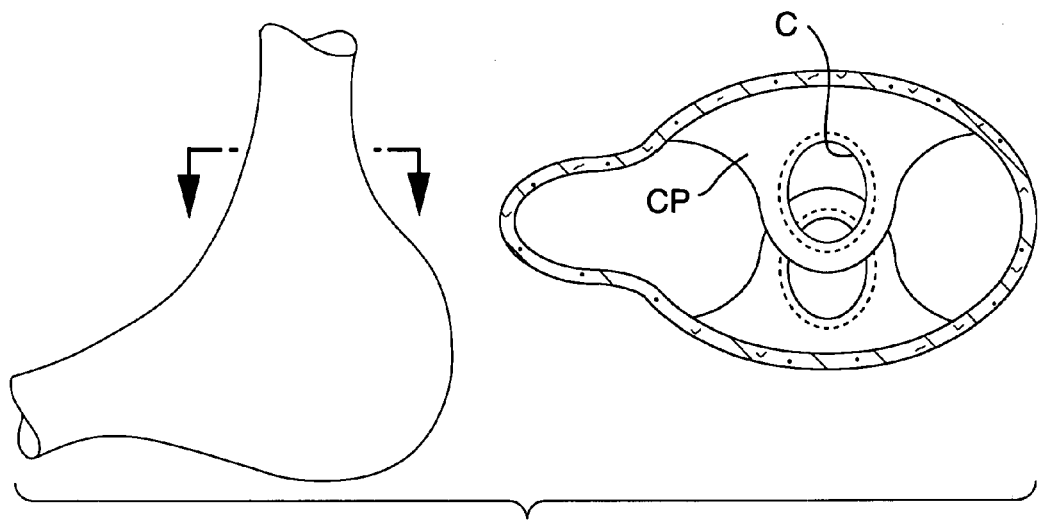
FIG. 47A is a cross-sectional top view of a stomach, illustrating movement of cutout plications into alignment in preparation for insertion of an implant through their cutouts.
Figure 47B:
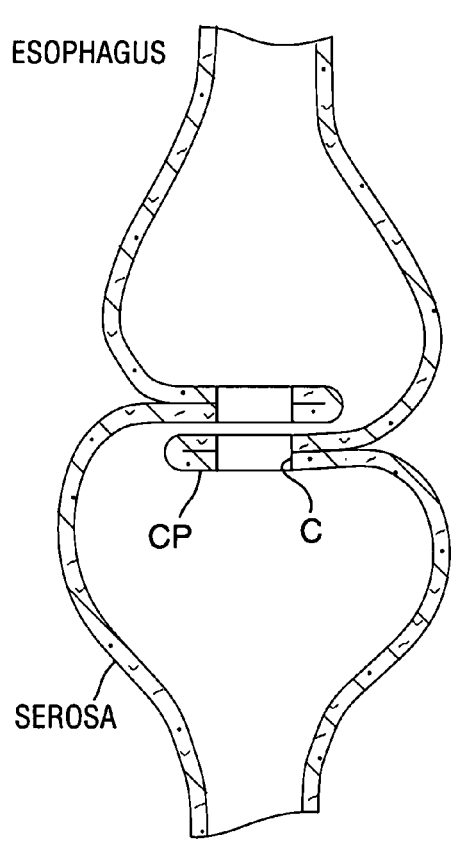
FIG. 47B is a cross-sectional side view of a stomach, illustrating the alignment step of FIG. 47A.
Figure 47C:
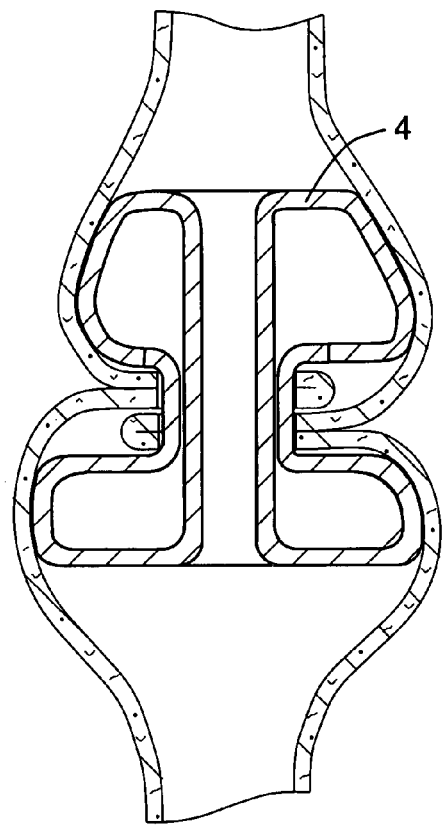
FIG. 47C is a cross-sectional side view similar to FIG. 47B, with the implant in place within the cutouts.

A first application shown in FIGS. 47A through 47C uses two or more cutout plications CP, preferably formed at the gastro-esophageal junction region of the stomach. According to this application, the cutouts C of the plications are brought into partial or full alignment with one another (FIGS. 47A and 47B) using an endoscope or another endoscopic instrument. A restrictive implant such as the implant 4 shown in FIG. 4 is threaded through the aligned cutouts while in a radially-collapsed position, and is then allowed to expand to the position shown in FIG. 47C. Instruments and methods for orienting and expanding an implant of this type are shown and described in U.S. application Ser. No. 11/439,461, filed May 23, 2006. Once in place, the implant greatly reduces the amount of food a patient can consume, by slowing the rate at which food can descend from the esophagus into the stomach.

Figure 48A:
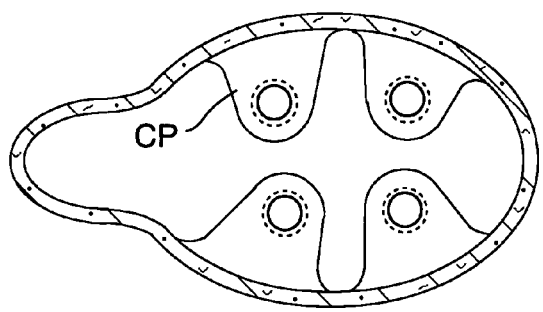
FIG. 48A is a cross-sectional top view of a stomach illustrating an arrangement of cutout plications.
Figure 48B:
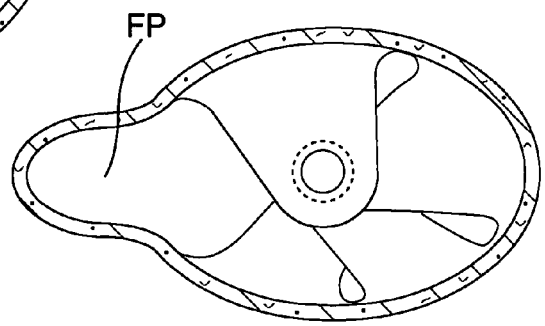
FIG. 48B is a cross-sectional top view similar to FIG. 48A, showing the cutout plications drawn into alignment with one another.
Figure 48C:
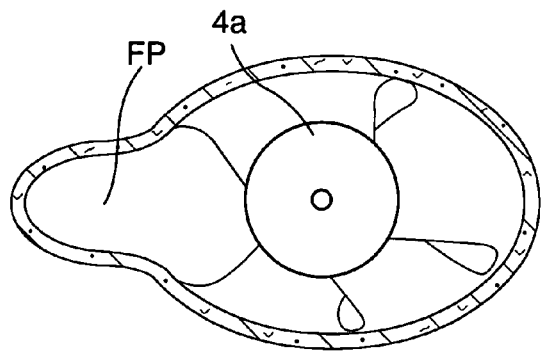
FIG. 48C is a cross-sectional top view similar to FIG. 48B, showing an implant positioned in the aligned cutouts of the plications.
Figure 48D:
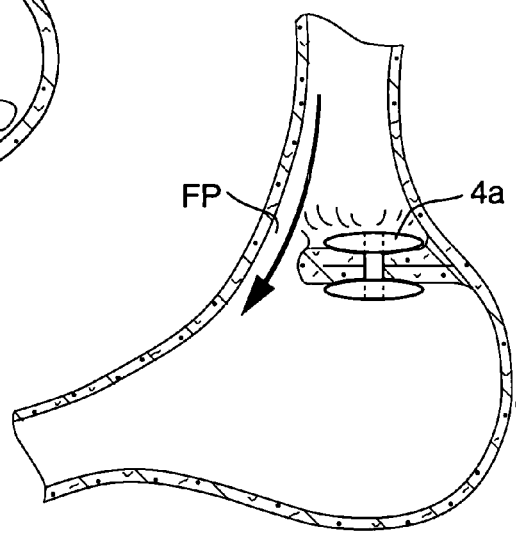
FIG. 48D is a cross-sectional side view of the stomach, illustrating the formation of a food passage in the stomach using the arrangement of plications and the implant shown in FIG. 48C.

In the method shown in FIG. 48A, multiple cutout plications CP are formed in select positions allowing the plications to be drawn together so as to significantly narrow the channel through which food can pass through the stomach. For example, the plications CP of FIG. 48A are arranged such that manipulating the plications to place their cutouts C in alignment causes the plications themselves to form a barrier against passage of food. This arrangement limits most food flow to a narrow food passage FP and creates a gastric pouch GP adjacent to the food passage. An implant 4a is positioned within the cutouts C as described above to retain the plications CP in their gathered arrangement. The implant 4a may have a similar configuration to the implant 4 of FIG. 4, including a through-hole allowing some passage of food through the implant, or it may be impenetrable by food thus forming a plug largely preventing passage of food and gastric juices through the cutouts C. The implant may include a valve oriented to minimize restriction of food flow out of the stomach during vomiting. Other implants that will retain the gathered configuration of the plications CP may alternatively be used, including lengths of biocompatible material passed through the cutouts and knotted or otherwise fastened into loops. In other embodiments, the collective sizes and numbers of the plications may themselves be sufficient to restrict flow of food into the stomach, without the need for any implants to connect them to one another.

In either embodiment, if the implant 4, 4a is to be removed or replaced with an implant of different dimensions (e.g. so as to slow the rate of weight loss following a period of significant weight loss, or to increase the rate of weight loss), endoscopic instruments may be used to withdraw the implant from the cutouts C and to remove the implant from the stomach.

Figure 49:
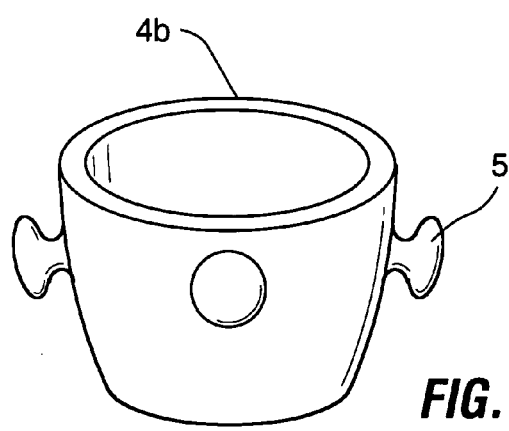
FIG. 49 is a perspective view of a restrictive implant having buttons insertable through holes formed in stomach tissue plications.

In another embodiment shown in FIG. 49, a restrictive pouch 4b may include anchors 5 that are inserted into cutout plications CP. Anchors 5 are shown as having a button shape, but they may alternatively be other structures including loops that close on themselves to prevent detachment from the cutout, or they might be legs of the type disclosed in WO 2005/037152.

As is evident from above, the disclosed endoscopic systems function to draw a tissue into the stomach to form a depression on the exterior surface of the stomach, and staple (or suture, or fasten or adhere etc) the opposed stomach wall sections lining the depression together another to form a plication. The system may additionally place material of a type that will promote strong tissue adhesion within the depression (on the exterior of the stomach) and retain the material between the serosal surfaces to enhance. Additionally or alternatively, mucosal reinforcements such as structures that interconnect the staples may be implanted. While these systems provide convenient embodiments for carrying out this function, there are many other widely varying instruments or systems may alternatively be used within the scope of the present invention. Moreover, the disclosed embodiments may be combined with one another in varying ways to produce additional embodiments. Thus, the embodiments described herein should be treated as representative examples of systems useful for forming endoscopic tissue plications, and should not be used to limit the scope of the claimed invention.

Any and all patents, patent applications and printed publications referred to above, including those relied upon for purposes of priority, are incorporated herein by reference.

We claim:

1. An endoscopic stapler for fastening tissue, comprising: a fastening head including:
   (i) a first portion including a staple cartridge with one or more staples therein;
   (ii) a second portion including an anvil;
   (iii) at least one hinge member connecting the first portion and the second portion for movement toward and away from one another along an axis extending through the first portion and the second portion, wherein each hinge member of said at least one hinge member includes first and second sections that are mounted on said first and second portions, respectively; and
   (iv) a flexible membrane extending between the first portion and the second portion to define a tissue capture region therebetween, wherein the at least one hinge member is configured such that movement of the first portion and the second portion toward one another to staple tissue positioned in the tissue capture region corresponds to movement of the first and second sections of each hinge member outwardly away from said axis to enlarge the tissue capture region in a direction orthogonal to said axis.

2. The stapler of claim 1, wherein the at least one hinge member includes three hinge members connecting the first and second portions.

3. The stapler of claim 1, wherein the flexible membrane extends over the at least one hinge member, said flexible membrane including an opening through which tissue can be drawn into the tissue capture region when a vacuum is applied.

4. The stapler of claim 1, for use in fastening a tissue fold to make a tissue plication, wherein tissue in the tissue capture region forms a tissue fold.

5. The stapler of claim 1, wherein the staple cartridge includes an annular array of staples.

6. The stapler of claim 1, wherein the first section and the second section of each hinge member are connected together by a hinge.

7. The stapler of claim 1, for use in fastening tissue within a body cavity of organ, the stapler further including an elongate shaft having proximal and distal ends, where the fastening head is attached to the distal end of the shaft with a long axis of the shaft aligned with the axis of movement of the two portions of the fastening head.

8. The stapler of claim 1, wherein the first section of each hinge member is pivotably coupled to the first portion of the fastening head and the second section of each hinge member is pivotably coupled to the second portion of the fastening head.

9. The stapler of claim 1, wherein the first portion of the fastening head includes a needle, and the second portion of the fastening head includes a catch for engaging a portion of the needle.

10. The stapler of claim 1, further comprising a reinforcing element positioned between the first and second portions such that the reinforcing element is adapted to be secured to the stapled tissue.

11. The stapler of claim 10, wherein the reinforcing element is positioned in proximity to the anvil such that a staple passing through the tissue into contact with the anvil will fold around the reinforcing element to secure the reinforcing element to the stapled tissue.

12. The stapler of claim 1, further including a piercing element extendable through tissue in the tissue capture region to form a hole in tissue layers stapled together by the fastening head.

13. The stapler of claim 12, wherein the piercing element is positioned to form a hole bounded by staples delivered by the fastening head.

14. The stapler of claim 1, further comprising a piston assembly coupled to the staple cartridge for advancing the at least one staple from the cartridge.

15. The stapler of claim 14, wherein the piston assembly comprises at least one hydraulic chamber.

16. The stapler of claim 1, wherein the flexible membrane is radially outside of the at least one hinge member.

17. The stapler of claim 1, wherein the at least one hinge member includes a first material, and the flexible membrane includes a second material different than the first material.

* * * * *